(12) United States Patent
Rodgers

(10) Patent No.: US 7,911,348 B2
(45) Date of Patent: *Mar. 22, 2011

(54) METHODS FOR REFINING PATIENT, STAFF AND VISITOR PROFILES USED IN MONITORING QUALITY AND PERFORMANCE AT A HEALTHCARE FACILITY

(75) Inventor: Mark E. Rodgers, Jackson, MS (US)

(73) Assignee: Bee Cave, LLC., Austin, TX (US)

( * ) Notice: Subject to any disclaimer, the term of this patent is extended or adjusted under 35 U.S.C. 154(b) by 201 days.

This patent is subject to a terminal disclaimer.

(21) Appl. No.: 11/779,096

(22) Filed: Jul. 17, 2007

(65) Prior Publication Data
US 2008/0015903 A1 Jan. 17, 2008

Related U.S. Application Data

(63) Continuation-in-part of application No. 11/608,074, filed on Dec. 7, 2006, now Pat. No. 7,786,874.

(60) Provisional application No. 60/748,376, filed on Dec. 9, 2005, provisional application No. 60/799,041, filed on May 10, 2006, provisional application No. 60/835,662, filed on Aug. 4, 2006, provisional application No. 60/826,634, filed on Sep. 22, 2006.

(51) Int. Cl.
*G08B 23/00* (2006.01)

(52) U.S. Cl. .......................... 340/573.1; 600/301; 705/2

(58) Field of Classification Search ............... 340/573.1, 340/286.01, 286.06, 539.12; 600/300, 301; 705/2, 3
See application file for complete search history.

(56) References Cited

U.S. PATENT DOCUMENTS 1,388,242 A 8/1921 Dodds
(Continued)

FOREIGN PATENT DOCUMENTS

DE 3443334 6/1986
(Continued)

OTHER PUBLICATIONS

VersusTech, Oct. 23, 2005, pp. 1-8.
(Continued)

*Primary Examiner* — George A Bugg
*Assistant Examiner* — Edny Labbees
(74) *Attorney, Agent, or Firm* — Workman Nydegger

(57) ABSTRACT

Methods, systems and computer program products are used in monitoring patients, staff, assets and visitors at a facility, initiating a response to prevent or mitigate harm, and assess and ensure overall quality and performance, and refine individual patient, staff and visitor profiles. A plurality of sensors throughout the facility provide multiple data streams relating to the locations of patients relative to at least one of caregivers, assets, other patients, visitors or one or more fixed locations. A computer system analyses the data stream and determines the location and/or movements of the patients relative to the caregivers, assets, other patients, visitors and/or fixed locations. A profile containing individual data for the patient is used to accurately detect events, including actionable events, ensure completion of prescribed care, assess patient wellness, and, in some cases, provide tailored patient specific responses to detected events. Patient profiles are periodically refined by means of an information feedback loop in order to more accurately predict (actionable) events, provide adequate care and ensure a desired level of patient wellness. Staff and visitor profiles can be used to measure staff and visitor performance at a facility.

31 Claims, 20 Drawing Sheets

U.S. PATENT DOCUMENTS

| | | | | |
|---|---|---|---|---|
| 2,592,166 | A | 4/1952 | McLean et al. | |
| 2,604,639 | A | 7/1952 | Killifer | |
| 3,039,118 | A | 6/1962 | Hutt | |
| 3,919,727 | A | 11/1975 | Paine | |
| 3,972,320 | A | 8/1976 | Kalman | 600/519 |
| 4,057,240 | A | 11/1977 | Damico et al. | |
| 4,087,872 | A | 5/1978 | Smirle | |
| 4,152,795 | A | 5/1979 | Rodosta et al. | |
| 4,196,425 | A | 4/1980 | Williams, Jr. et al. | |
| 4,539,560 | A | 9/1985 | Fleck et al. | |
| 4,633,237 | A | 12/1986 | Tucknott et al. | |
| 4,814,751 | A | 3/1989 | Hawkins et al. | |
| 4,837,877 | A | 6/1989 | Hamada et al. | |
| 4,907,845 | A | 3/1990 | Wood | |
| 4,947,152 | A | 8/1990 | Hodges | |
| 4,952,928 | A | 8/1990 | Carroll et al. | |
| 5,008,654 | A | 4/1991 | Callaway | |
| 5,095,560 | A | 3/1992 | Volker | |
| 5,107,845 | A | 4/1992 | Guern et al. | |
| 5,218,344 | A | 6/1993 | Ricketts | |
| 5,276,432 | A | 1/1994 | Travis | |
| 5,353,012 | A | 10/1994 | Barham et al. | |
| 5,365,217 | A | 11/1994 | Toner | |
| 5,416,695 | A | 5/1995 | Stutman et al. | 600/300 |
| 5,490,298 | A | 2/1996 | Goldsmith et al. | |
| 5,495,288 | A | 2/1996 | Broady et al. | |
| 5,519,380 | A | 5/1996 | Edwards | |
| 5,583,758 | A | 12/1996 | McIlroy et al. | |
| 5,633,627 | A | 5/1997 | Newham | |
| 5,650,770 | A | 7/1997 | Schlager et al. | |
| 5,714,931 | A | 2/1998 | Petite et al. | |
| 5,732,401 | A | 3/1998 | Conway | |
| 5,738,102 | A | 4/1998 | Lemelson | 600/483 |
| 5,740,800 | A | 4/1998 | Hendrickson et al. | |
| 5,765,139 | A | 6/1998 | Bondy | |
| 5,780,798 | A | 7/1998 | Hall-Jackson | |
| 5,781,442 | A | 7/1998 | Engleson et al. | |
| 5,831,669 | A | 11/1998 | Adrain | |
| 5,844,488 | A | 12/1998 | Musick | |
| 5,877,675 | A | 3/1999 | Rebstock et al. | |
| 5,941,836 | A | 8/1999 | Friedman | |
| 5,946,659 | A | 8/1999 | Lancelot et al. | |
| 5,953,704 | A | 9/1999 | McIlroy et al. | |
| 6,049,281 | A | 4/2000 | Osterweil | |
| 6,067,019 | A | 5/2000 | Scott | |
| 6,078,261 | A * | 6/2000 | Davsko | 340/573.4 |
| 6,104,295 | A | 8/2000 | Gaisser et al. | |
| 6,125,350 | A * | 9/2000 | Dirbas | 705/2 |
| 6,154,139 | A | 11/2000 | Heller | |
| 6,160,478 | A | 12/2000 | Jacobsen et al. | 340/539.12 |
| 6,169,484 | B1 | 1/2001 | Schuchman et al. | |
| 6,204,767 | B1 | 3/2001 | Sparks | |
| 6,259,355 | B1 | 7/2001 | Chaco et al. | |
| 6,402,691 | B1 | 6/2002 | Peddicord et al. | 600/300 |
| 6,433,690 | B2 | 8/2002 | Petelenz et al. | |
| 6,466,125 | B1 | 10/2002 | Richards et al. | |
| 6,524,239 | B1 * | 2/2003 | Reed et al. | 600/300 |
| 6,583,727 | B2 | 6/2003 | Nunome | |
| 6,611,206 | B2 | 8/2003 | Eshelman et al. | |
| 6,624,754 | B1 | 9/2003 | Hoffman et al. | |
| 6,640,212 | B1 | 10/2003 | Rosse | |
| 6,674,403 | B2 | 1/2004 | Gray et al. | |
| 6,748,250 | B1 | 6/2004 | Berman et al. | 600/310 |
| 6,753,783 | B2 | 6/2004 | Friedman et al. | |
| 6,788,206 | B1 | 9/2004 | Edwards | |
| 6,791,460 | B2 | 9/2004 | Dixon et al. | |
| 6,804,656 | B1 | 10/2004 | Rosenfeld et al. | 705/3 |
| 6,821,258 | B2 | 11/2004 | Reed et al. | |
| 6,822,571 | B2 | 11/2004 | Conway | |
| 6,830,180 | B2 | 12/2004 | Walsh | 235/385 |
| 6,838,992 | B2 | 1/2005 | Tenarvitz | |
| 6,876,303 | B2 * | 4/2005 | Reeder et al. | 340/573.1 |
| 6,897,781 | B2 | 5/2005 | Cooper et al. | |
| 6,900,732 | B2 | 5/2005 | Richards | |
| 6,909,367 | B1 | 6/2005 | Wetmore | |
| 6,915,170 | B2 | 7/2005 | Engleson et al. | |
| 6,941,239 | B2 | 9/2005 | Unuma et al. | |
| 6,958,706 | B2 | 10/2005 | Chaco et al. | |
| 6,968,294 | B2 | 11/2005 | Gutta et al. | |
| 6,975,230 | B1 | 12/2005 | Brilman | |
| 6,987,232 | B2 | 1/2006 | Smith et al. | |
| 7,001,334 | B2 | 2/2006 | Reed et al. | |
| 7,035,432 | B2 | 4/2006 | Szuba | |
| 7,110,569 | B2 | 9/2006 | Brodsky et al. | |
| 7,198,320 | B2 | 4/2007 | Rasmussen | |
| 7,242,306 | B2 * | 7/2007 | Wildman et al. | 340/573.1 |
| 7,369,680 | B2 | 5/2008 | Trajkovic et al. | |
| 7,452,336 | B2 | 11/2008 | Thompson | |
| 7,505,620 | B2 | 3/2009 | Braune et al. | |
| 2001/0044965 | A1 | 11/2001 | Blevins | |
| 2002/0046423 | A1 | 4/2002 | Vilsmeier | |
| 2002/0140559 | A1 | 10/2002 | Zhou et al. | |
| 2002/0165733 | A1 | 11/2002 | Pulkkinen et al. | |
| 2003/0013459 | A1 | 1/2003 | Rankin et al. | |
| 2003/0028399 | A1 | 2/2003 | Davis et al. | |
| 2003/0058111 | A1 | 3/2003 | Lee et al. | |
| 2003/0069815 | A1 | 4/2003 | Eisenberg et al. | |
| 2003/0167187 | A1 | 9/2003 | Bua | |
| 2003/0169171 | A1 | 9/2003 | Strubbe et al. | |
| 2004/0172290 | A1 | 9/2004 | Leven | 705/2 |
| 2004/0193449 | A1 * | 9/2004 | Wildman et al. | 705/2 |
| 2005/0125899 | A1 | 6/2005 | Hanson et al. | |
| 2005/0190062 | A1 | 9/2005 | Sullivan et al. | |
| 2005/0240086 | A1 | 10/2005 | Akay | |
| 2005/0242946 | A1 | 11/2005 | Hubbard et al. | |
| 2005/0283382 | A1 | 12/2005 | Donoghue et al. | |
| 2006/0033625 | A1 | 2/2006 | Johnson et al. | |
| 2006/0053035 | A1 | 3/2006 | Eisenberg | |
| 2006/0056655 | A1 | 3/2006 | Wen et al. | |
| 2006/0265805 | A1 | 11/2006 | Bellingroth | |
| 2007/0033072 | A1 * | 2/2007 | Bildirici | 705/3 |
| 2007/0132597 | A1 | 6/2007 | Rodgers | |
| 2007/0157385 | A1 | 7/2007 | Lemire et al. | |
| 2007/0222599 | A1 * | 9/2007 | Coveley et al. | 340/572.4 |

FOREIGN PATENT DOCUMENTS

| | | |
|---|---|---|
| EP | 141881 | 5/1985 |
| JP | 07/334579 | 12/1995 |
| JP | 04/016749 | 1/2004 |
| JP | 04/078344 | 3/2004 |
| JP | 06092147 | 4/2006 |
| WO | WO95/27467 | 10/1995 |
| WO | WO2006/011124 | 2/2006 |
| WO | 2006/117788 | 5/2006 |

OTHER PUBLICATIONS

Chang, et al., Pervasive Observation Medicine: The Application of RFID to Improve Patent Safety in Observation Unit of Hospital Emergency Department, 2005.

Exavera Technologies, Identifying . . . the Future of Healthcare, 2006.

Ho, et al., A Prototype on RFID and Sensore Networks for Elder Healthcare: Progress Report, SIGCOMM '05 Workshops, Aug. 2005.

Sangwan, et al., Using RFID Tags for Tracking Patients, Charts, and Medical Equipment Within an Integrated Health Delivery Network, 2005.

U.S. Appl. No. 11/608,074, Mail Date Mar. 1, 2009, Non-Final OA.

U.S. Appl. No. 11/608,125, Mail Date Jan. 9, 2009, Non-Final OA.

U.S. Appl. No. 11/774,471, Mail Date Dec. 23, 2008, Non-Final OA.

U.S. Appl. No. 11/779,182, Mail Date Jan. 26, 2009, Non-Final OA.

Final Office Action dated Aug. 5, 2009 cited in U.S. Appl. No. 11/779,182.

Final Office Action dated Aug. 20, 2009 cited in U.S. Appl. No. 11/608,125.

Final Office Action dated Aug. 17, 2009 cited in U.S. Appl. No. 11/608,074.

Office Action dated Sep. 15, 2009 cited in U.S. Appl. No. 11/774,471.

Office Action dated Oct. 28, 2009 cited in U.S. Appl. No. 11/561,263.

Notice of Allowance dated Mar. 8, 2010 cited in U.S. Appl. No. 11/608,125.

Office Action dated Mar. 19, 2010 cited U.S. Appl. No. 11/608,074.

Office Action dated Apr. 13, 2010 cited in U.S. Appl. No. 11/774,471.

Office Action dated May 12, 2010 cited in U.S. Appl. No. 11/561,263.
Office Action dated Jul. 7, 2010 cited in U.S. Appl. No. 11/779,182.
Notice of Allowance dated Apr. 29, 2010 cited in U.S. Appl. No. 11/608,074.

Final Office Action dated Apr. 28, 2009 cited in U.S. Appl. No. 11/774,471.

* cited by examiner

METHODS FOR REFINING PATIENT, STAFF AND VISITOR PROFILES USED IN MONITORING QUALITY AND PERFORMANCE AT A HEALTHCARE FACILITY

CROSS-REFERENCE TO RELATED APPLICATION

This application is a continuation-in-part of co-pending U.S. application Ser. No. 11/608,074, filed Dec. 7, 2006, which claims the benefit under 35 U.S.C. §119(e) of co-pending U.S. provisional application No. 60/748,376, filed Dec. 9, 2005, co-pending U.S. provisional application No. 60/799,041, filed May 10, 2006, co-pending U.S. provisional application No. 60/835,662, filed Aug. 4, 2006, and co-pending U.S. provisional application No. 60/826,634, filed Sep. 22, 2006. The disclosures of the foregoing applications are incorporated herein in their entirety.

BACKGROUND OF THE INVENTION

1. Field of the Invention

The invention is in the field of patient monitoring systems and methods for assessing and ensuring a level of quality and performance provided by a healthcare facility. The invention more particularly relates to ensuring that a healthcare facility is able to increase quality and performance based on patient specific attributes and needs embodied in individualized patient profiles, initiating appropriate responses to the patients' needs based on such profiles, and refining the patient profiles based on information gathered over time for each patient.

2. Relevant Technology

Healthcare facilities provide clinical and/or wellness health care for patients and/or residents (hereinafter collectively referred to as "patients") at such facilities. Hospitals and medical clinics provide clinical health care. Assisted living and nursing homes focus primarily on wellness health care. Most facilities provide at least some monitoring and supervision of patients to ensure they are receiving proper nutrition and medicines, are kept clean, and are protected from physical injury. A central station (e.g., a nursing station) typically functions as a primary gathering and dispatch location for caregivers. At specified intervals, or in response to a patient or resident request, a caregiver can move from the central station to a patient's location (e.g., room) and monitor or provide appropriate care.

There are often tradeoffs between ensuring that every patient at a facility receives a required level of basic care while also providing individualized care and initiating appropriate responses based on a patient's specific behaviors, attributes and needs. Even though all patients may receive the same basic level of care, some may receive too much care and others not enough care due to discrepancies between the basic standards of care and a patient's actual needs. The result is an inefficient allocation of resources that compromises the overall quality and performance of a facility and individual staff members.

There may be similar imbalances in interpreting patient behavior and fashioning appropriate responses. Not every patient behaves in the same manner, has the same health problems and issues, or requires intervention upon the occurrence of similar behaviors or events. Behavior or events that may be perfectly safe for some patients might constitute high risk to others. For example, an elderly person at a rest home who is ambulatory, requires no assistance to walk, and is known to safely walk up and down stairs without falling should not trigger caregiver intervention when approaching stairs. In contrast, caregiver intervention may be appropriate when a person who is bound to a wheel chair, who can only safely walk with assistance, or who has difficulty in perceiving or evaluating danger approaches a staircase.

One specific area of concern involves unassisted bed exiting, wheelchair exiting, wheelchair to bed transfer, or other support exiting. Unassisted support exiting by invalids or the elderly is a significant cause of injury and liability. Falls often occur due to the inability of health care facilities to provide continuous, direct supervision of patients. Unfortunately, it is typically not feasible to provide round the clock supervision of every patient due to financial and/or logistical restraints. Nevertheless, without continuous direct supervision and/or a reliable system of early notification, there may be no way for a health care provider to know when a particular patient may be engaging in support exiting or other behavior which places them at high risk for falling.

Other measurements of quality and performance involve maintaining patients within defined safety or security zones, tracking and analyzing patient gait or daily ambulation to diagnose potential injury or health issues, tracking patient contacts with assigned caregivers and/or third parties, monitoring patient socialization, initiating patient surveillance upon the occurrence of a triggering event, tracking staff movements and activities, tracking visitor movements and activities, responding to patient initiated calls or alerts, tracking assets used to provide patient care (e.g., medical devices, walkers, dentures, etc.), verifying the occurrence of prescribed treatments for each patient, and the like.

Notwithstanding the need to monitor and supervise patients to ensure an adequate level of quality and performance and prevent patient injury, the United States, Europe, Japan and other parts of the world are currently experiencing a serious shortage of nurses, nursing assistants, doctors, and other caregivers. Such shortage will only worsen with continued aging of the population. As the patient to caregiver ratio at a facility increases, the ability to provide adequate patient care and protection are likely to decrease as more patients are left unattended. There is therefore an acute need for new methods and systems that can better safeguard patients and improve the quality and performance of care delivery at a facility while also reducing facility liability, enhancing caregiver productivity, and lowering operational expenses.

Although automated patient monitoring systems have been proposed, they typically lack feasibility and have not been implemented on a wide scale. The problem with conventional patient monitoring systems is their inability to interpret and distinguish between safe or appropriate patient behaviors or conditions and those that are potentially dangerous or inappropriate as among different patients. Standard limits and alarm levels may be too tight or too loose depending on the patient. The result can be a high incidence of false positives in the case where limits and alarm levels are too tight and false negatives in the case where limits and alarm levels are too loose. A high rate of false positives can become like the boy crying wolf and might be ignored by overworked caregivers. False negatives provide no early warning of potential patient harm.

For example, one type of patient monitoring system utilizes sensors to detect patient bed exiting. A common problem that leads to a high level of false positives and false negatives is a "one size fits all" approach to detecting and interpreting patient movements. Although people often have uniquely personal ways of getting out of bed, no attempt is made in conventional monitoring systems to understand the specific movements and habits of a particular patient when bed exiting. For example, one patient might typically grasp the left handrail when commencing to bed exit while another might slide towards the foot of the bed. Persons who are left handed might exit their beds oppositely from right handed persons. Certain medical conditions might determine or alter bed exiting behavior (e.g., a person with a newly formed incision might protect against harm or pain by avoiding movements that would apply stress to the incision, even if such movements were previously used to bed exit when the patient was healthy).

In view of the foregoing, it would be an advancement in the art to provide methods and systems for monitoring patient, staff and visitor activities that can more accurately detect and interpret individual behaviors and conditions as they pertain to the overall quality and performance by a facility in delivering health care to its patients. Reducing the incidence of false positives and false negatives when detecting actionable events would be expected to increase the ability of a healthcare facility to provide an appropriate response thereto, intervene when necessary to prevent harm to a patient, and increase the overall quality and performance of the facility in providing for the specific needs of a patient as among a plurality of different patients.

SUMMARY OF THE INVENTION

The present invention relates to patient monitoring methods and systems used to ensure an appropriate level of quality provided to the patients and performance by staff and visitors at a healthcare facility. Real time data regarding the locations, movements and/or behaviors of each of a plurality of patients, caregivers, visitors and assets is obtained from multiple sources and analyzed by a computer system (e.g., facility master). The computer system meaningfully interprets the data through the use of individualized patient specific profiles in order to interpret the overall quality of service provided to each patient at a healthcare facility. In addition, the individual performance by staff and visitors, as they relate to the overall performance of the facility, can be evaluated through the use of staff and visitor specific profiles. When a patient, staff or visitor specific limit is approached or breeched, the computer system may initiate an appropriate response to prevent or mitigate patient harm, unauthorized access to restricted zones, or other inappropriate or harmful actions.

Data regarding the location, movements and/or behaviors of patients, staff, visitors and assets throughout or outside a facility can be gathered using any detection means known in the art including, but not limited to, RFID devices, an RFID detection grid, ultrasound devices, an ultrasound detection grid, GPS devices, cameras, motion detectors, light beam detectors, image analysis systems and the like. In-room surveillance cameras can be used to generate a data stream that is interpreted by a local computer system (e.g., in room controller), such as to detect movements or behaviors that may lead to unassisted support exiting by a patient. Motion and light beam detectors may also be used to detect patient, staff or visitor movements and generate data that can be analyzed by the computer system.

When a limit or alarm level is reached, a video feed from a surveillance camera may be sent to a nursing station for verification or denial by staff that a triggering event actually occurred and that a response is required to prevent or mitigate patient harm or prevent inappropriate activity. The verification or denial by staff forms an information feedback loop that can be used to refine patient, staff or visitor profiles to tighten or loosen limits or alarm levels as appropriate to more accurately identify the occurrence of triggering events in the future. Profiles can also be updated to reflect the occurrence of non-occurrence of prescribed activities, as may be automatically determined by tracking the locations of patients, staff, assets and visitors at a facility. The refinement of profiles over time allows the system to "learn" and store individualized data regarding the specific behaviors, attributes and performance of patients, staff or visitors at the facility. This reduces the instances of false positives and false negatives as it relates to detecting triggering events.

Examples of quality and performance criteria (e.g., care and wellness) include, but are not limited to, ensuring the general safety of patients (e.g., preventing and/or intervening in the case of unassisted support exiting, maintaining patients within prescribed geographic zones within or without a facility, responding to patient emergencies or alerts, and the like), assessing the status of prescribed actions (e.g., which involve caregivers, assets, patient-initiated behaviors, and the like), and assessing the status of patient's general health and well being (e.g., patient nutrition, ambulation tracking, denture use, use of walking aids, socialization, privacy, pain level, rollovers to prevent bed sores, and the like).

Many quality, performance, care and wellness parameters can be measured by tracking the location of each patient relative to the locations of caregivers, other patients, visitors, assets and/or fixed objects or locations. Certain care regimens or activities involve interactions between patients and assigned caregivers and/or assets at specified locations, often for specific durations or time intervals. Other aspects of quality and performance involve the movement of patients between certain specified locations throughout a facility, often at defined time periods. Yet others may involve interactions between multiple patients and/or patients and visitors. Individualized care and wellness parameters can be established, verified and refined through the use of specific patient profiles, sometimes in conjunction with staff and/or visitor profiles. By refining patient specific profiles based on gathered data relating to the specific behaviors and needs of each patient, the inventive systems and methods are able to interpret behaviors, conditions and events in a highly individualized manner as among different patients at a healthcare facility. Appropriate alarms, limits and prescriptions may be set for each patient as appropriate based on data contained in the patient specific profiles.

A typical patient profile includes both static and dynamic data relating to a plurality of specific care and wellness parameters. These may include, for example, limits or alarm levels relating to one or more of support exiting behavior and occurrence, patient ambulation, the use of ambulation devices, patient gait behavior, sound of patient breathing, dietary restrictions, prescribed levels of caregiver assistance for one or more activities, trips to cafeteria, assisted and/or unassisted bed turning, social interactions, prescribed patient care regimens, in-room therapy, required therapeutic devices, denture use and cleaning, bathroom time duration, facility access or movement privileges, facility exiting privileges, flight risk level, facility restricted areas, emergency call button usage, pet therapy contact, patient treatment by movement of, e.g., facility assets and/or personnel, critical medical history, and/or emergency contact information.

When a patient first enters a facility, a general patient profile of common or known patient specific behaviors may be utilized before specific information is learned about the patient through the information feedback loop. As the profile is periodically refined based on verified and/or rejected patient behaviors relative to a specific risk or activity, it becomes more accurately predictive of actual risk or behavior by the patient. That reduces the incidence of false positives and false negatives and allows for earlier intervention into the risk sequence. According to one embodiment, patient profiles having initially coarse granularity due to the lack of known patient behaviors and attributes may have increasingly fine granularity as the profiles are refined over time. Increasing profile granularity may account for idiosyncratic movements or behaviors that are entirely unique to a particular patient in addition to the commonly observed movements or behaviors common to many patients.

Profile data can be uploaded to networked or peripheral computers as needed to carry out a desired patient monitoring activity. An information feedback loop can be used to update each patient profile, which may occur automatically or manually as directed by patient and/or staff actions, in order to create and maintain a current database of patient status, attributes and needs. Actions that might be used to refine patient specific profile data include, for example, patient movements that precede support exiting, changes in patient gait, social interactions, recursive events, patient wandering or flight, use of emergency call button, sound of patient breathing, patient eating habits, observations by caregivers regarding patient behavior or condition, and patient treatment by movement of, e.g., facility assets and/or personnel. Information may be gathered for analysis by the computer system by means of RFID and/or ultrasound devices carried by patients, staff, assets, and visitors, RFID and/or ultrasound detection grids, still shot cameras, video cameras, audio recording devices, GPS devices, etc.

In the case where a triggering event is detected and verified, an alert for direct physical intervention may be sent to a staff member assigned to a particular patient or who is close to the patient and not otherwise occupied. The alert may be sent to a personal data assistant carried by each caregiver. The alerted staff member can send verification that intervention was successful. The RFID device or ultrasound device carried by the responder can also be tracked automatically to verify that intervention has occurred. Examples of triggering events include preventing unassisted support exiting, preventing patient wandering into unauthorized zones, preventing patient flight from the facility, and preventing patient abuse by caregivers, other patients or visitors.

An example of using a patient specific profile to improve patient wellness involves detecting and then preventing or mitigating potential harm caused by unassisted patient support exiting. The inventive methods and systems can be used to monitor a patient resting on a bed (e.g., standard hospital bed with side rails), wheelchair, gurney, couch, chair, or recliner, to which the patient may be confined and detect movements or behaviors that are predictive of support exiting. Monitoring may be performed by one or more cameras, motion sensors, small zone RFID, ultrasound, and/or light beam detectors. A computer system analyzes a data stream and detects movements or behaviors that are predictive of support exiting. The use of patient specific profiles helps the computer system distinguish between movements that are predictive of support exiting and movements that are not.

If behavior predictive of support exiting by a patient is detected, an appropriate response is triggered, examples of which include one or more of alerting staff, establishing two-way audio-video communication between staff and the patient, sending prerecorded audio and/or video warnings to the patient's room, direct intervention by a staff member, and automated functions, such as bed lowering, raising a bedrail, turning on a light, or actuation of a patient restraint device. Similar algorithms involving analysis of video data streams can be used to detect other movements by a patient such as patient rollover (e.g., to prevent skin damage), movements indicative of disease, movements consistent with prescribed behaviors, and the like.

An information feedback loop provided by a system of cameras and monitors permits human inspection and verification of patient support exiting before initiating audio, visual and/or physical intervention. A video feed of the patient is sent to a monitor at a central station (e.g., nursing station) subsequent to a visual and/or aural alert to both the nursing station and the patient's room. A staff member views the live video stream from the patient's room to determine if the patient is actually attempting to exit the support. If so, verification is provided to the computer system by the staff member and appropriate intervention to prevent or assist support exiting is initiated. If not, rejection is provided to the computer system. If no response to the alert is given within a prescribe time period, an automated response may be initiated, such as sending a pre-recorded message or warning to the patient and/or alerting nearby staff for direct physical intervention.

The information feedback loop can also be used to update a patient profile to better predict future support exiting. The action of verifying or rejecting an automated support exiting alert based on actual patient movements and behavior can be recorded by the computer system and used to refine the patient profile (e.g., tightening or loosening limits) in order to better predict future support existing. The information feedback loop can also be used to refine other limits or data in the patient profile. For example, if the monitoring system detects patient movements that may be indicative of flight from the facility, wandering into unauthorized zones, or substantial changes in patient gait, an alert may be triggered and a video feed of the patient sent to a central nurse's station. Two-way communication can also be established to determine the patient's actual intentions or needs. Based on actual patient behavior, limits can be tightened or loosened to better predict patient flight risk, wandering, or health issues relating to gait.

In the case where a video data stream is generated by a surveillance camera, such as to detect support exiting or other high risk patient behavior, it is typically deleted on an ongoing basis to protect patient privacy. If the video stream is made available for viewing (e.g., by being sent to a nursing station), an alert is sent to the patient to notify of potential third party viewing to protect privacy (e.g., by means of a chime, recording, visual display of words, etc.). In some cases, the video data stream may be optionally archived (e.g., recorded on a non-volatile recording medium) for later viewing and analysis of an event. The archived video can be used to assess the overall quality and performance of a healthcare facility. Events that might trigger video archiving include entry into the patient's room or personal space by staff, visitors or other patients, manual alerts or distress signals sent by a patient, detection of other dangerous conditions (e.g., alterations of vital signs), and requested archiving by visiting relatives, friends, doctors or other health care providers.

The location of patients can be continuously tracked by means of an assigned RFID device or ultrasound device worn or carried by each patient that emits a signal that can be detected and traced to a specific location by a corresponding RFID sensor grid or ultrasound sensor grid respectively. RFID devices and ultrasound devices may include an alert device that can be activated in case of emergency of other urgent need. Because an RFID device or ultrasound device also provides means for locating the patient, assistance can be provided quickly even if the patient cannot communicate. Two-way audio-visual communication may be initiated via a camera, video monitor, microphone and speaker. The alerting system may access the patient's profile in order to tailor the response to specific patient needs. Patient usage of the alert feature can be tracked, analyzed and used to update the patient's profile. For example, a patient profile may include data relating to proper and/or improper usage of the patient alert button.

In summary, computer controlled methods and systems can be used for monitoring the location and/or activities of patients, staff, assets and visitors and as they relate to prescribed care and wellness, responding to actionable events, verifying wellness events, maintaining and updating patient, staff and visitor profiles, preventing or mitigating patient injury, locating and assisting patients in need of assistance, and monitoring and archiving video information relating to potentially dangerous activities.

These and other advantages and features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE PREFERRED EMBODIMENTS

I. Introduction

Figure 1:
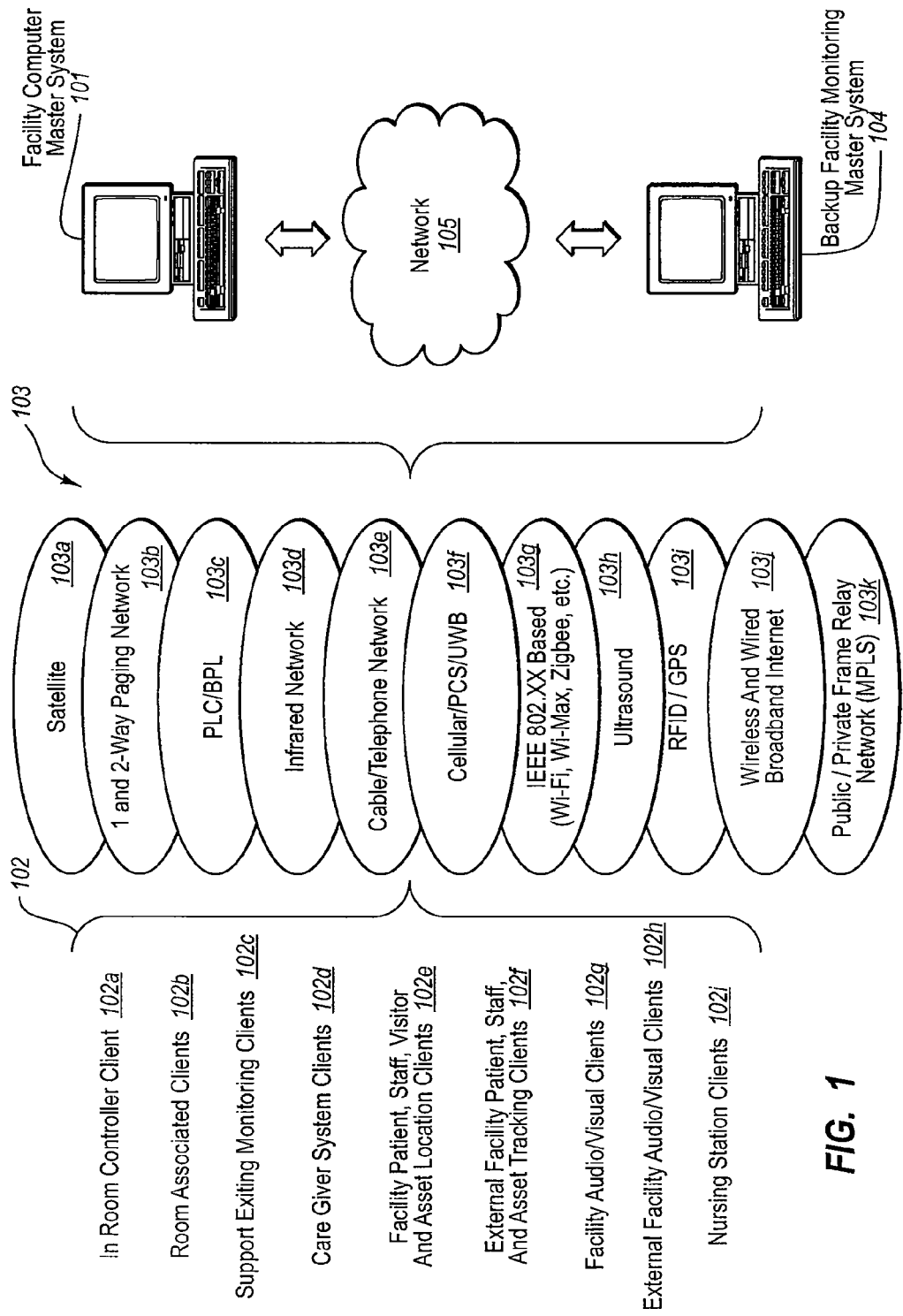
FIG. 1 schematically illustrates various exemplary computer-client network protocols that can be used to facilitate communication between a facility master computer system and peripheral clients.

Embodiments of the present invention extend to methods, systems, and computer program products for managing quality of care and performance by staff and visitors at a healthcare facility. The invention more particularly relates to computer-controlled methods and systems for monitoring a plurality of patients, staff, assets and visitors at the facility using electronic devices, computers, patient profiles, staff profiles, visitor profiles, algorithms, human verification of triggering events, and direct human intervention to provide improved quality of care and performance based on each patient's general and individualized needs.

Patient specific data can be collected for each patient to create a database of generalized and personalized knowledge. Healthcare facilities and providers can use the database of knowledge to better understand risks associated with various activities for each patient and/or for each type of activity. Predictive modeling and artificial intelligence can be applied to collected data patterns to identify, process, categorize, alarm, and rectify risks based on patient information, such as, for example, patient type, patient activity, patient medications, patient physical therapy process, patient location, and other variables.

The quality and performance monitoring systems and methods of the invention assist caregivers at a facility in ensuring and verifying that each patient at the facility receives a prescribed level of care and also helps ensure wellness for each of a plurality of patients based on one or more predetermined wellness criteria. To be sure, there are general aspects and levels of patient care and wellness that may be substantially similar for some or all patients, including the need for adequate rest, nutrition, cleanliness, safety, privacy, and the like. On the other hand, some or all patients may require specialized care and have different wellness criteria based on individual patient needs (e.g., based on age, physical capacity, mental capacity, and the like).

The quality and performance systems and methods of the invention monitor care and wellness for each patient by means of automated tracking of patients, caregivers and assets used to deliver care, and visitors. The inventive methods and systems track patient location, activities, condition, and regimen completion, as well as assigned caregiver and asset location, activities and regimen completion. Care and wellness are measured in relation to individual patient profiles which are maintained and periodically refined for each patient. The quality and performance of staff and visitors can also be monitored and assessed using staff and visitor profiles. According to one embodiment, the methods and system initiate responses to pre-determined triggering events to prevent or mitigate patient harm.

The methods and systems are implemented using a computer-controlled electronic patient monitoring system that receives and analyzes data generated by a network of electronic data generating devices. A profile maintenance and refinement sub-system and method is used to periodically update and refine patient, staff and visitor profiles as data is received and analyzed for individual patients, staff and visitors. The care and wellness of a patient, as well as the performance of staff and visitors, can be analyzed and improved through the use of individually refined profiles.

The term "patient profile" shall refer to stored data that is associated with a specific patient at a health facility. Patient profiles typically include static data and dynamic data. Dynamic data refers to limits and alarms that are continuously or periodically updated or refined based on information learned about the patient and/or changing patient needs or requirements. Dynamic data can be automatically updated in response to events or it may be manually updated by staff after an event.

The terms "care" and "wellness" shall be broadly understood to cover every aspect of a patient's life and well being that are relevant to care and treatment at a health facility. Care more particularly relates to treatments, activities and regimens that are provided to the patient in order to ensure a prescribed or minimum level of general health and well-being. Wellness is a measure of the general health and well-being of the patient. Care and wellness affect the overall quality and performance of a healthcare facility.

The term "patient fall" shall be broadly understood to include falling to the ground or floor, falling into stationary or moving objects, falling back onto a support, or any other falling motion caused at least in part by gravity that may potentially cause physical injury and/or mental or emotional trauma.

The terms "rest" and "resting" as it relates to a patient resting on a support shall be broadly understood as any situation where the support provides at least some counter action to the force of gravity. Thus, a patient may "rest" on a support while lying still, sitting up, moving, lying down, or otherwise positioned relative to the support so long as the support acts in some way to separate a patient from the floor or surface upon which the support is itself positioned.

The terms "continuous monitoring" and "continuous video data stream" include taking a series of images that may be spaced apart by any appropriate time interval so long as the time interval is sufficiently short that the system is not unduly hampered from initiating a response in time to prevent or mitigate a potentially dangerous event.

The terms "receiving" and "inputting" in the context of a patient profile broadly includes any action by which a complete or partial patient profile, or any component thereof, is stored or entered into a computer system. This includes, but is not limited to, creating a profile and then storing or entering it into a computer, entering data which is used by the computer to generate a new patient profile, and/or storing or entering data used by a computer for updating a pre-existing patient profile already in the computer.

Those skilled in the art will appreciate that the invention may be practiced in network computing environments with many types of computer system and electronic device configurations, including, personal computers, desktop computers, laptop computers, hand-held devices, multi-processor systems, microprocessor-based or programmable consumer electronics, network PCs, minicomputers, mainframe computers, mobile telephones, PDAs, one-way and two-way pagers, Radio Frequency Identification ("RFID") devices (e.g., bracelets, tags, etc.), ultrasound devices (e.g., bracelets, tags, etc.), global position ("GPS") devices, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present invention may comprise or utilize a special purpose or general-purpose computer including computer hardware, as discussed in greater detail below. Embodiments within the scope of the present invention also include physical and other computer-readable media for carrying or having computer-executable instructions or data structures stored thereon. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, computer-readable media can comprise physical storage media or transmission media.

Physical storage media, such as, RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can comprise a network or data links which can be used to carry or store desired program code means in the form of computer-executable instructions or data structures and which can be accessed by a general purpose or special purpose computer. Combinations of the above should also be included within the scope of computer-readable media.

Further, it should be understood, that upon reaching various computer system components program code means in the form of computer-executable instructions or data structures can be transferred automatically from transmission media to physical storage media. For example, computer-executable instructions or data structures received over a network or data link can be buffered in RAM within a network interface card, and then eventually transferred to computer system RAM and/or to less volatile physical storage media at a computer system. Thus, it should be understood that physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

II. Computer-Implemented Electronic Patient Monitoring System and Method for Measuring and Verifying Quality and Performance A. Exemplary System Architecture According to one currently preferred embodiment, the quality and performance monitoring systems and methods of the inventions are implemented by means of a computer system. The computer system may include one or more centralized computers, referred to as a "facility master", and one or more localized computers, exemplified by one or more "in room controllers". The various computers within the overall computer system divide up the task of receiving and analyzing data gathered from the overall patient monitoring system. FIG. 1 schematically illustrates the relationship between various components of an exemplary computerized system that can assist in monitoring the location, behavior and attributes of a plurality of patients, staff, assets and visitors at a healthcare facility.

As seen in FIG. 1, a facility master computer system 101 receives data regarding patients, staff, visitors and assets from a variety of data collection clients 102 within and outside a facility. These include, for example, in room controller clients 102a, room associated clients 102b, support exiting monitoring clients 102c, care giver system clients 102d, facility patient, staff, visitor and asset tracking and location clients 102e, external facility patient, staff and asset tracking clients 102f, facility audio/visual clients 102g, external facility audio/visual clients 102h, and nursing station clients 102i. The data gathered or generated by the data collection clients 102 is sent to the facility master computer system 101 by means of communication pathways 103 for analysis, response, and report. In some cases, a localized computer, such as an in room controller client and/or nursing station client 102i, may perform its own analysis of gathered data in order to compartmentalize or bifurcate the tasks provided by the various computers of the computer system in order to more efficiently use the computer system resources and reduce bottle necks.

The communication pathways 103 used to communicate gathered data from clients 102 to facility master computer 101 are exemplified by satellite 103a, paging network 103b, PLC/BPL 103c, infrared network 103d, cable/telephone network 103e, cellular/PCS/UWB system 103f, IEEE 802.xx wireless 103g (e.g., Wi-Fi, Wi-Max, Zigbee, etc.), ultrasound 103h, RFID/GPS 103i, wireless and wired broadband Internet 103j, and public/private frame relay network 103k (e.g., MPLS). According to one embodiment, data from facility master computer 101 can be periodically archived and/or analyzed at a backup facility monitoring master system 104 (e.g., via network 105).

Figure 2:
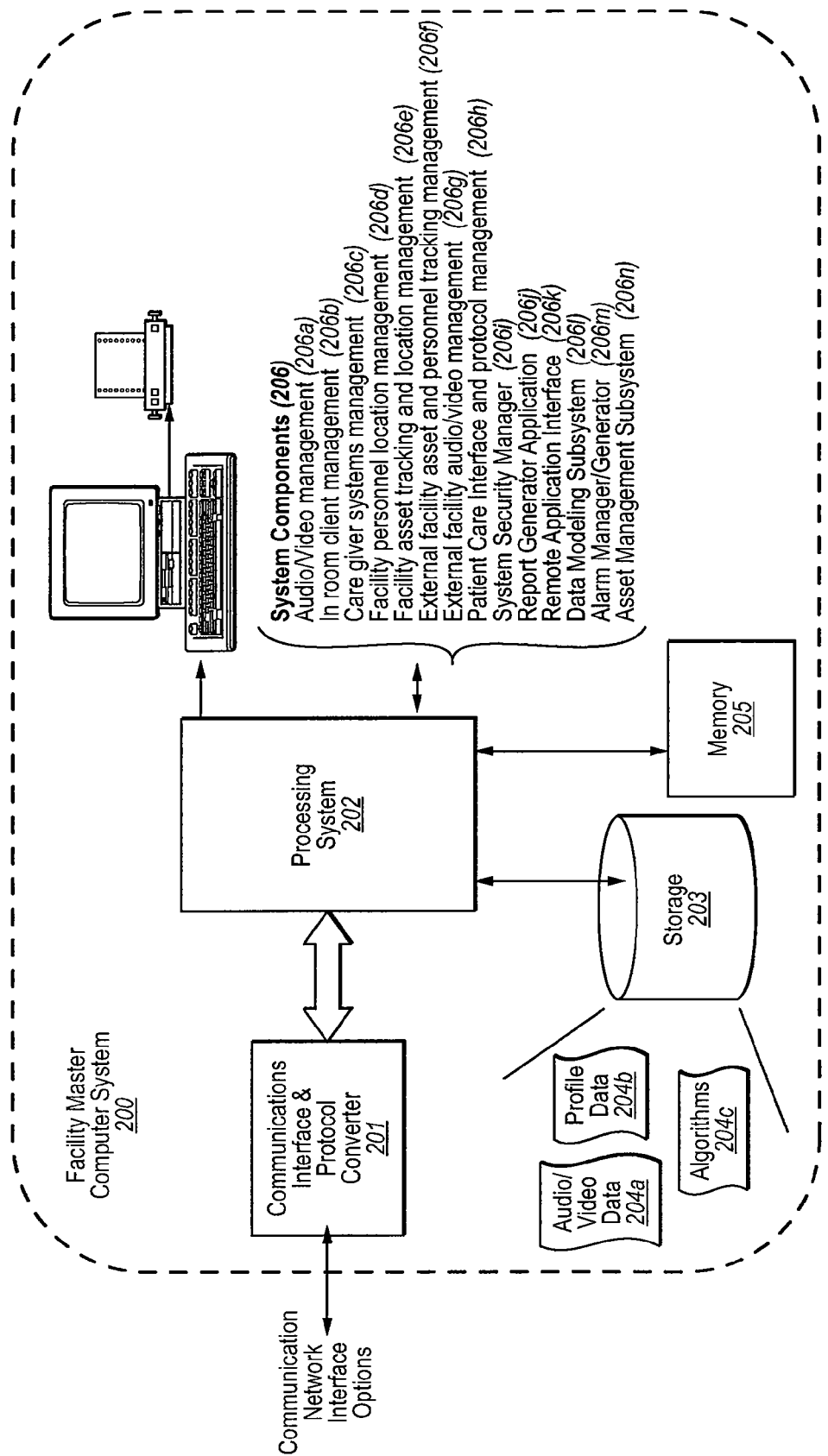
FIG. 2 schematically illustrates an exemplary facility monitoring master system.

FIG. 2 schematically illustrates an exemplary facility master computer system 200 that can be used to control and implement quality and performance monitoring systems and methods according to the invention. Communications interface and protocol converter 201 can receive communications in accordance with one of the various protocols of FIG. 1 and can convert the communication so as to be compatible with a processing system 202. Storage 203 can store data used and produced by the processing system 202, examples of which include archived audio/video data 204a (e.g., archived in response to detection of an actionable event), profile data 204b (e.g., patient, staff and visitor data), and algorithms 204c used to process data and initiate appropriate responses and reports. Memory 205 can be used to buffer and quickly access short term data used or generated by the processing system 201.

The facility master computer system 200 includes exemplary system components 206, which are modules or applications that process data gathered by data collection and processing devices (e.g., clients 102 of FIG. 1). Some of these modules or applications can also be run, at least in part, by local computers, such as in room controller clients (not shown). These include audio/video management 206a, in room client management 206b, care giver systems management 206c, facility personnel location management 206d, facility asset tracking and location management 206e, external facility asset and personnel tracking management 206f, external facility audio/video management 206g, patient care interface and protocol management 206h, system security manager 206i, report generator manager 206j, remote application interface 206k, data modeling subsystem 206i, alarm manager/generator 206m, and asset management subsystem 206n.

Figure 3:
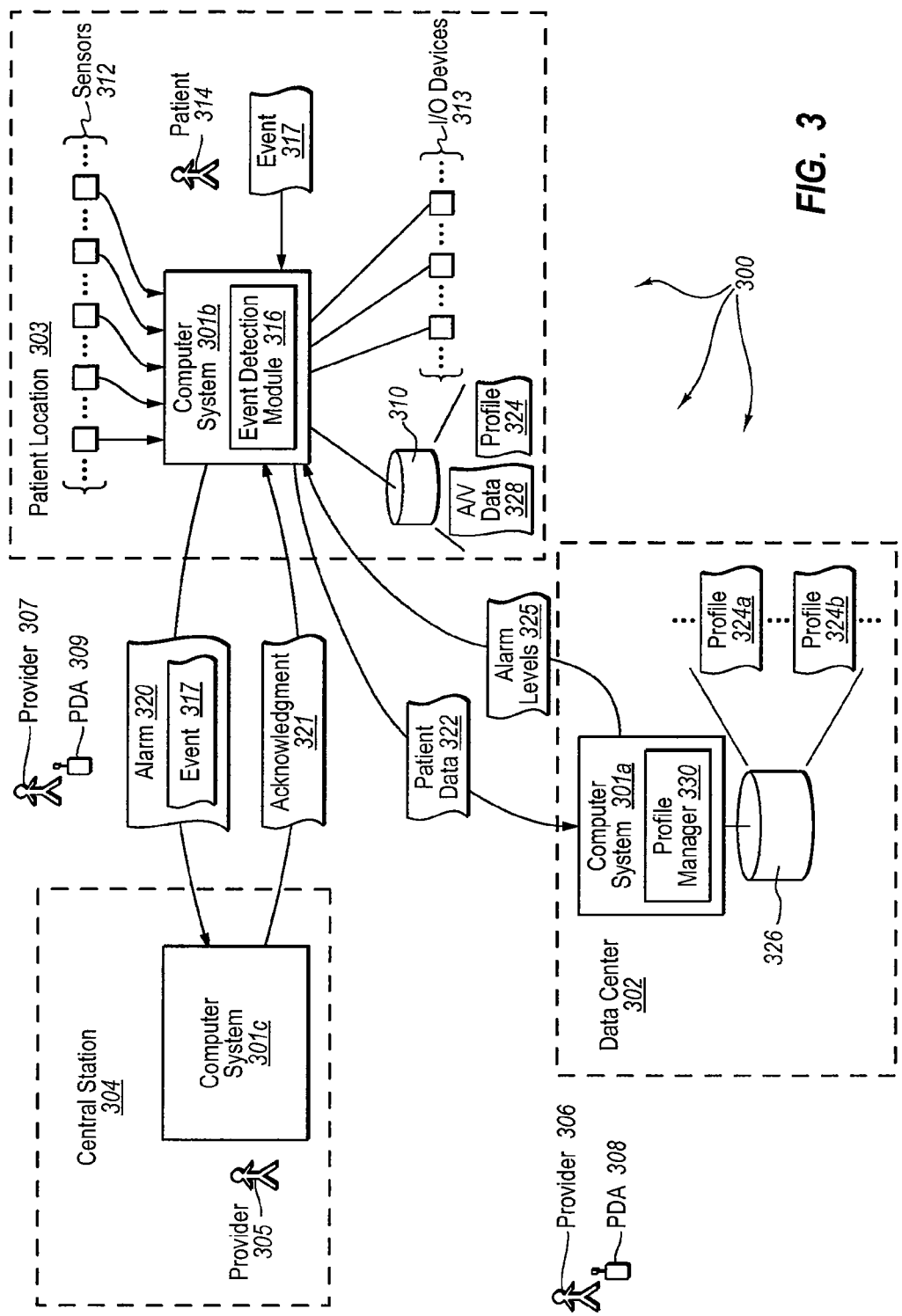
FIG. 3 schematically illustrates exemplary computer architecture that facilitates facility, patient, staff and/or asset monitoring and event response management.

FIG. 3 illustrates an exemplary computer-implement monitoring system 300 that monitors patients, staff, assets and visitors, assesses quality and performance, and manages event responses at a healthcare facility. Monitoring system 300 includes a networked computer system 301, which is composed of a main computer system 301a (e.g., facility master) located in a data center 302, first peripheral computer system 301b (e.g., in room controller client) at patient location 303, and second peripheral computer system 301c at a central station (e.g., nurse's station). The use of an in room controller computer to analyze data regarding a patient within a patient room is more particularly illustrated in FIGS. 10A and 10B, which are discussed more fully below. Each computer system 301a-c can be connected to a network, such as, for example, a Local Area Network ("LAN"), a Wide Area Network ("WAN"), or even the Internet. The various components can receive and send data to each other, as well as other components connected to the network. Networked computer systems constitute a "computer system" for purposes of this disclosure.

Networks facilitating communication between computer systems and other electronic devices can utilize any of a wide range of (potentially interoperating) protocols including, but not limited to, the IEEE 802 suite of wireless protocols, Radio Frequency Identification ("RFID") protocols, ultrasound protocols, infrared protocols, cellular protocols, one-way and two-way wireless paging protocols, Global Positioning System ("GPS") protocols, wired and wireless broadband protocols, ultra-wideband "mesh" protocols, etc. Accordingly, computer systems and other devices can create message related data and exchange message related data (e.g., Internet Protocol ("IP") datagrams and other higher layer protocols that utilize IP datagrams, such as, Transmission Control Protocol ("TCP"), Remote Desktop Protocol ("RDP"), Hypertext Transfer Protocol ("HTTP"), Simple Mail Transfer Protocol ("SMTP"), etc.) over the network.

In some embodiments, a multi-platform, multi-network, multi-protocol, wireless and wired network architecture is utilized to monitor patient, staff, visitor, and asset locations and movements within a facility. Computer systems and electronic devices may be configured to utilize protocols that are appropriate based on corresponding computer system and electronic device on functionality. For example, an electronic device that is to send small amounts of data a short distance within a patient's room can be configured to use Infrared protocols. On the other hand, a computer system configured to transmit and receive large database records can be configured to use an 802.11 protocol. Components within the architecture can be configured to convert between various protocols to facilitate compatible communication. Computer systems and electronic devices may be configured with multiple protocols and use different protocols to implement different functionality. For example, an in room controller or other computer system 301b at patient location 303 can receive patient data via infrared from a biometric monitor and then forward the patient data via fast Ethernet to computer system 301a at data center 302 for processing.

In some environments, ultrasound technologies, such as, for example, those developed by Sonitor Technologies, may be preferred for monitoring patient, staff, and asset locations, movements, and interactions within a facility. Ultrasound waves can be blocked by normal walls, are less likely to reflect off of metallic objects, and are less likely to interfere with sensate instruments. For example, ultrasound waves can be confined to a room (e.g., a patient room) where they originate. When using ultrasound receivers and detectors, various Digital Signal Processing (DSP) algorithms can be used to convert ultrasound waves into meaningful digital data (e.g., for transport on a wired network). The DSP algorithms can be configured to ensure that ultrasound detectors interpret ultrasound waves without risk of interference from any environmental noise or other signals nor interference with sensitive instruments.

However, in other environments the increased range of RFID may be preferred for monitoring patient, staff, and asset locations, movements, and interactions within a facility. For example, since RFID signals can pass through walls, RFID detection systems can be implemented with fewer detectors.

Computer system 301c can be physically located at a central station 304 of a healthcare facility, e.g., a nursing station. Provider 305 (a nurse or other healthcare worker) can be physically located near computer system 301c such that provider 305 can access electronic communications (e.g., alarm 320, video feeds, A/V communications) presented at computer system 301c. Acknowledgment 321 can be sent to other computer systems 301a, 301b as appropriate to verify that alarm 320 was considered by provider 305. Other healthcare providers, such as providers 306 and 307, can be physically located in other parts of a healthcare facility. Healthcare providers can move between different locations (e.g., central station 304, patient rooms, hallways, outside the building, etc.). Accordingly, healthcare providers 306, 307 can also carry mobile computer systems (e.g., laptop computers or PDAs 308 and 309) and other types of mobile devices, (e.g., pagers, mobile phones, GPS devices, ultrasound, or RFID devices). As providers 306, 307 move about a healthcare facility they can still access electronic messages (e.g., alarms) and send messages.

Computer system 301b, storage device 310, sensors 312, and I/O devices 313 can be physically located at patient location 303, such as patient rooms, common areas, hallways, and other appropriate locations throughout or outside a healthcare facility. For example, patient location 303 can be a room of a patient 314. Sensors 312 can include various types of sensors, such as, for example, video cameras, still cameras, microphones, motion sensors, pain scale sensors, pressure sensors, acoustic sensors, temperature sensors, heart rate monitors, conductivity sensors, RFID detectors, ultrasound detectors, global positioning sensors ("GPS"), manual assistance switches/buttons, bed sensors, handrail sensors, mattress sensors, location sensors, oxygen tank sensors, support location sensors, call buttons, etc. Although depicted separately, I/O devices 313 can also be sensors. Sensors and I/O devices can also send data to any appropriate computer system for processing and event detection, including either or both of computer systems 301a and 301c.

Some sensors 312 can be stationary (e.g., mounted at patient location 303) such that the sensors sense patient, staff, asset or visitor characteristics when within a specified vicinity of the sensor 312. For example, characteristics of a patient's gait can be observed when the patient walks by a video camera or closely spaced apart location sensors. A patient's gait can be monitored by measuring the time it takes a patient to move between localized points or zones. Other sensors can be mobile and move with a patient, provider, asset or visitor as they move about a healthcare facility. For example, a heart rate monitor can be attached to a patient and move with the patient to continuously monitor the patient's heart rate. As a patient, provider, asset or visitor moves about a healthcare facility, different combinations of stationary and mobile sensors can monitor the patient, provider, asset or visitor at different locations and/or times.

Each of sensors 312 can provide input to computer system 301b. Event detection module 316 can monitor and process inputs from sensors 312 to detect if a combination of inputs indicates the occurrence of a potentially actionable event 317. Detecting the occurrence of event 317 can trigger the transfer of various electronic messages from computer system 301b to other networked computers of the monitoring system 300. For example, electronic messages (alarm messages 320 regarding event 317) can be transferred to computer system 301c and/or mobile devices to alert health care providers of an actionable event 317. Alternatively or in addition, electronic messages including patient data 322 can be transferred to other computer systems, such as computer system 301a, that process the patient data 322 (e.g., for refining patient profiles 324 stored in storage 326). Alarm levels 325 can be sent to computer system 301b for use in determining whether an event 317 is actionable.

One or more of sensors 312 can be used to detect patient conditions or performance, such as support exiting, ambulation, changes in gait, social interaction, breathing, etc. RFID zones or ultrasound zones separated by specified distances can be used to measure total ambulation distances and monitor speed or interruptions in speed as a patient walks. Image analysis can determine the manner of a patient's walk and/or support exiting. Computer system 301b can buffer sensor input at storage device 310 for some amount of time before discarding the input (e.g., video data). In response to detecting the occurrence of an event 317, computer system 301b can locally archive sensor input or data from I/O devices 908 at storage device 310 (e.g., A/V data 328). Buffered and/or archived sensor input can provide the basis for patient data 322 that is transferred to other computer systems.

Event occurrences can be detected in accordance with a risk profile associated with a monitored patient. Patient profiles 324, either accessed directly from computer system 301a or stored locally in storage 310, can be used to analyze data from sensors 312. Alternatively, alarm levels 325 can be used independently of a patient profile 324 by local computer system 301b. Based on differing patient profiles 324 and/or alarm levels 325 for a plurality of patients, a combination of inputs detected as the occurrence of an (actionable) event 317 for one patient is not necessarily detected as the occurrence of an (actionable) event 317 for another patient, and vice versa. An actionable event can be detected when a specified alarm level for a given patient is satisfied. For example, a specified combination of risk behaviors and/or vital signs can cause an actionable event to be detected.

Computer system 301a and storage device 326 can be physically located at data center 302. Storage device 326 can store profiles (e.g., profiles 324a and 324b) for patients, staff and visitors. Profile manager 330 can receive patient data 322 sent to computer system 301a (e.g., in response to a detected event) and refine a corresponding patient profile 324 in accordance with the patient data 322. As data related to a patient 314 changes, the patient's profile 324 can be modified to indicate changed risks, limits and alarm levels for the patient 314. Risk profiles for a patient can be iteratively refined as patient data 322 for the patient 314 is received. Algorithms for refining profiles can be recursed on a per iteration basis.

Patients, providers, visitors and assets may carry RFID transmitting devices, which are examples of a sensor 312, each having a unique signature such that an RFID transmitting device can be used to determine the location of a patient, provider, visitor or asset within a healthcare facility. RFID transmitting devices can be non-removable, such as a bracelet or an adhesively attached pad, or removable, such as an employee badge.

Alternately, patients, providers, and assets may carry ultrasound transmitting devices that can be used to determine patient, provider and asset locations within a healthcare facility. Transmitted ultrasound waves can be detected by ultrasound receivers.

B. Event Response

Appropriate responses to an alert or alarm of an event can be provided through communication among and between computer systems. The difference between an alert and alarm is one of severity. If a trigger is minimally exceeded, an alert is activated. Typical alert responses include notification of event to the nursing station, establishment of A/V contact with patient, sounding of a tone, or verbally dispatching staff to investigate the situation. Significantly exceeding trigger value or ignored alerts will generate alarms, which typically activate an automatic PDA dispatching of staff, A/V contact and report generation.

Figure 4:
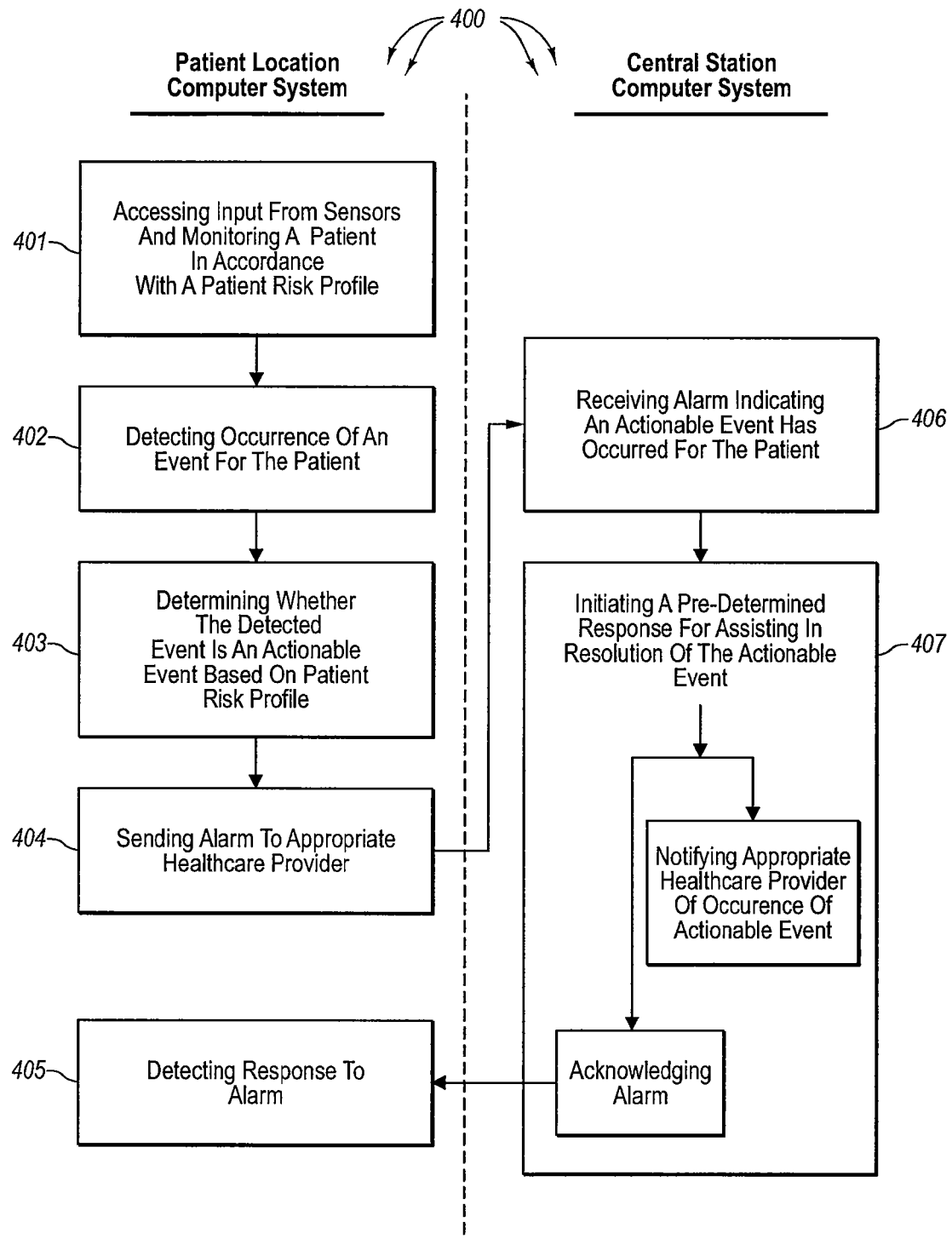
FIG. 4 is a flow chart that illustrates an exemplary method for managing a response to an actionable event in a healthcare facility.

FIG. 4 illustrates a flow chart of a method 400 for managing a response to an actionable event in a healthcare facility. Method 400 will be described with respect to the components and data in monitoring system 300 of FIG. 3. Method 400 includes an act 401 of accessing input from sensors monitoring a patient in accordance with a patient risk profile 324. Further discussion regarding patient profiles is set forth later.

Method 400 further includes an act 402 of detecting the occurrence of a patient related event. For example, event detection module 316 can detect the occurrence of event 317 for patient 314 (from the input of one or more of sensors 312). Thereafter, an act 403 involves determining whether the detected event is an actionable event based on a patient risk profile 324 and/or alarm level 325. Profile manager 330 can create alarm levels 325 which are sent to event detection module 316 of computer system 301b. Alarm levels 325 can include one or more combinations of values for inputs from sensors 312 that indicate an actionable event based on profile 324. When one or more monitored values satisfy an alarm level 325, an actionable event is detected.

Method 400 includes an act 404 of sending an alarm to an appropriate healthcare provider. For example, computer system 301b can send an alarm 320, including event 317, to computer system 301c to communicate the occurrence of event 317 to healthcare provider 305. Thereafter, act 406 involves receiving an alarm indicating an actionable event has occurred for the patient. For example, computer system 301c can receive alarm 320 indicating that event 317 (an actionable event) has occurred for patient 314 in accordance with profile 324 and/or alarm level 325.

Method 400 includes an act 407 of initiating a pre-determined response for assisting in the resolution of the actionable event. For example, computer system 301c can initiate a predetermined response for assisting in resolution of event 317 in response to receiving alarm 320. A response can include notifying an appropriate health care provider 306, 307 of the occurrence of the actionable event 317. For example, in response to receiving alarm 320, computer system 301c can present an audio and/or video indication of event 317 at central station 304, such as by means of a video display and speakers. Alternately, or in addition, one or more of PDAs 308, 309 can receive alarm 320 and present an audio and/or video indication of event 317 to providers either or both of providers 306, 307.

Initiating a response 407 can include acknowledging the alarm. For example, computer system 301c can send acknowledgment 321 to either or both of computer systems 301a, 301b. Sending acknowledgment 321 may result in establishing one or two-way communication between a healthcare provider and patient location 303 (e.g., using I/O devices 313). For example, provider 305 can input commands at computer system 301c to open communication from central station 304 to patient location 303. Similarly, providers 306, 307 can input commands at PDA's 308, 309 to open communication from their locations to patient location 303. Communication can be used to send instructions to a patient, ascertain whether a patient is coherent, responsive to commands or instructions, etc.

A response 407 can also include a provider responding to the location of a patient. For example, in response to detecting that patient 314 has fallen, might fall, or otherwise requires assistance (e.g., by a patient controlled call device), provider 306 or 307 can respond to patient location 303. RFID detectors and/or ultrasound detectors at patient location 303 can detect an RFID transmitting device and/or ultrasound transmitting device respectively corresponding to provider 306 or 307 to verify response by provider 306 or 307 to a patient in need (e.g., comprising act 405 of method 400).

Expiration of a time interval can trigger some actionable events. For example, movement of bed bound patients to prevent bed sores or administration of medicine can be required at specified intervals. Computer system 301b can send an alert to computer system 301c (or other appropriate computer systems) when a time interval expires or is about to expire.

C. Refining Patient Risk Profiles and Modifying Alarm Levels

Figure 5:
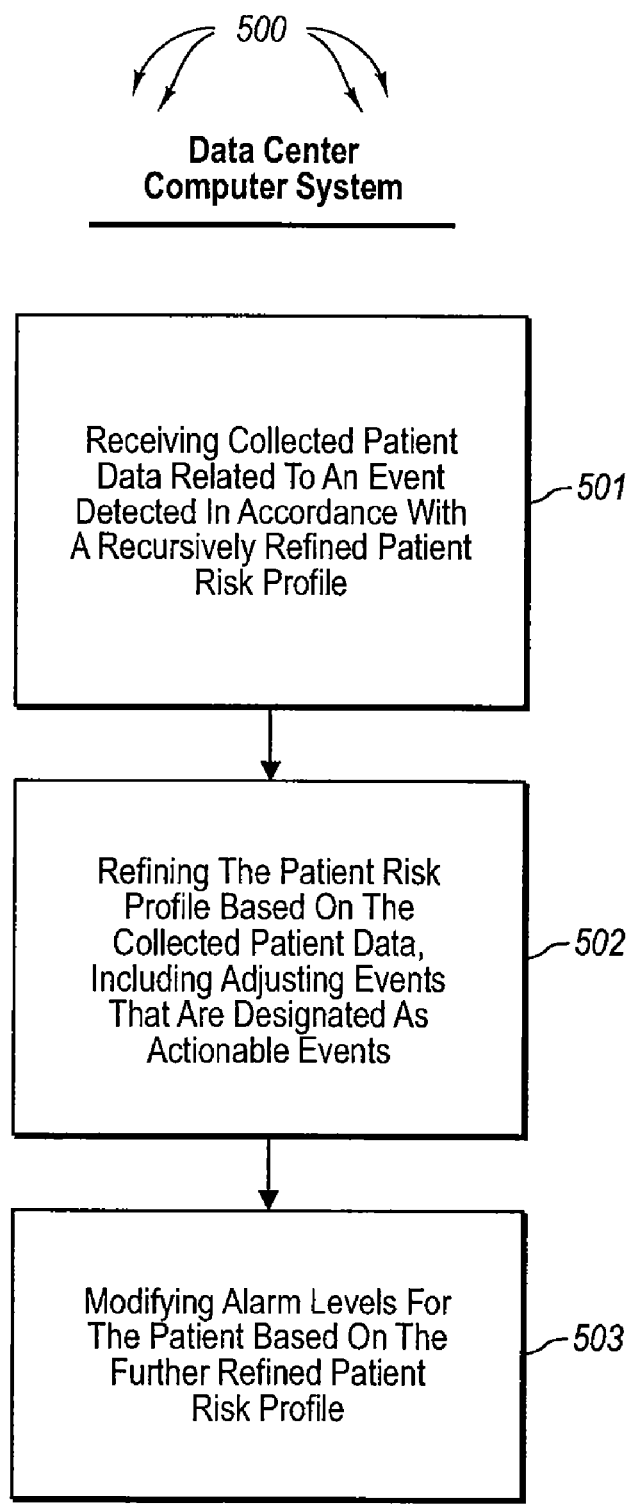
FIG. 5 is a flow chart that illustrates an exemplary method for maintaining alarm levels in a patient risk profile for a patient of a healthcare facility.

In some embodiments, stored patient profiles include risk profiles that include recursively refined patient alarms levels indicative of actionable events requiring a response. FIG. 5 is a flow chart that illustrates a computerized method 500 for maintaining and refining patient risk profiles and associated alarms levels for a patient at a healthcare facility. Method 500 will be described with respect to the components and data in monitoring system 300. Method 500 includes an act 501 of receiving collected patient data 322 related to a detected event 317 for a patient 314. For example, computer system 301a can receive patient data 322 related to event 317 for patient 314.

As previously described, event 317 can be detected in accordance with a recursively refined risk profile 324 based on previously collected patient data for patient 314 (or on historical default data). Patient data 322 is collected from a plurality of sensors 312 monitoring the patient 314 for various conditions that, when combined or considered individually, indicate occurrence of an event 317. Although event 317 may be an actionable event, embodiments of the invention can also receive data in response to non-actionable events 317. For example, some events 317 may trigger refinement of a patient risk profile 324 without triggering an alarm 320.

Method 500 includes an act 502 of refining the patient risk profile 324 based on the collected patient data 322. For example, profile manager 330 can refine patient risk profile 324 based on patient data 322. Profile manager 330 can adjust events 317 that are designated as actionable events for patient 314. Profile manager 330 can iteratively refine profile 324 through recursive application of profile refinement algorithms.

Act 503 involves modifying alarm levels 325 for the patient 314 based on the further refined patient risk profile 324 such that an appropriate health care response can be provided for alarms indicative of actionable events. For example, profile manager 330 can adjust alarm levels 325 for patient 314 based on refinements resulting from patient data 322. Alarm levels 325 can cause an appropriate healthcare provider to be notified when actionable events related to patient 314 occur. Modified alarm levels can differ from previous alarm levels for patient 314 as a result of refinements to profile 324 to adjust risk. In some embodiments, an information feedback loop can be used to periodically or continually update patient profiles to fine tune the monitoring of patient conditions. For example, monitoring for bed exiting can begin with common preset values that are updated over time to create unique or verified information for each patient.

A decision algorithm can be used to adjust parameter values that will cause an actionable event. If an actionable event is appropriately detected (a positive), parameters can be made more restrictive such that the standard is lowered for detecting the actionable event in the future. For example, if a patient has fallen when exiting a bed, the values for detecting a bed exit can be made more restrictive. On the other hand, if an actionable event is inappropriately detected (a false positive), parameters can be made less restrictive such that the standard is raised for causing or detecting the actionable event in the future. When no actionable event is detected (a negative) for some time period, the parameters can also be made less restrictive such that the standard is raised for causing or detecting the actionable event in the future.

D. Measuring Care and Wellness

Patient care and wellness can be monitored in a variety of ways. According to one embodiment, appropriate care and wellness according to certain parameters can be determined by monitoring the locations and/or movement of patients relative to one or more of caregivers, assets, visitors, other patients or fixed locations.

Figure 6:
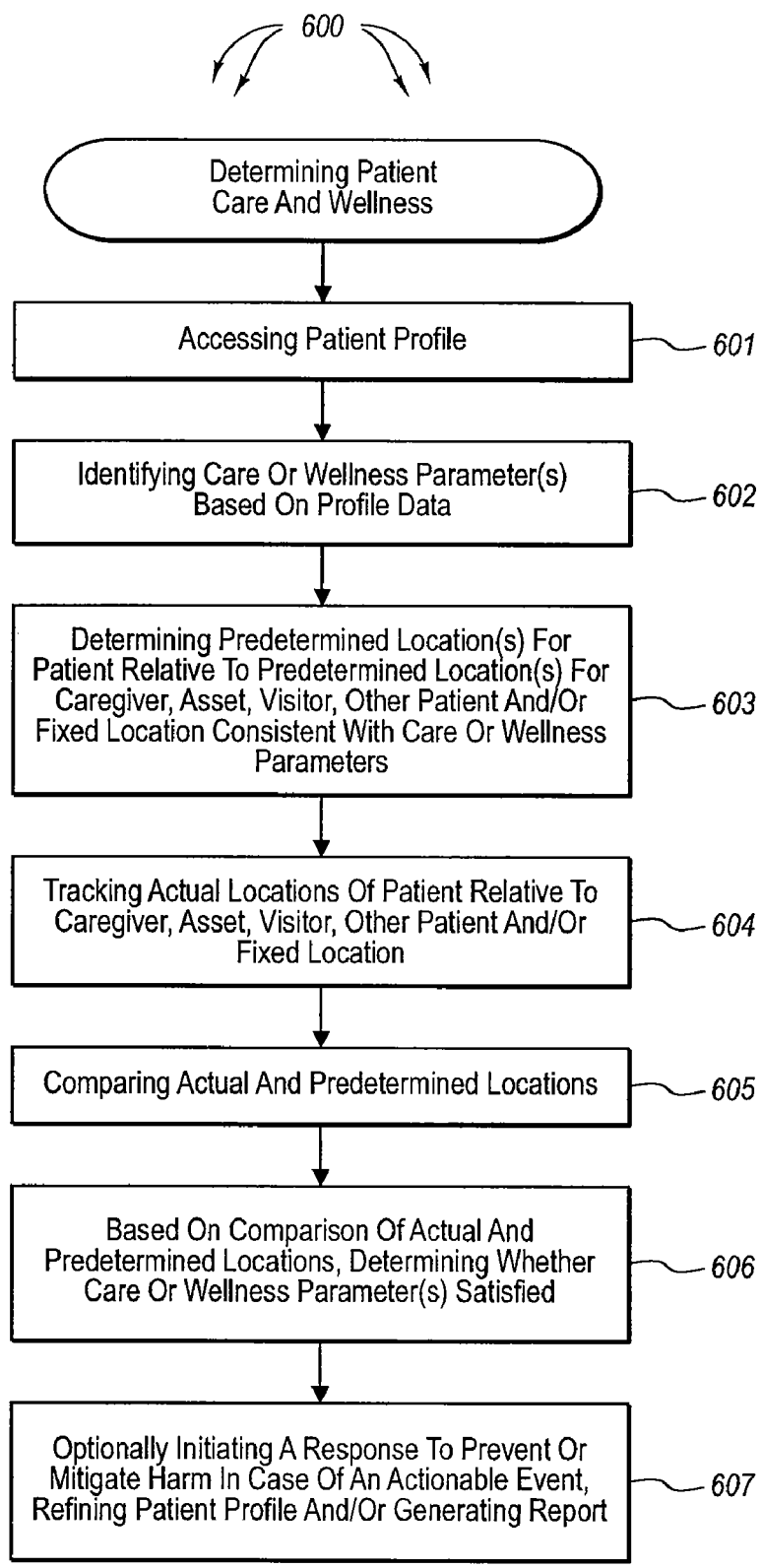
FIG. 6 is a flow chart that illustrates an exemplary method for determining patient care and wellness using individualized patient profiles.

FIG. 6 is a flow chart illustrating an exemplary method 600 for determining patient care and wellness. Method 600 includes an act 601 of accessing stored patient profiles, which contain data that relate to one or more care or wellness parameters. In most cases, the profile data will differ as between at least some of the patients based on the specific attributes and needs of each patient, which are rarely identical for all patients.

Act 602 involves identifying one or more care or wellness parameters for each of a plurality of patients based on profile data contained in a corresponding patient profile. Examples of care or wellness parameters include, but are not limited to, preventing unassisted bed exiting, measuring total ambulation of a patient in a given time period, assessing the level of patient socialization with others, detecting changes in patient gait, verifying the completion of treatments, exercises or care regimes, ensuring proper denture use, identifying periodic bed rolling for bed bound patients to prevent bed sores, responding to patient initiating emergency calls, preventing or mitigating patient harm, wandering or flight, ensuring proper nutrition, detecting breathing sounds, coughs, choking, etc. that may be indicative of impaired respiratory function, ensuring that patient ambulation occurs in association with prescribed assistive devices, and the like.

Act 603 includes determining one or more predetermined locations for each of a plurality of patients relative to one or more predetermined locations for at least one of a caregiver, asset, visitor, other patient or fixed location within or without the facility which are consistent with or that confirm or verify the satisfaction of the one or more care or wellness parameters identified in 602. Many care and wellness parameters involve interactions between a patient and a caregiver, visitor, other patient or asset. Tracking location can also include determining a time duration at a location or between multiple locations. Tracking the locations of each roughly indicates whether such interactions have actually occurred as prescribed. A patient who is never in the same location as the assigned individual or asset is unlikely to have had the required interaction for a care or wellness parameter to have occurred. Tracking nutrition or preventing patient wandering or flight typically involves comparing patient movements (i.e., changing locations) relative to a fixed location in or out of a facility (e.g., cafeteria, security zone, exit, parking lot, etc.).

By way of example, patients, staff, assets and visitors can be assigned an RFID device that can be tracked throughout a facility by means of an RFID detection system comprising a plurality of RFID detectors throughout the facility. The location of the RFID detectors and assignment of RFID devices can be recorded and maintained in a computer system. As patients, staff, assets and visitors move throughout the facility, the RFID detectors notify the computer system of RFID devices that are currently being detected. This computer system can correlate the location of each RFID device, as well as the duration of each RFID device at a specific location, and determine whether prescribed care and wellness routines or activities involving patients, staff, assets and/or visitors have been properly carried out.

Alternately to or in combination with RFID, patients, staff, assets and visitors can be assigned an ultrasound device that can be tracked throughout a facility by means of an ultrasound detection system comprising a plurality of ultrasound detectors throughout the facility. The location of the ultrasound detectors and assignment of ultrasound devices can be recorded and maintained in a computer system. As patients, staff, assets and visitors move throughout the facility, the ultrasound detectors notify the computer system of ultrasound devices that are currently being detected. This computer system can correlate the location of each ultrasound device, as well as the duration of each ultrasound device at a specific location, and determine whether prescribed care and wellness routines or activities involving patients, staff, assets and/or visitors have been properly carried out.

In act 605 and 606, the actual locations of the patient, caregiver, asset, visitor, other patients and/or fixed location are compared with the one or more predetermined locations relating to the one or more care or wellness parameters selected in 602 to determine if such care or wellness parameters have been satisfied. The location, movement and/or duration of a patient, caregiver, visitor, or other patient can be monitored to determine if prescribed duties or activities are actually carried out as prescribed (e.g., performed within predetermined time guidelines or in a proper location, such as bathing, assisted feeding, turning of bed ridden patients to prevent bed sores, etc.).

Measures can be taken to enhance patient care or wellness and/or prevent or mitigate harm to a patient. Thus, act 607 includes optionally initiating a response to prevent or mitigate harm in the case of an actual event, refining a patient profile and/or generating a care or wellness report. By way of example, staff can be alerted to prevent or mitigate patient wandering into unauthorized or forbidden areas (e.g., other patient rooms, facility exit, sensitive staff or equipment locations, etc.). Patient wellness events (e.g., social interactions, use of dentures, and proper nutrition) can be chronicled and, if necessary, improved through remedial action. Modification of patient profiles can assist in more accurately predicting patient's needs and limits. Generating a care and wellness report can assist providers or family members in ensuring enhanced care and wellness of the patient.

III. Profile Maintenance and Refinement

An important aspect of the inventive monitoring systems and methods for assessing and ensuring quality and performance is the use and refinement of patient specific profiles. Individual profiles permit the inventive patient monitoring systems and methods to more accurately assess the quality of care and wellness of each patient, as among a plurality of patients having a variety of different attributes and needs. Staff and visitor profiles permit analysis of staff and visitor performance at a healthcare facility. Patient, staff and visitor profiles also permit the inventive systems and methods to better interpret conditions and actions of patients, staff and visitors that may lead to an actionable or triggering event. This reduces the incidence of false positives and false negatives and may reduce staff response times to critical clinical events.

Figure 7:
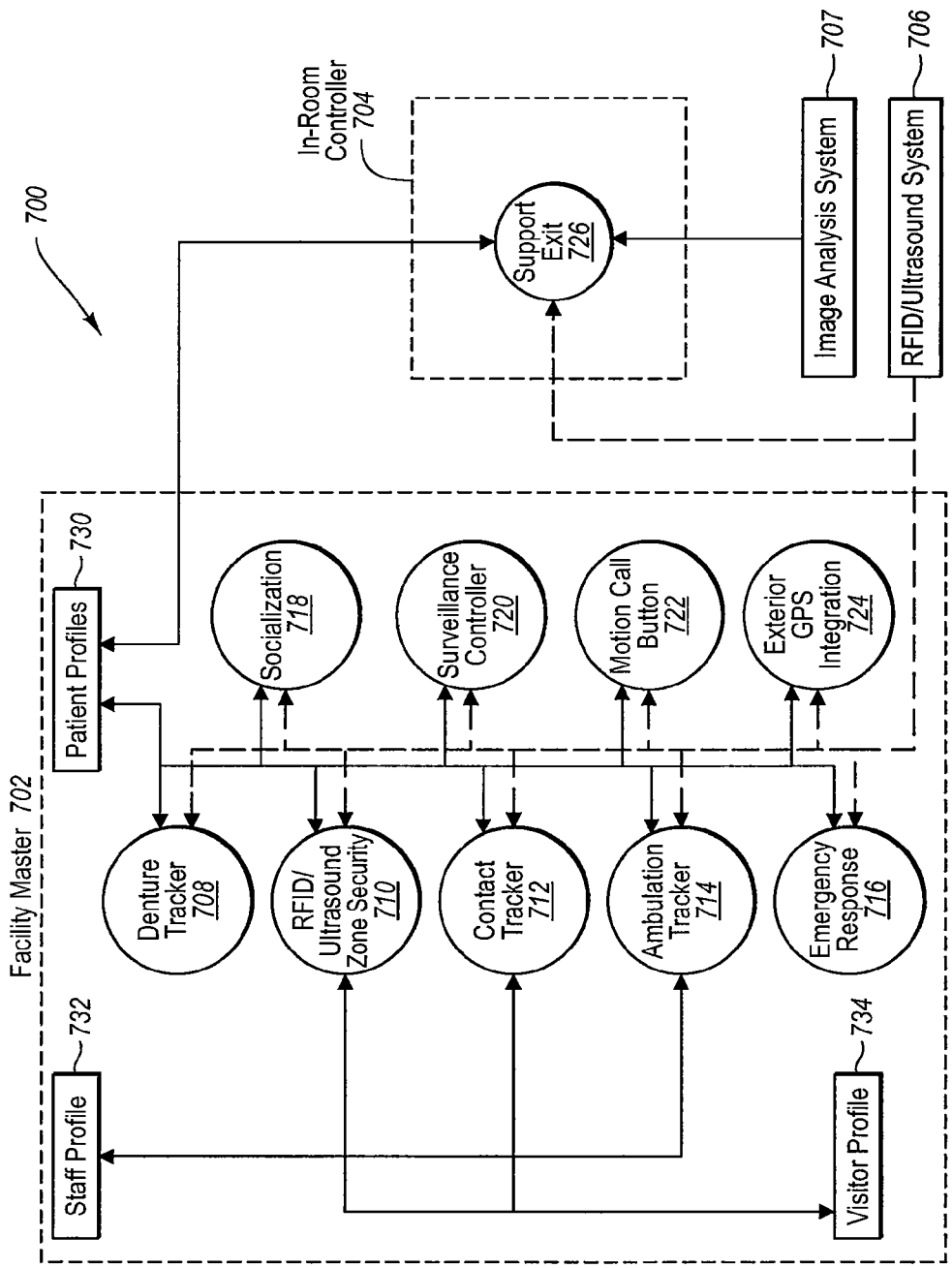
FIG. 7 schematically illustrates the interrelationship of various data gathering and analysis modules used to maintain and refine a patient profile.

FIG. 7 schematically illustrates an exemplary computer system 700 containing networked computers and interrelated functional modules and peripheral data gathering systems for gathering information regarding a plurality of patients, staff and visitors at a healthcare facility and updating patient, staff and visitor profiles. Computer system 700 more particularly includes a facility master 702 and in room controller 704. Of course, computer system 700 may include multiple in room controllers 704 and/or other computers as desired. An RFID and/or ultrasound system 706 interfaces directly with facility master 702 to provide data regarding the location and movements of patients, staff, assets and visitors. An image analysis system 707 interfaces directly with in room controller 704 to provide data regarding the location, behavior and/or condition of a patient in a room. A detailed discussion regarding detecting and responding to support exiting is set forth below.

The exemplary modules within facility master 702 include denture tracker 708, RFID/ultrasound zone security 710, contact tracker 712, ambulation tracker 714, emergency response 716, socialization 718, surveillance controller 720, mobile call button 722, and exterior GPS integration 724. The in room controller 704 includes support exit module 726, which interprets data from the image analysis system 707. It will be appreciated that additional modules and data generating peripherals may be included as required to generate and process other data types. The data that is processed by the foregoing modules shown in FIG. 7 is used to update or refine patient profiles 730, staff profiles 732, and visitor profiles 734. Each of the data processing modules as well as exemplary information contained within patient profiles 730, staff profiles 732 and visitor profiles 734 will now be discussed in detail.

The following discussion of functional modules regarding profile maintenance and refinement is also useful in understanding how the inventive methods and systems can be used to monitor and ensure a desired delivery of care and maintenance of patient wellness. They also assist in assessing the overall quality and performance of and at a healthcare facility. Thus, the following discussion of functional modules is also applicable to understanding how the methods and system help to monitor, deliver and/or ensure patient care and wellness as well as overall quality and performance.

A. Functional Modules

1. Support Exiting Module

As discussed above, the support exiting module 726 is typically located within the in room controller 704. The support exiting module 726 imports the most recently refined patient profile data relating to support exiting from facility master 702 so as to be locally stored at in room controller 704. Threshold issues include whether patient bed behavior is restricted and what time periods the restrictions are enforced. If support exiting behavior is not restricted for that patient or within a given time period, support exiting need not be monitored and responded to, at least within the given time period when the restriction is not in effect. Only if support exiting restrictions apply within a given time period does the support exiting module need to function to detect support exiting by the patient.

According to one embodiment, data from a plurality of data channels relating to various parts of the patients body are sampled with a frequency sufficiently high to obtain maximal event capture while minimizing unproductive hardware loads to populate support exiting algorithms (e.g., at 0.25 second intervals). The data channels contain continuously flowing data regarding the locations and/or time durations at specified locations for the patient's head, arms, hands, legs and torso. The algorithms for each patient are based on specific support exiting behavior for that patient based on the patient's profile. Examples of profile data relating to support exiting behavior and limits is set forth in a later section below. The profile data includes or is used to create specific combinations of triggers relating to specific combinations of body part movements and/or time durations at specific locations, which are individually populated and flagged if satisfied. If the correct combination of triggers for that patient is met simultaneously, an actionable event is detected and a response is initiated.

For example, the following data channels A through H have been assigned to measure the distance between a particular patient body part and a corresponding or related support (e.g., bed) zone and/or the time duration that a body part is in contact or proximity with the corresponding or related support zone.

Bed Exit Channels

A=head distance from head board (inches)
B*=B=head distance right (inches)
C*=C=head distance left (inches)
D=engagement of right upper bed rail (consecutive seconds)
E=engagement of left upper bed rail (consecutive seconds)

F=leg within exit zone right (consecutive seconds)
G=leg within exit zone left (consecutive seconds)
H=head height of elevation (inches)

As discussed below, there are seven common bed exiting behaviors which are consistent with specific combinations of behaviors corresponding to information measured by each of data channels A though H.

Trigger Combinations for Alerts

| Bed slide | A |
|---|---|
| Side rail roll right | D and B |
| Side rail roll left | E and C |
| Torso up/side rail roll right | H and B* |
| Torso up/side rail roll left | H and C* |
| Torso up/leg kick right | H and F |
| Torso up/leg kick left | H and G |

When a distance or time duration matches information contained within a patient's profile of support exiting behavior, that variable is flagged. When all of the variables for the specific support exiting behavior for a patient are triggered, an alert or alarm may be triggered and a response initiated. Different patients may have different trigger values for the various behaviors depending on known support exiting behavior, patient size, and other attributes.

Upon the occurrence of a predetermined combination of behaviors consistent with support exiting for a specific patient, an alarm may be triggered and a response initiated. An exemplary support exiting response includes: (1) initiating HIPAA notification to the patient of potential viewing of video feed of patient; (2) establishing an A/V link to a nursing station for nurse only viewing of the patient; (3) verifying nurse's presence at the nursing station within an established time response period by the nurse verifying or rejecting whether support exiting is actually occurring; (4) alternatively initiating an automatic response if nurse's presence not verified within time response period; (5) if nurse's response is "reject", with the option of mandatory staff approval, modifying the patient profile to loosen support exiting limits and notifying resident that viewing is concluded; (6) if nurse's response is "accept", establishing "video stall" A/V link to delay support exiting, sending message to assigned PDA and closest nurse PDA of event, beginning nurse floor response time timer (finish when nurse RFID or ultrasound enters requested room), and modifying patient profile to confirm or tighten support exiting limits; and (7) generating bed exit event report for each 24 hour period. A more detailed description of support exiting and response is set forth in a later section below.

2. RFID/Ultrasound Zone Security Module

As discussed above, the RFID/Ultrasound zone security module 710 is typically located in the facility master 702. According to one embodiment, the RFID/Ultrasound zone security module 710 scans the RFID zone locations and/or ultrasound zone locations of patients, staff and visitors at a facility at a frequency sufficiently high to obtain maximal event capture while minimizing unproductive hardware loads (e.g., at 1.0 second intervals). Using profile data, the module 710 classifies individual locations as one of: (1) safe, (2) warning or (3) violation. If the location classification is safe, no alerts or alarms are initiated.

In the case where a patient's or visitor's location triggers a "warning", a timer is initiated. If the location of the individual at issue does not downgrade to "safe" within a prescribed timer interval (e.g., "X" seconds), an alert is sent to the nursing station and a staff response timer mode is initiated. The timer runs until the individual is removed from any restricted RFID and/or ultrasound zones. The amount of elapsed time can be used to assess staff performance.

If an individual's location triggers a "violation", an alert is sent to the nursing station and possibly security, and a staff response timer mode is initiated. The timer runs until the individual is removed from any restricted RFID and/or ultrasound zones. The amount of elapsed time can be used to assess staff performance. According to one embodiment, nursing station staff can visually and/or verbally instruct the patient or visitor to vacate the restricted area through the use of an A/V interface. A security zone report can be generated every 24 hours if requested.

In order to illustrate how an initial flight risk level for a given patient, coupled with monitored behavior, may trigger appropriate alerts and alarms in the case of possible building flight, the following example is given. The box below is a grid that illustrates various danger zone values surrounding a building exit, with the lower numbers representing geographic zones that are farther away from the exit, and higher numbers representing geographic zones that are closer to the exit. The danger zone values can be used to calculate a present flight risk level for each of a plurality of patients as they move toward the exit, which is next to danger zone 8.

| 3 | 4 | 8 | 4 | 3 |
|---|---|---|---|---|
| 2 | 3 | 5 | 3 | 2 |
| 1 | 1 | 2 | 1 | 1 |
| 1 | 1 | 1 | 1 | 1 |
| 0 | 0 | 0 | 0 | 0 |

By way of example, a patient of known normal flight risk might be assigned an initial flight risk score of 10. A patient having a known high flight risk level might be given an initial score of 5. The lower the score, the higher the flight risk. Whenever a patient enters a zone having a danger zone value that is equal to or greater than the danger value of preceding zone, the initial flight risk score is modified by subtracting the present danger zone value. Thus, if a patient with an initial flight risk score of 10 enters a flight zone with a danger zone value of 1, the patient's current flight risk score is reduced to 9. Entering danger zones of equal or greater value results in further reductions in the current flight risk score. An alert of possible flight risk and A/V intervention may be triggered, for example, if the flight risk score falls to below a predetermined threshold (e.g., below 4). An alarm is triggered if the flight risk score falls to 0 or below (i.e., a negative number) and direct intervention to prevent or mitigate actual flight is initiated. If, after entering a danger zone with a given value, the patient turns around and enters a danger zone having a lower value, the flight risk score can be increased to reflect the lessened flight risk.

3. Ambulation Tracker Module

As discussed above, the ambulation tracker module 714 is typically located in the facility master 702. According to one embodiment, the ambulation tracker module 714 measures the total ambulation distance for each patient and staff member by determining the total number of RFID and/or ultrasound zones occupied by each individual during each 24 hour period and multiplying that value by the (RFID and/or ultrasound) zone size (e.g., 3 feet). Daily ambulation values are buffered to generate weekly averages. Alerts may be generated when daily values differ from the historical average by more than 50%. The overall trend for weekly averages can be monitored to determine the existence of increases or declines in ambulation. Ambulation reports and be generated for patients, staff and visitors every 24 hours if requested. Patient health, staff performance and visitor behaviors can be assessed using ambulation values.

According to another embodiment, ambulation tracker module 714 polls patient profiles to determine which patients require ambulation assistance devices (e.g., walker, wheelchair or crutches). If so, the module 714 also tracks the location of any assigned devices for each patient using the associated RFID or ultrasound for the device. For the subset of patient requiring ambulation devices, determining whether any patient moves between RFID and/or ultrasound zones without detecting the presence of the assigned RFID or ultrasound tagged ambulation device. If separation of patient and ambulation device is determined, initiating an alert to the nursing station for possible intervention. Assistive ambulation device reports can be generated for patients every 24 hours if requested.

The ambulation tracker module 714 can also detect potentially dangerous changes in patient gait by noting the time it takes for a patient to move between zones. For example, for a patient who normally passes between RFID and/or ultrasound zones at a particular pace, detecting substantial slowing or unusual movement between zones may be an indication of a serious medical condition.

4. Contact Tracker Module

As discussed above, the contact tracker module 712 is typically located in the facility master 702. The purpose is to determine and verify the existence of prescribed patient/staff contacts as they may relate to patient care and wellness and/or staff performance. According to one embodiment, the contact tracker module 712 polls a patient's profile for all elements that require patient/staff contact to be performed and/or delivered on a prescribed schedule. Examples include: (1) meals brought directly to rooms—denoted by RFID or ultrasound tagged meal tray; (2) special diet restrictions—denoted by RFID tagged meal tray; (3) assistance during mealtimes in room; (4) trips to cafeteria during meal times per day; (5) in-room therapy required without medical device; (6) in-room therapy required with one or more devices (i.e. assets) A; (7) in-facility therapy/physical therapy; (8) assisted facility exits.

The RFID/ultrasound system 706 is monitored to count each of these events and compare to prescribed standards set within each patient profile. The time period of patient/staff interaction should be measured and compared to pre-set minima and maxima. Alerts and alarms may be generated if an increasing degree of poor staff performance is detected. Data generated by the contact tracker module can be used to assess patient care and wellness and/or staff performance.

5. Socialization Module

As discussed above, the socialization module 718 is typically located in the facility master 702. The purpose is to determine the degree of patient socialization as it may relate to patient care and wellness. The socialization module 718 analyzes RFID and/or ultrasound monitored patient movements and behaviors and generates either a (+) or (−) influence on a numeric value that represents each patient's socialization factor (PSF). PSF may normally begin at a default value 5 and increase to a maximum of 10 and decrease to a minimum of 1 depending on patient activities. High, low or changing PSF are an objective measure of patient wellness.

Exemplary patient activities that count as a possible (+) PSF influencing element include: (1) visitors visiting patient's room; (2) assisted exits of facility; (3) other patients to patient's room; (4) trips by patient to other patient's rooms; (5) time in common areas (e.g., cafeteria, courtyard, recreation rooms, etc.) when occupied by visitors other patients; (6) activation of "family plan" communication elements; (7) contact time with pets (e.g., "canine therapy"); and (8) time/trips to facility courtyard area.

Exemplary patient activities that count as a possible (−) PSF influencing element include: (1) consecutive hours in room alone; (2) missed meals; (3) repetitive ambulation behavior (e.g., walking back-and-forth or in circles); and (4) decreased levels of daily ambulation. Drastic decreases in PSF below previous values or an RSF below a critical minimal limit (e.g., 2) may result in the generation of alerts and alarms. Periodic socialization reports for each patient can be generated to assess patient wellness and/or staff or visitor performance (e.g., letters can be sent to relatives requesting more visits).

6. Surveillance Controller Module

As discussed above, the surveillance controller module 720 is typically located in the facility master 702. According to one embodiment, the surveillance controller module 720 monitors RFID, ultrasound, motion detection, video cameras and/or door beam tripping data to detect the entrance of staff, patients, or visitors into a patient's room or other private zone. Upon authorized entry by individuals into a patient's room, as detected using assigned RFID and/or ultrasound devices, the surveillance controller module 720 initiates A/V monitoring of the patient's room and triggers HIPAA appropriate patient notification. Upon room clearing of RFID and/or ultrasound signals (other than those which assigned resident), surveillance controller module 720 terminates A/V monitoring.

Upon unauthorized entry by individuals into a patient's room, as detected by image analysis of video data, motion detection and/or door beam tripping data in the absence of properly assigned RFID and/or ultrasound devices, the surveillance controller module 720 initiates an alarm at the nursing station, security is notified, and an event response timer is initiated. The event response timer is terminated when authorized staff RFID and/or ultrasound signal enters the patient's room. The event response time can be used to assess staff performance. The surveillance controller module 720 time stamps and attaches a patient identifier code to A/V surveillance files, which are stored for a prescribed number of days (e.g., 15 days).

7. Emergency Response Module

As discussed above, the emergency response module 716 is typically located in the facility master 702. The purpose is to notify staff and patients of a facility emergency and initiate an appropriate response to prevent or mitigate patient harm. Upon confirming the occurrence of a facility emergency (e.g., a fire), a qualified staff member inputs the location of the event into the system. The emergency response module 716 causes the system to send messages to all patient rooms with evacuation instructions. The emergency response module 716 tracks the evacuation of all patients and staff via tracking the movements of assigned RFID and/or ultrasound devices for each patient and staff member. Laptop PC and network access at locations external to the building can be provided for administration and emergency response personnel.

8. Mobile Call Button Module

As discussed above, the mobile call button module 722 is typically located in the facility master 702. Patients and staff can wear RFID and/or ultrasound bracelets that include a manual call button that allows for manual activation of a secondary RFID transmitter or ultrasound transmitter during emergency situations. When an emergency RFID or ultrasound signal is detected, the mobile call button module 722 determines who triggered the alert and where the individual is located. The mobile call button module 722 polls the assigned patient profile for a list of most critical medical conditions. The mobile call button module 722 transmits information regarding the call for help and any most critical medical conditions to the closest staff PDA for response and starts response timer mode. The mobile call button module 722 determines if A/V communication is supported in the location of the emergency, and if so, establishes an A/V link between the location and a nursing station. At the conclusion of the event, nursing station staff inputs whether or not an actual emergency occurred and the patient's profile is updated to note inappropriate emergency call button usage (e.g., ordering room service, using it for social calls, horseplay, etc.).

9. External GPS Integration Module

As discussed above, the external GPS integration module 724 is typically located in the facility master 702. The external GPS integration module 724 allows for hand off of patient tracking from the RFID/ultrasound system 706 to GPS when residents travel into an exterior courtyard region of the facility not equipped with RFID or ultrasound zone sensors and/or in cases of patient wandering or flight. Patient movement toward a courtyard can be determined by a patient assigned RFID or ultrasound device entering zones leading to the courtyard.

The external GPS integration module 724 polls the patient profile for privilege or limit information, including: (1) courtyard privileges for the patient; (2) courtyard time of day restrictions; (3) courtyard time duration outside limits; (4) courtyard maximum outside temperature limits; (5) courtyard minimum outside temperature limits; and (6) the assigned GPS transmission code for that patient. If conditions are not met for courtyard access, the module 724 causes system to alert the nursing station and being a response timer. If conditions are met for courtyard access, then start courtyard duration timer.

10. Denture Tracker Module

As discussed above, the denture tracker module 708 is typically located in the facility master 702. According to one embodiment, the denture tracker module 708 ensures that prescribed denture cleaning schedules are maintained. By means of denture embedded RFID or ultrasound devices, track the time period between denture RFID or ultrasound signal occupying an RFID or ultrasound zone dedicated to denture cleaning station. Cleaning dentures too often or too infrequently can be noted in an appropriate report. Tracking proper cleaning of dentures is a measure of patient care and wellness.

According to another embodiment, the denture tracker module 708 ensures a proper match between an upper denture, lower denture, and the patient. It does so by tracking the locations of patients and corresponding dentures. For example, the denture tracker module 708 may determine whether a denture RFID or ultrasound signal that is changing zones (i.e., moving) belongs to the patient moving through equivalent RFID or ultrasound zones. If not, the module 708 sends an alert nursing station and generates a report.

Other assets can be tracked and matched with assigned patients in similar fashion.

B. Exemplary Profiles

1. Patient Profile

The type of data contained in a patient profile can be selected, populated and modified as required depending on any desired care and wellness criteria and/or learned information. The following patient profile is merely one example of a suitable profile for use in collecting and processing data by the modules described above. It is given by way of example, not by limitation. Each line represents an independent inquiry that can be analyzed using one or more computer-monitored data channels. Data may be static or dynamic. Dynamic data can either by altered automatically or manually.

S=Static Parameter
AD=Automatically Dynamic Parameter
MD=Manually Dynamic Parameter 1. bed exit monitoring required—(y/n), S
2. evening bed bound initiation time—xx:xx, S
3. morning bed bound termination time—xx:xx, S
4. limit on head to head board distance—x inches, AD tighten, MD loosen
5. number of bed slide exit attempts—#, AD
6. limit on right hand bedrail loading—x seconds, AD tighten, MD loosen
7. number of right side bedrail exit attempts—#, AD
8. limit on left hand bedrail loading—x seconds, AD tighten, MD loosen
9. number of left side bedrail exit attempts—H, AD
10. limit on head elevation—x inches, AD tighten, MD loosen
11. number of torso up/bedrail roll exit attempts—#, AD
12. dietary restrictions—(y/n), S
13. diabetic food restrictions—(y/n), S
14. soft food restrictions—(y/n), S
15. in-room assistance required during eating—(y/n), S
16. number of trips to cafeteria during breakfast/lunch/dinner time periods per day—#, AD
17. assisted turning in bed per evening time block—H, AD
18. unassisted turns in bed per evening time block—#, AD
19. socialization counter—1 to 10 scale, AD
20. hallway gait timer—x minutes, AD
21. total daily ambulation counter—x minutes and y distance, AD
22. weekly ambulation average—x minutes and y distance, AD
23. total daily (ambulation with assistive device) counter—x minutes and y distance, AD
24. weekly (ambulation with assistive device) average—x minutes and y distance, AD
25. in-room therapy without device—(y/n), S
26. in-room therapy with device—(y/n), S
27. staff presentations in room with device per day—#, AD
28. ambulation with device mandatory—(y/n), S
29. corresponding ambulation device or devices—RFID/ultrasound code, S
30. maxillary denture—RFID/ultrasound code, S
31. mandibular denture—RFID/utlrasound code, S
32. denture cleaning schedule counter—# per week, AD
33. bathroom time limit—x minutes, S
34. courtyard privileges—(y/n), S
35. courtyard time of day restrictions—xx:xx, S
36. courtyard duration outside limit—x minutes, S
37. courtyard maximum outside temperature—x ° F./C, S
38. courtyard minimum outside temperature—x ° F./C, S
39. unassisted facility exiting—(y/n), S
40. level of flight risk—#, AD tighten, MD loosen
41. number of authorized facility exits per month—#, AD
42. number of unauthorized facility exits or attempts per week—#, AD
43. facility restricted areas—RFID/ultrasound codes, S
44. inappropriate emergency call button usages—#, AD
45. pet therapy contact—(y/n), S
46. critical medical history—[data], S
47. emergency call contact #1, S
48. emergency call contact #2, S
49. emergency call contact #3, S

2. Staff Profile

The type of data contained in a staff profile can be selected, populated and modified as required depending on any desired quality or performance criteria and/or learned information. Staff performance will typically relate in some way to providing patient care and wellness and may differ based on specific attributes, assignments and/or rights of each staff member. The following staff profile is merely one example of a suitable profile for use in collecting and processing data by the modules described above. It is given by way of example, not by limitation. Each line represents an independent inquiry that can be analyzed using one or more computer-monitored data channels. Data may be static or dynamic. Dynamic data can either by altered automatically or manually.

S=Static Parameter
AD=Automatically Dynamic Parameter
MD=Manually Dynamic Parameter 1. work schedule—day of week, time of day, S
2. restricted RFID/ultrasound zones—x,y,z, S
3. assigned resident rooms—x,y,z, S
4. total ambulation—time x and distance y, AD
5. most visited room—time x, AD
6. second most visited room—time x, AD
7. third most visited room—time x, AD
8. fourth most visited room—time x, AD
9. fifth most visited room—time x, AD
10. sixth most visited room—time x, AD
11. seventh most visited room—time x, AD
12. eighth most visited room—time x, AD
13. ninth most visited room—time x, AD
14. tenth most visited room—time x, AD
15. number of facility exits per day—#, AD
16. duration of facility exits—minutes x, AD
17. % of total work time spent with patients, AD
18. % of total work time spent with other staff, AD
19. % of total work time spent alone, AD

3. Visitor Profile

The type of data contained in a visitor profile can be selected, populated and modified as required depending on any desired performance criteria and/or learned information. Visitor performance may relate to attribute and rights of each visitor and also patient care and wellness. The following visitor profile is merely one example of a suitable profile for use in collecting and processing data by the modules described above. It is given by way of example, not by limitation. Each line represents an independent inquiry that can be analyzed using one or more computer-monitored data channels. Data may be static or dynamic. Dynamic data can either by altered automatically or manually.

S=Static Parameter
AD=Automatically Dynamic Parameter
MD=Manually Dynamic Parameter 1. identification number (drivers license #)—xxxxxx, S
2. biometric scan data, S
3. time of day restriction for entrance—xx:xx, S
4. associated resident RFIDs/ultrasound signals—x,y,z, S
5. allowed resident room RFID/ultrasound zones—x,y,z, S
6. generic allowed RFID/ultrasound zones—x,y,z, S
7. generic restricted RFID/ultrasound zones—x,y,z, S
8. can patient leave facility with visitor assistance? (y/n), S
9. most visited room—x, AD
10. second most visited room—x, AD
11. third most visited room—x, AD
12. fourth most visited room—x, AD
13. fifth most visited room—x, AD
14. most commonly associated human RFID/ultrasound signal—x, AD
15. second most commonly associated human RFID/ultrasound signal—x, AD
16. third most commonly associated human RFID/ultrasound signal—x, AD
17. fourth most commonly associated human RFID/ultrasound signal—x, AD

C. Refinement of Profiles

Figure 8:
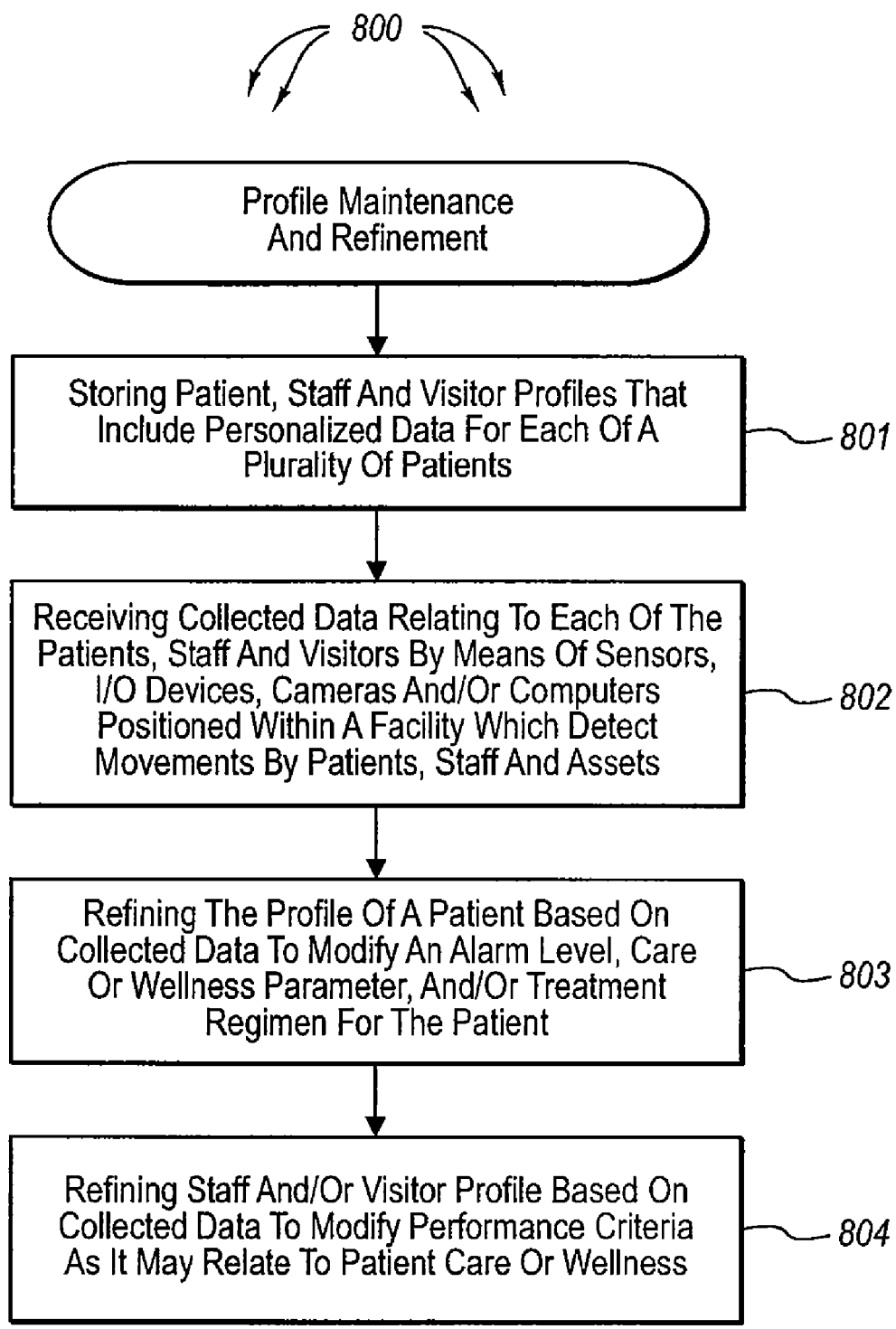
FIG. 8 is a flow chart that illustrates an exemplary method for maintaining stored profiles for a plurality of patients at a healthcare facility.

FIG. 8 illustrates a flow chart of a method 800 for maintaining and refining stored profiles for patients, staff and visitors at a healthcare facility. Method 800 includes an act 801 of storing an initial profile for each of a plurality of patients, staff or visitors at a facility based on at least one of specific personalized information for each patient, staff or visitor, or general information common to more than one individual. The patient profiles may include at least one of an alarm level for use in triggering an actionable event, a treatment regimen for the patient, or wellness measurement for the patient. The staff and visitor profiles may include initial information relating to staff and visitor performance as it may relate to the care or wellness of patients.

Method 800 includes an act 802 of receiving collected data relating to each of the patients, staff or visitors at the facility. The data can be collected using one or more sensors, I/O devices, cameras or computers positioned within the facility that detect or provide data regarding movements by patients, staff, visitors and assets.

Act 803 involves refining the profile of a patient based on the collected data in order to modify at least one of an alarm level, care or wellness parameter, or a treatment regimen for the patient. The patient profile can be updated by way of an information feedback loop in which potentially actionable events are confirmed or denied through human intervention. In some embodiments, stored patient profiles are risk profiles that include recursively refined patient alarms levels indicative of actionable events requiring a response. Finally, method 800 includes an act 804 of refining staff and/or visitor profiles based on collected data relating to staff and/or visitor performance, which will typically relate in some way to ensuring or gauging patient care and wellness.

IV. Systems and Methods for Monitoring Patient Support Exiting and Response

Monitoring and responding to unassisted patient support exiting is an example of a specific care and wellness parameter. It helps increase the overall quality and performance of a facility. Potential support exiting can be monitored by determining the location of a patient, particularly the location and/or time duration of specific body parts relative to fixed locations. Detecting potential patient support exiting in advance of actual support exiting gives a caregiver the opportunity to intervene and prevent support exiting, assist support exiting, or mitigate patient harm.

Figure 9:
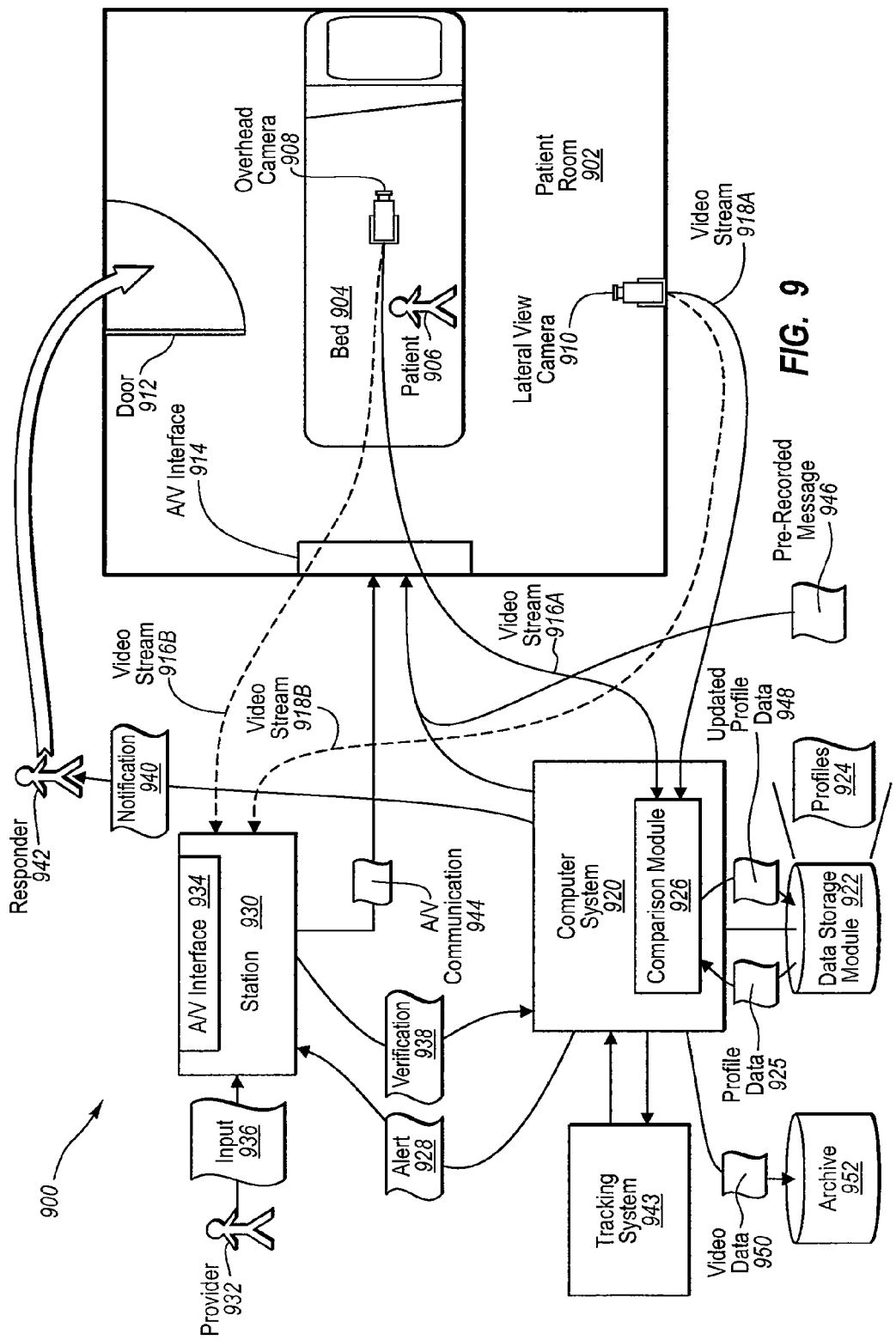
FIG. 9 schematically illustrates an exemplary system for patient monitoring, alert and response.

FIG. 9 is a diagram that schematically illustrates an exemplary computer-controlled system 900 for patient monitoring, more particularly with respect to potential patient support exiting, detecting a position and/or movement of a patient that is predictive of support exiting, obtaining human verification of actual support exiting, and intervening if support exiting is confirmed. The patient monitoring system 900 includes a patient room 902 containing a bed 904 or other support and a patient 906 resting thereon at least some of the time. One or more overhead cameras 908 may be provided that provide an aerial view of patient 906 together with one or more side or lateral view cameras 910. The overhead camera 908 is especially useful in monitoring lateral (i.e., side-to-side) and longitudinal (i.e., head-to-foot) patient movements, although it may also monitor other movements. The lateral view camera 910 is especially useful in monitoring longitudinal and up and down movements, although it can monitor other movements. The lateral view camera 910 and/or other camera (not shown) can be positioned to monitor and record a patient room door 912 or other access point (e.g., to detect and/or record entry and/or exit of personnel, other patients, or visitors). The bed 904 may include markings (e.g., decals) (not shown) that assist in properly orienting the cameras to fixed reference points. The markings may assist in determining the distance between a fixed point and body part.

The room 902 also includes an audio-video interface 914 that can be used to initiate one-way and/or two-communication with the patient 906. According to one currently preferred embodiment, A/V interface 914 is mounted to a wall or ceiling so as to be seen by patient 906 (e.g., facing the patient's face, such as beyond the foot of the patient's bed). The A/V interface 914 may include any combination of a video monitor (e.g., flat panel screen), a camera mounted adjacent to the video monitor (e.g., below), one or more microphones, and one or more speakers. The A/V interface may form part of a local computer system (e.g., an "in room controller") that controls the various sensors and communication devices located in the patient room.

In order to analyze patient movements that may be predictive of support (e.g., bed) exiting, video data streams 916A and 918A are sent from cameras 908 and 910, respectively, to a computer system 920 for analysis. According to one currently preferred embodiment, at least a portion of the computer system 920 is an in room controller associated with the patient room 902. In the case where each patient room has its own in room controller, patient monitoring and analysis of multiple patients can be simultaneously performed in parallel by dedicated in room controller computers. Nevertheless, at least some of the tasks, information gathering, and information flow may be performed by a remote computer, such as a central facility master computer. The computer system 920 may therefore include multiple networked computers, such an in room controller, facility master, and other computers. The computer system 920 includes or has access to a data storage module 922 that includes patient profiles 924 (e.g., stored and updated centrally in the facility master and used locally by and/or uploaded to the in room controller).

A comparison module 926 of the computer system 920 analyzes the video streams 916A, 918A and, using one or more algorithms (e.g., that may be known in the art or that may be developed specifically for this system), determines the location and/or any movements and/or duration of body part action of patient 906. This information is compared to patient specific profile data 925 from a patient profile 924 that corresponds to patient 906. In the absence of predicted support exiting or other triggering event, video streams 916A and 918A are typically not viewed by any human but are actively deleted or simply not stored or archived. This helps protect patient privacy.

When one or more locations, durations and/or movements of patient 906 match or correlate with profile data 925 predictive of support exiting by patient 906, the computer system 920 sends an alert 928 to a central station 930 (e.g., nursing station) that patient 906 may be attempting to exit support 904. In addition to the alert 928, at least one of video streams 916B, 918B from cameras 908, 910 and/or a modified video stream (not shown) from computer system 920 is sent to an A/V interface 934 at central station 930 for human verification of actual patient support exiting. The patient 906 is advantageously notified of potential active viewing by staff to satisfy HIPAA regulations (e.g., by a chime, prerecorded message, e.g., "camera is actively viewing", or visual indication, e.g., flashing or illuminated words, TV raster pattern). A provider 932 views the video stream(s) from patient room 902, determines whether the patient 906 is in fact preparing to exit the bed 904 or other support, and provides verification input 936 to an appropriate interface device (not shown) at station 930, which sends verification 938 to the computer system 920. Verification 938 may either confirm or reject actual patient support exiting. When viewing is terminated, the patient may be notified of this fact by, e.g., a tone or pre-recorded message ("active viewing is terminated").

If the provider 932 determines and verifies that actual patient support exiting is occurring or about to occur, the in room controller, facility master, or other appropriate module or subsystem component within computer system 920 sends a notification 940 to a responder 942 to assist the patient 906. Notification 940 may be sent by any appropriate means, including an audio alert using a PA system, a text and/or audio message sent to a personal device carried by responder 942, a telephone alert, and the like. A tracking system 943 that interfaces or communicates with the computer system 920 (e.g., the facility master) may be used to identify a caregiver 942 who is assigned to patient 906 and/or who is nearest to patient room 902. In this way, direct physical assistance to patient 906 who may be attempting to exit support 904 can be provided quickly and efficiently.

In addition to or instead of sending notification 940 to responder 942, one- or two-way A/V communication 944 can be established between provider 932 at central station 930 and patient 906 (e.g., by means of A/V interfaces 914 and 934). This allows provider 932 to talk to patient 906 in order to provide instructions or warnings regarding support exiting, possibly to distract patient 906 and delay or prevent support exiting (e.g., "why are you getting out of bed?"). This may allow responder 942 to more easily intervene prior to actual support exiting so as to prevent or better mitigate potential harm to patient 906. A pre-recorded audio and/or A/V message 946 may alternatively be sent to A/V interface 914 in patient room 902 instead of direct A/V communication between provider 932 and patient 906.

In the event a provider 932 is not present at central station 930 or otherwise fails to provide verification 938 regarding predicted support exiting within a prescribed time period, the computer system 920 may initiate an automated response in order to prevent or mitigate potential harm to patient 906. This may include one or both of sending notification 940 to a responder 942 regarding possible support exiting and/or sending a pre-recorded message 946.

Verification 938, whether confirmation or denial of actual support exiting, can also be used to update the patient profile 924 corresponding to patient 906. Updated profile data 948 based on one or more support exiting events can be input or stored at data storage module 922. If a particular behavior is found to accurately predict support exiting by patient 906, the patient profile 924 can be updated to confirm the accuracy of the initial profile 924. In some cases, limits within the patient profile 924 may be tightened to be more sensitive to movements and/or durations of actions that have been confirmed to correlate with and accurately predict support exiting. This may be done manually by authorized personnel or automatically by the computer system 920. If, on the other hand, a particular behavior is determined to falsely predict support exiting by patient 906, the patient profile can be updated to note incidences of such false positives. Limits within the patient profile 924 can be loosened or eliminated relative to movements that have been found not to correlate with support exiting by patient 906. In the event support exiting by patient 906 occurs but is not detected by the computer 920, limits within the patient profile 924 can be established and/or tightened in an effort to eliminate false negatives of support exiting by patient 906. Updating the profile 924 of patient 906 to more accurately predict support exiting and reduce or eliminate false positive and false negatives substantially increases the reliability of the patient monitoring system as compared to conventional systems that do not distinguish between and among support exiting habits or behaviors of different patients. The foregoing is an example of the use of an information feedback loop to refine a patient profile.

In order to later view and/or analyze a triggering event as may be established by a facility, video data 950 that is the same as, or which may be derived from, one or both of video streams 916, 918 can be stored within an archive 952. Archive 952 may comprise any storage media known in the art of video recording and storage, examples of which include hard drives, optical storage devices, magnetic tapes, memory devices, and the like. The triggering event need not be support exiting but may be entry into the patient's room by staff, other patients or visitors, or activation of the emergency call button by the patient.

Figure 10A:
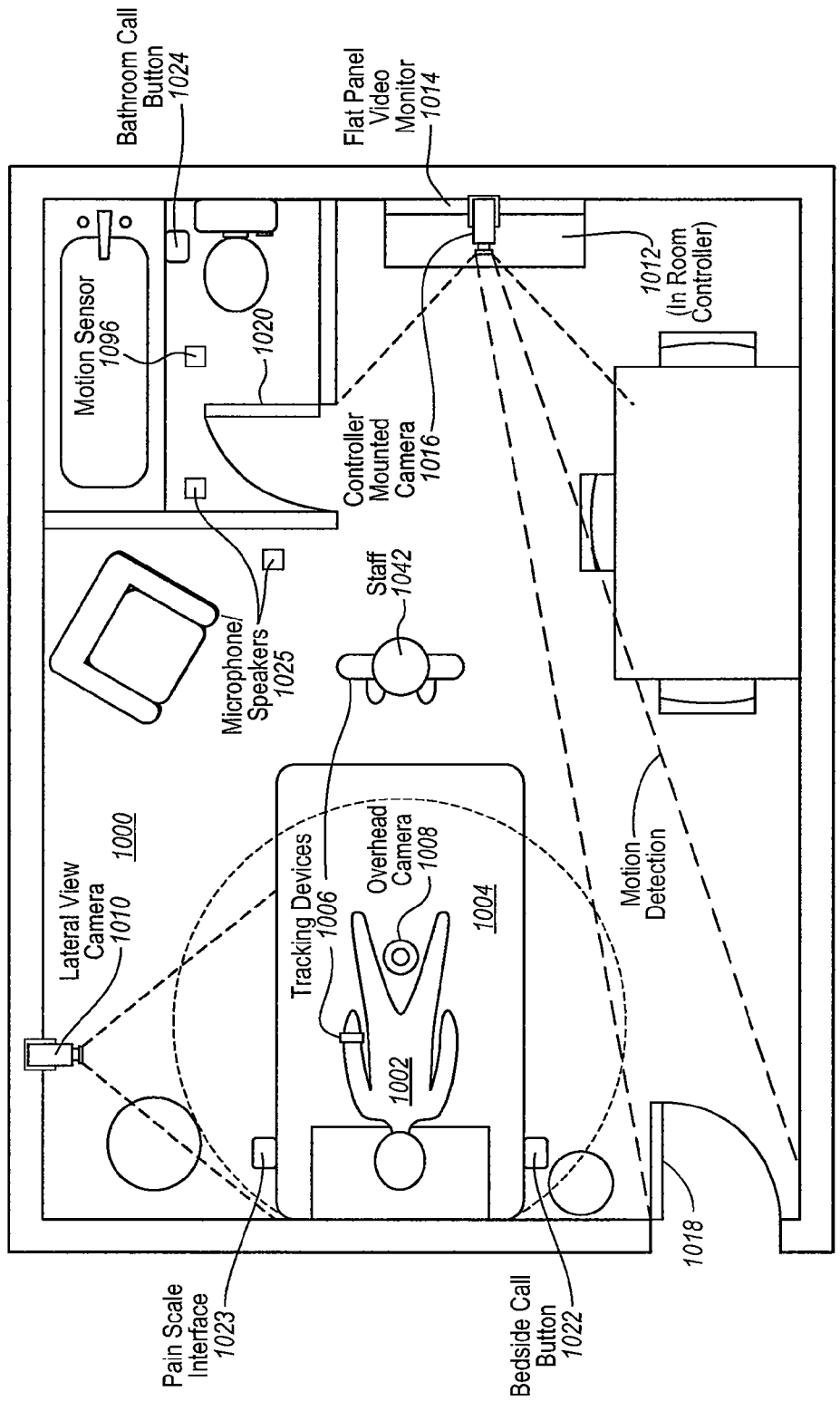
FIGS. 10A and 10B schematically illustrate exemplary configurations of patient rooms at a healthcare facility equipped for patient monitoring and response to support exiting.
Figure 10B:
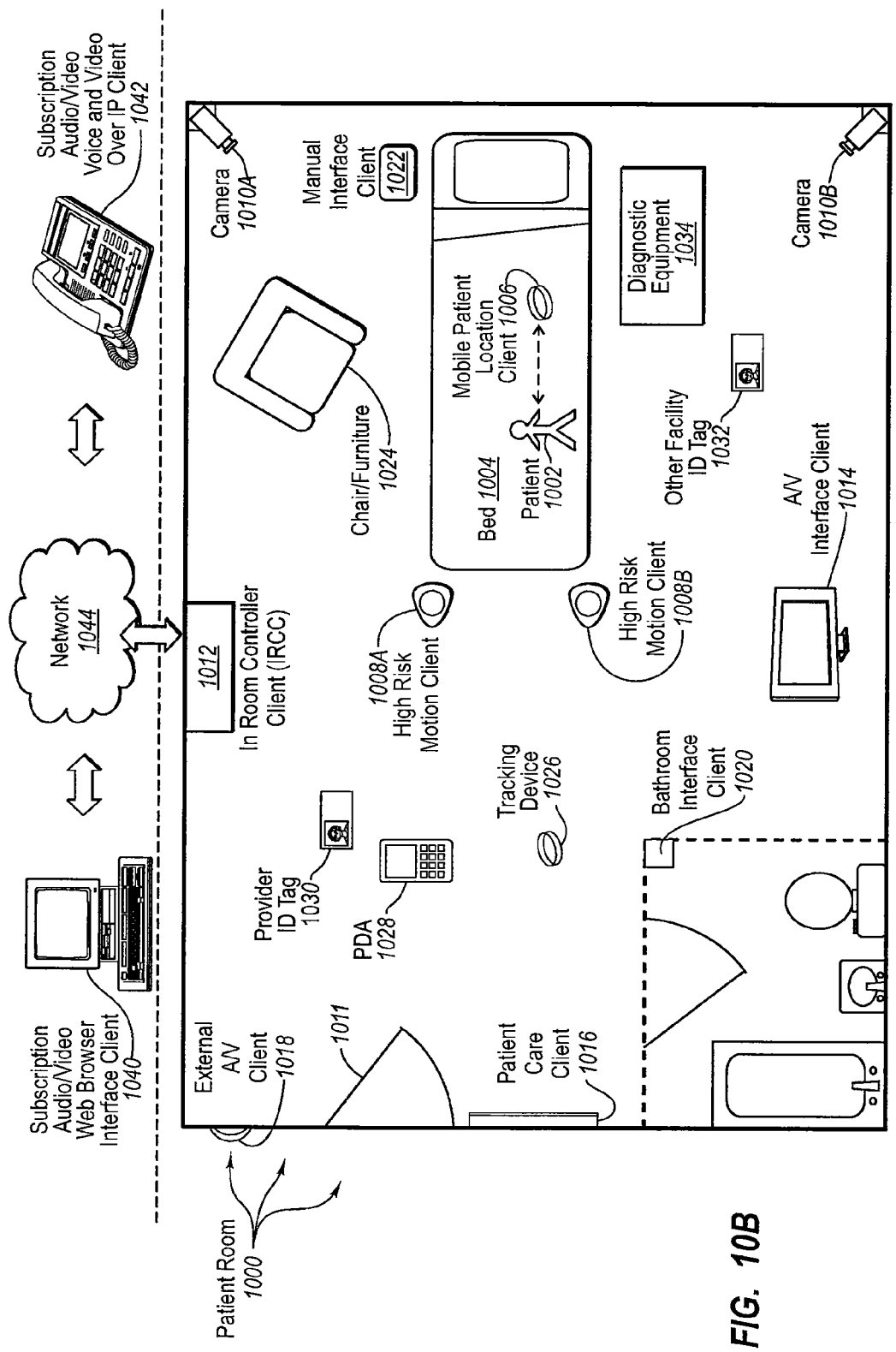

FIGS. 10A and 10B schematically illustrate various embodiments of exemplary patient room configurations used in monitoring a patient and providing one or more responses. In the embodiment of FIG. 10A, an exemplary patient room 1000 is illustrated which includes a patient 1002, a bed 1004 or other support upon which the patient 1002 rests at least some of the time. The patient 1002 may wear or carry a mobile electronic tracking device 1006, such as an RFID bracelet, ultrasound bracelet, or other device. This allows a facility master computer and/or in room controller to identify and track the location of patient 1002 by means of electronic tracking systems known in the art. Tracking device 1006 is specially assigned to patient 1002 and provides verification when patient 1002 is located in room 1000. This facilitates using the correct patient profile when interpreting movements of patient 1002.

One or more overhead cameras 1008 are positioned above the bed 1004 and so as to provide an aerial (e.g., bird's eye) view of patient 1002. One more side or lateral view cameras 1010 are positioned to the side of patient 1002 to provide a different data stream for determining the patient's position and/or movements. Camera 1010 may have a direct or peripheral view of a door 1018 or other entrance to room 1000. An in room controller computer (IRCC) 1012, which may be a local computer located in room 1000, analyzes video data streams generated by cameras 1008, 1010. A flat panel monitor 1014 (e.g., high definition), controller mounted camera 1016, and optionally other devices such as microphones and speakers (not shown) are interfaced with IRCC 1012.

The IRCC 1012 is used to determine the location of the patient's body, including specific body parts, by interpreting video data streams generated by one or more of the cameras 1008, 1010, 1016 and comparing relative distances between the patient's body and fixed locations (e.g., the patient's head and the headboard of the bed, the patient's arms and legs relative to respective left and right bedrails, the height of the patient's torso relative to the bed, etc.). A changing body part position indicates movement of that body part. The IRCC 1012 continuously or periodically compares the location and/or any movements of the patient's body or portion thereof with locations and movements that are predictive of patient bed exiting by that patient as contained in the patient's profile of bed exiting behaviors. Whenever the unique singular or combination of positions, movements, and/or duration of positional actions is detected that is consistent with a unique bed exiting behavior, an appropriate response is initiated.

The flat panel video monitor 1014 can provide multiple functions, including providing normal television programming, recorded programming requested by the patient 1002, video feeds to remote locations (such as loved ones or staff who wish to communicate with patient 1002 remotely), emergency situation instructions and special messages (e.g., patient alerts). The controller mounted camera 1016 provides a direct facial view of the patient and, in combination with video monitor 1014, facilitates two-way A/V communication between patient 1002 and individuals outside room 1000. As shown, the camera 1016 may also have a direct view of door 1018 or other room entrance to monitor entry and exit of individuals (e.g., staff 1042, other patients or visitors) from room 1000. Camera 1016 may also have a view of bathroom door 1020 to monitor movement of patient 1002 to and from the bathroom. A standard motion sensor integrated with conventional video cameras (e.g., camera 1016) may provide motion detection means for detecting room entry or exiting activity. Video data from room viewing video cameras, such as camera 1016, or combinations of room based video cameras, may also be utilized by image analysis programs running within in-room controller 1012 to detect and count the number of individuals within the room. When combined with in-room counts of residents, staff and visitors from RFID data and/or ultrasound data, this information can be used to detect unauthorized entry into patient's room and therefore positively impact patient wellness.

The room 1000 may include other auxiliary devices, such as bedside call button 1022, patient pain scale interface 1023, bathroom call button 1024, microphones/speakers 1025, and bathroom motion sensor 1096. Call buttons 1022, 1024 may comprise those known in the art. The pain scale interface 1023 allows a patient to indicate to the monitoring system (e.g., IRCC 1012, facility master, and/or nursing station) the patient's current pain level (e.g., on a scale of 1 to 10, with 1 being the least and 10 being the most pain). Motion sensor 1096 can be used, e.g., in combination with camera 1016, call button 1024 and/or microphones/speakers 1025, to determine whether a patient 1002 requires further assistance while in the bathroom. An RFID grid or ultrasound grid set up throughout the room can be used to monitor the position and/or movements of the patient 1002 when not resting on the bed 1004 and also the position and/or movements of staff 1042, other persons such as patients, friends, family or other visitors, and assets (not shown).

FIG. 10B illustrates an exemplary patient room 1000 which includes a patient 1002, a bed 1004 or other support upon which the patient 1002 rests at least some of the time, and various other devices used to monitor the patient and the patient's room 1000. The patient 1002 may wear or carry a mobile electronic tracking device 1006. This allows a facility master computer to identify and track the location of the patient 1002 by means of electronic tracking systems known in the art. Tracking device 1006 may be a conventional RFID or ultrasound device (e.g., bracelet) and may be equipped with a patient emergency call or panic button (not shown) as known in the art. Tracking device 1006 is specially assigned (and attached) to patient 1002 staying in patient room 1000. Tracking device 1006 provides verification that patient 1002 is actually located in room 1000. This facilitates using the correct patient profile when interpreting movements of patient 1002 rather than those of another patient.

High risk motion clients 1008A and 1008B (e.g., which include one or more of cameras, electronic motion sensors, electric eyes, RFID detectors, ultrasound detectors, etc.) may be positioned on either side of bed 1004, thus providing two separate data streams for interpretation of the patient's position and/or movements. Side cameras 1010A and 1010B are positioned on either side of patient 1002 to provide additional data streams for interpretation of the patient's position and/or movements. At least one of cameras 1010A and 1010B may have a direct or peripheral view of a door 1011 or other entrance to room 1000. An in room controller client (IRCC) 1012, which can be a local computer located in or near room 1000, at least partially controls motion clients 1008A and 1008B, cameras 1010A and 1010B, and other electronic devices in room 1000. IRCC 1012 also analyzes video data generated by cameras 1008, 1010 in order to identify behavior of patient 1002 that may be predictive of support exiting.

Other electronic devices include an in-room A/V interface client 1014, which can be used to establish one- or two-way communication with patient 1002, patient care client 1016, external A/V client 1018 (e.g., in a hallway), bathroom interface 1020 (e.g., call button, microphone and/or speaker), and manual patient interface client 1022 (e.g., a call button, pain scale dial, etc.). The room is shown having a chair 1024 or other furniture (e.g., wheel chair), upon which visitors or even the patient may rest at least some of the time. The monitoring system can be used to detect potential support exiting by patient 1002 of chair/furniture 1024 in addition to bed 1004.

The IRCC 1012 and electronic devices in room 1000 can interoperate to implement the principles of the present invention. High risk motion clients 1008A and 1008B, either alone or in combination with one or both of cameras 110A and 1010B, can monitor a patient's movements in bed 1004 and/or chair or other furniture 1024. Generally, a patient's movement on a bed or other support can be monitored through a grid monitoring system ("GMS") that identifies patient vertical and horizontal movements that may be indicative of an attempt to exit the furniture. The time a body part is located within a critical zone and/or changes in position and/or changes in speed can all be determined. The GMS can also utilize pressure, temperature, and other distributed sensors located within a bed or other furniture or directly attached to a patient. Inputs from the various clients and sensors in room 1000 can be provided to the IRCC 1012 and/or facility master (not shown). In addition, any of cameras 1010A, 1010B or 1020, as well as motion clients 1008A and 1008B, can monitor a patient's position and/or movements within room 1000 when the patient is not resting on a bed 1004, chair 1024 or other support located in room 1000.

Upon activation of the GMS or other high risk motions clients, in room controller client 1012 and/or a facility master utilizes patient management software to initiate and establish responsive actions. For example, upon detecting activities that predict an unattended support exit, in room controller 1012 and/or a facility master can establish a real time A/V connection with a central station (e.g., nurse's) and/or one or more mobile caregiver clients (e.g., PDAs carried by responder caregivers). Further, in room controller client 1012 and/or a facility master can activate external A/V client 1018 (e.g., an alarm in a hallway) and/or initiate archiving of data from one or more of high risk motion clients 1008A and 1008B, and cameras 1010A, 1010B and 1020 upon the occurrence of a support exiting event or other pre-established triggering event.

FIG. 10B further depicts a provider tracking device 1026 (e.g., an RFID or ultrasound device), a provider PDA 1028, a provider ID tag 1030 (e.g., an RFID or ultrasound device), other facility ID tag 1032 (e.g., an RFID or ultrasound device), and/or diagnostic equipment 1034 which have entered room 1000. Each of these devices can communicate with IRCC 1012 and/or a system-wide tracking system that communicates direct to a facility master computer (not shown) via various appropriate protocols (e.g., RF, IEEE 802.11 group, IEEE 802.15.4, etc.). IRCC 1012 can update pertinent patient information, such as, for example, provider ID, other personnel ID or diagnostic equipment and time of entry. Detecting the presence of personnel and devices inside room 1000 indicates that facility personnel and/or assets associated with these devices have likely entered room 1000, for example, in response to a predicted support exiting event, a patient initiated alarm, prescribed patient activities, and the like.

According to one embodiment, patient room 1000 may be networked with other components including, for example, subscription clients (e.g., subscription A/V web browser interface client 1040 and subscription A/V voice and video over IP client 1042), which are connected to in room controller client 1012 by means of network 1044. Subscriber clients 1040 and 1042 can be located at or external to a healthcare facility. Thus, providers in diverse locations can be notified of actionable events occurring inside patient room 1000.

Figure 11A:
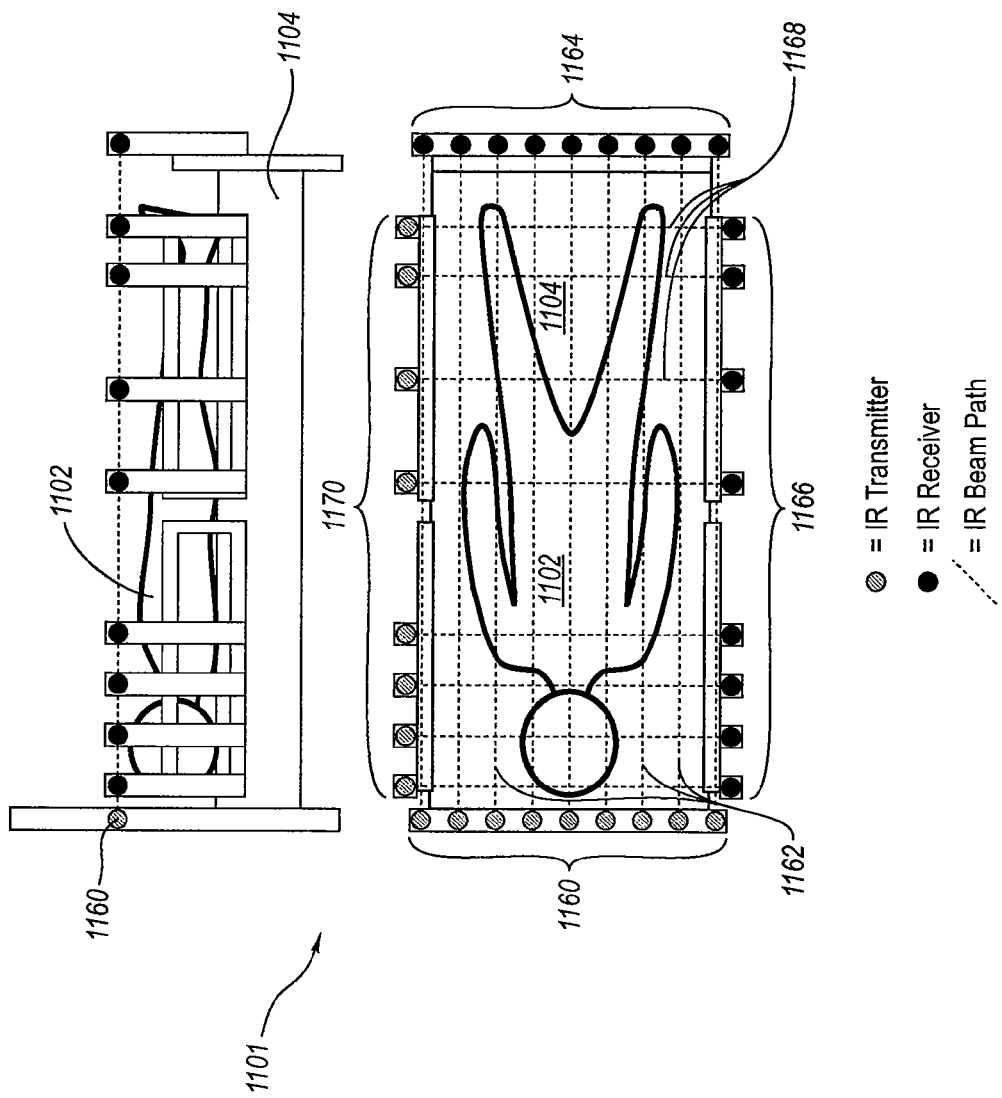
FIGS. 11A and 11B schematically illustrate alternative patient support exiting detection systems.

FIG. 11A illustrates an alternative embodiment for detecting patient support exiting behavior comprising a light beam matrix system 1101, which may be used instead of or in addition to one or more cameras used to determine patient position and/or movements. Exemplary light beam matrix system 1101 includes a patient 1102 resting on a bed 1104 or other support. A plurality of light transmitters 1160 are positioned at one side of bed or other support 1104 and generate first beams of light 1162, which are detected by corresponding first light receivers 1164. A plurality of second light transmitters 1166 are positioned laterally relative to first light transmitters 1160 and generate second beams of light 1168, which are detected by corresponding second light receivers 1170. Beams of light 1162, 1168 may comprise IR, visible or UV wavelengths.

First and second beams of light 1162, 1168 may be positioned above the patient 1102 and cross-cross to form a light beam matrix that is able to detect patient location and/or movement in multiple (e.g., three) dimensions. The closer together the light beams, the finer the detection of patient position and/or movement. According to one embodiment, the light beams are spaced apart at intervals ranging from six (6) inches to two (2) feet (e.g., at one (1) foot intervals). As long as the patient 1102 rests flat on the bed or other support 1104 or is otherwise below the light beam matrix comprising first and second light beams 1162, 1168, no beams of light are blocked or interrupted such that no movement is detected. Interrupting and/or resuming one or more beams of light may be indicative up upward and/or downward movement(s). Sequentially interrupting and/or resuming one or more of first light beams 1162 may be indicative of lateral movement(s). Sequentially interrupting and/or resuming one or more of second light beams 1162 may be indicative of longitudinal movement(s).

A computer system (not shown) interprets data generated by the light beam matrix. Continuous light detection by the light sensors may be interpreted as a series of 1 s (or 0 s) in computer language. Any interruption or blocking of a light beam corresponds to a series of 0 s (or 1 s) in computer language and is indicative of a body part being positioned between one or more particular light transmitters and detectors. Because bed exiting, for example, involves at least some lifting of the patient's body (e.g., to get over bed rails or pass through a narrow passage in a bed rail), actual lifting of the patient's body will typically block or interrupt at least one light beam. Depending on which light beams are interrupted and/or the sequence of such interruption, the computer can determine which parts of the patient's body have raised and/or moved. Sequentially interrupting multiple beams typically indicates movement (i.e., lateral, longitudinal, upward and/or downward depending on which sequence of beams are interrupted). The patient's movements, as detected by the light beam matrix and interpreted by the computer system, are compared to a patient profile of positions and/or movements that are predictive of support exiting by that patient. If potential patient support exiting is detected, an appropriate response can be initiated.

Figure 11B:
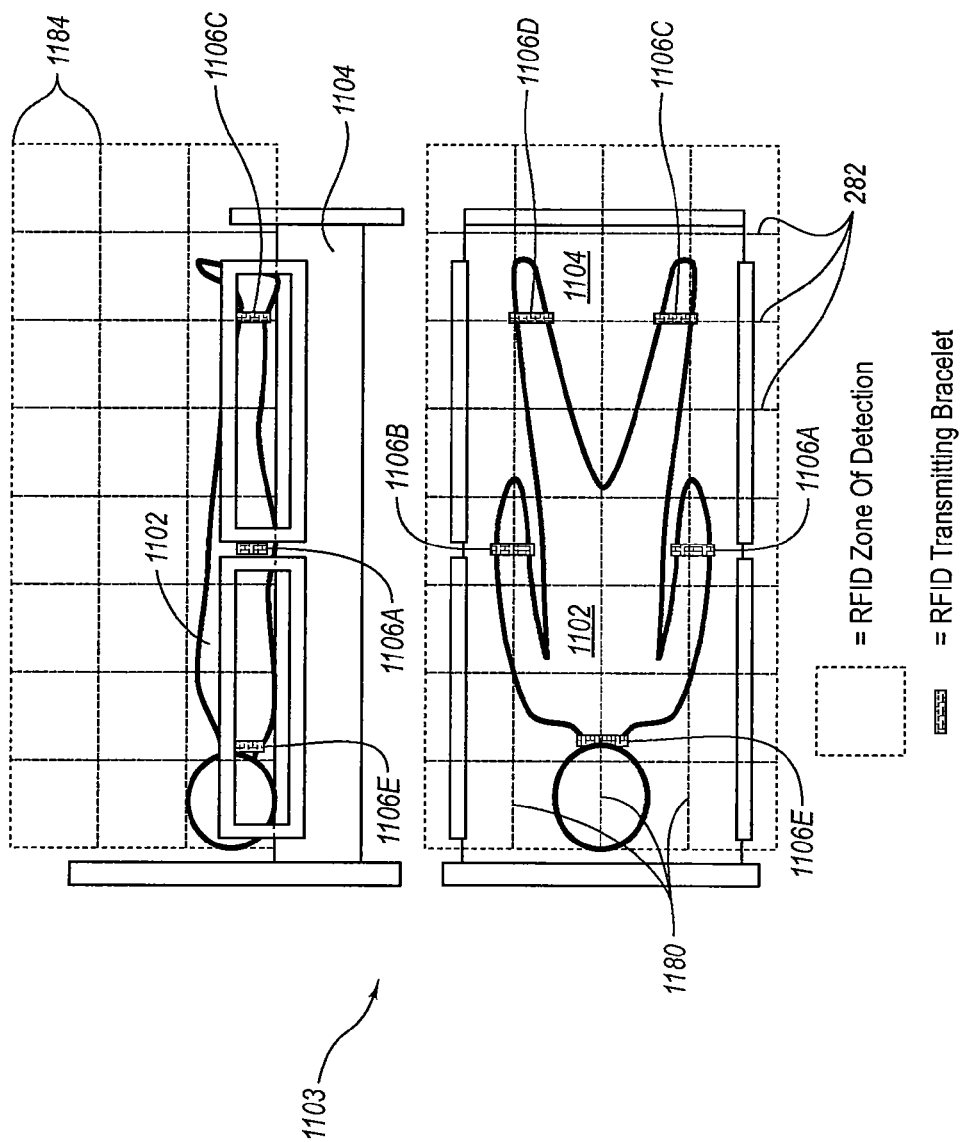

FIG. 11B illustrates an alternative embodiment for detecting patient support exiting behavior comprising a small zone RFID grid system 1103, which may be used instead of or in addition to one or more cameras used to determine patient position and/or movements. Exemplary RFID grid system 1103 includes a patient 1102 resting on a bed 1104 or other support. The patient's body may be equipped with any appropriate number of RFID devices that are located so as to detect patient positions and/or movements associated with support exiting (e.g., right RFID wrist device 1106A, left RFID wrist device 1106B, right RFID ankle device 1106C, left RFID ankle device 1106D, and neck RFID device 1106E). Each RFID device can be separately encoded to represent a specific body part of the patient to distinguish between positions and movements of the different body parts.

The RFID grid system 1103 includes a three-dimensional grid of small, cube-like RFID zones defined by a plurality of RFID detectors positioned along lateral zone boundaries 1180, longitudinal zone boundaries 1182, and elevation zone boundaries 1184. The closer together the RFID detectors, the finer the detection of patient position and/or movement. According to one embodiment, the RFID detectors are spaced apart at intervals ranging from six (6) inches to two (2) feet (e.g., at one (1) foot intervals). The grid of RFID zones is able to detect three-dimensional patient position and/or movements as approximated by the positions and/or movements of the RFID devices 1106 worn by the patient in or through the RFID zones.

A computer system (not shown) interprets data generated by the small zone RFID grid as it detects the position and/or movement of the RFID devices 1106 attached to the patient 1102. Depending on which RFID zone is occupied by a specific RFID device and/or which RFID device(s) may be moving between RFID zones, the computer can determine the position and/or location of corresponding body parts of the patient. If potential patient support exiting is detected, an appropriate response can be initiated.

A similarly configured ultrasound grid system can also be used to implement the functionality depicted in FIG. 11B. A patient's body may be equipped with any appropriate number of ultrasound devices that are located so as to detect patient positions and/or movements associated with support exiting. Each ultrasound device can be separately encoded to represent a specific body part of the patient to distinguish between positions and movements of the different body parts.

Thus, an ultrasound grid system can also include a three-dimensional grid of small, cube-like ultrasound zones defined by a plurality of ultrasound detectors positioned along lateral zone boundaries 1180, longitudinal zone boundaries 1182, and elevation zone boundaries 1184. The closer together the ultrasound detectors, the finer the detection of patient position and/or movement. According to one embodiment, the ultrasound detectors are spaced apart at intervals ranging from six (6) inches to two (2) feet (e.g., at one (1) foot intervals). The grid of ultrasound zones is able to detect three-dimensional patient position and/or movements as approximated by the positions and/or movements of the ultrasound devices worn by the patient in or through the ultrasound zones.

Accordingly, a computer system (not shown) can interpret data generated by the small zone ultrasound grid as it detects the position and/or movement of the ultrasound devices attached to the patient 1102. Depending on which ultrasound zone is occupied by a specific ultrasound device and/or which ultrasound device(s) may be moving between ultrasound zones, the computer can determine the position and/or location of corresponding body parts of the patient. If potential patient support exiting is detected, an appropriate response can be initiated.

Figure 12:
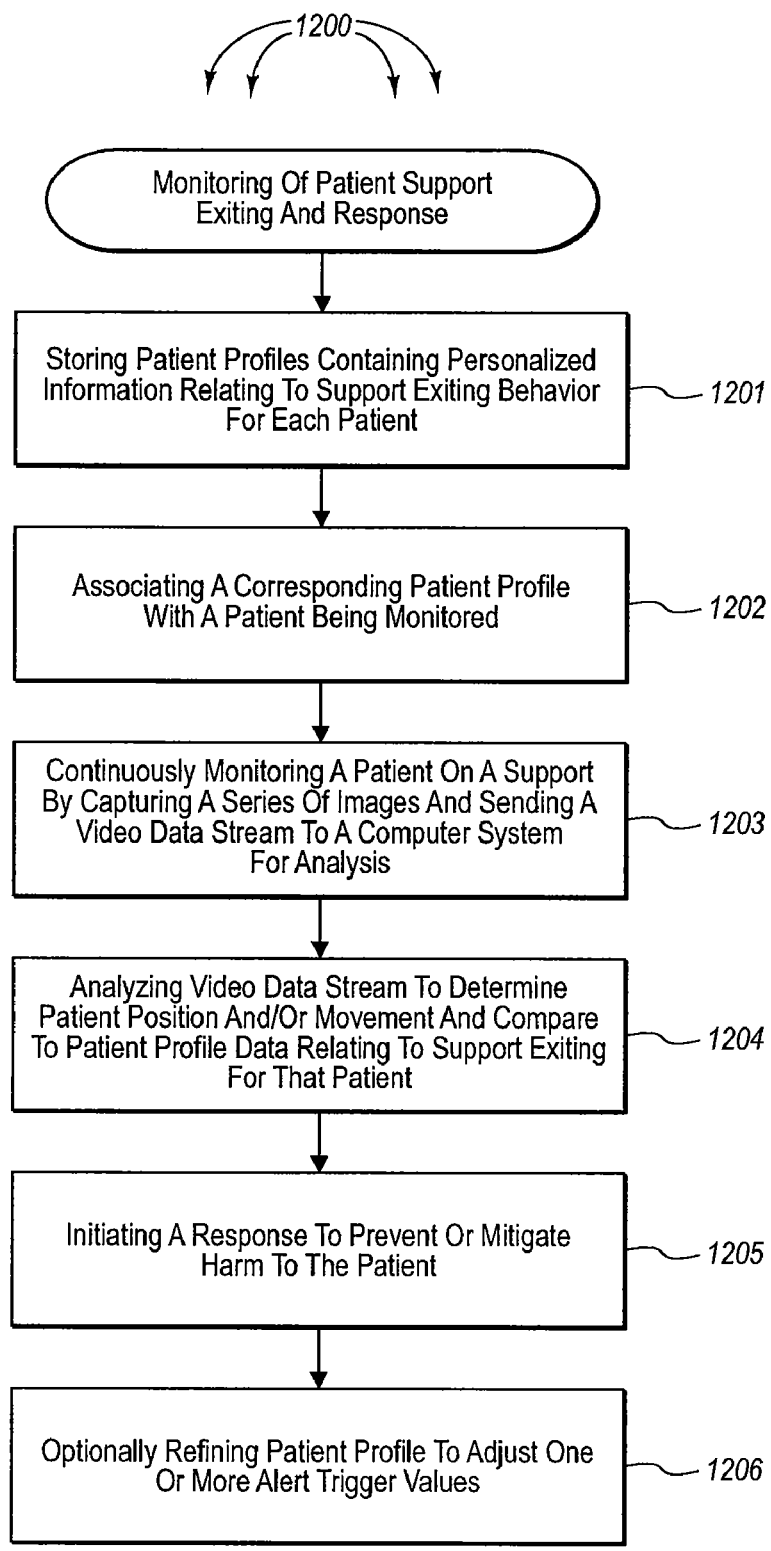
FIG. 12 is a flow chart that illustrates an exemplary method for monitoring a patient on a support, detecting possible support exiting, and initiating a response to prevent or mitigate patient harm.

FIG. 12 is a flow chart that schematically illustrates an exemplary method 1200 of monitoring a patient in order to detect support exiting and initiate a response in the event of predicted support exiting. This method may be carried out at least in part using the exemplary patient monitoring systems illustrated in FIGS. 3, 9, 10A-B and 11A-B discussed above and/or systems illustrated or discussed elsewhere in this disclosure and/or systems or components known in the art. A first act or step 1201 involves creating or obtaining a plurality of patient profiles, each containing personalized information relating to support exiting behavior for each patient.

Examples of known bed exiting behaviors that have been observed as being used by one or more patients include, but are not limited to: (1) bed slide method (e.g., sliding down towards the bottom of the bed); (2) right side rail roll method; (3) left side rail roll method; (4) torso angle up and leg swing right method; (5) torso angle up and leg swing left method; (6) torso angle up and upper body roll right method; and (7) torso angle up and upper body roll left method. A given patient may utilize one or more of the foregoing methods or a variation thereof, but typically one will dominate. Other support exiting behaviors are possible and can be accounted for where relevant.

Figure 13:
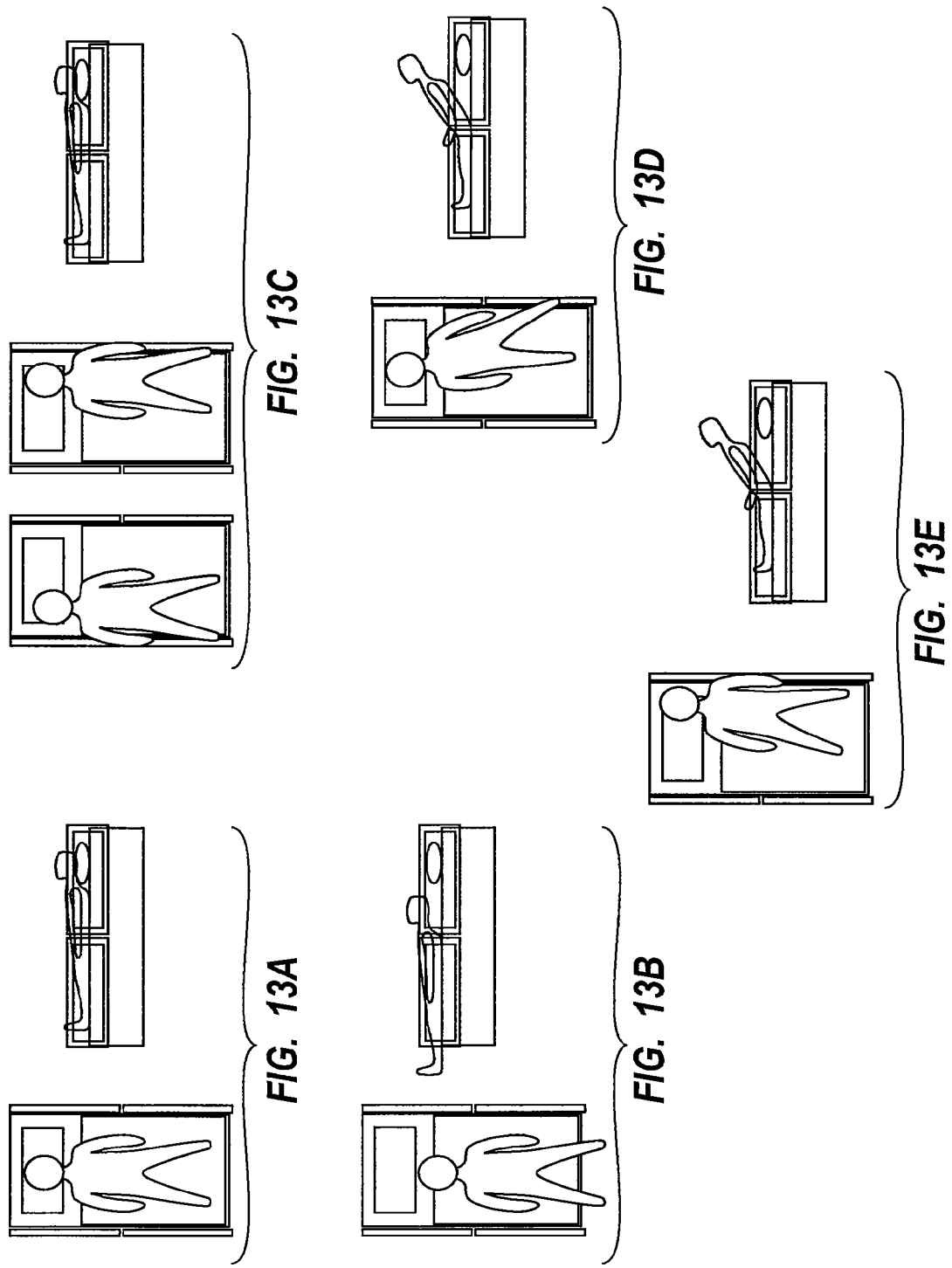
FIGS. 13A-13E schematically depict a patient in various exemplary positions on a bed relative to known bed exiting behaviors.

Reference is now made to FIGS. 13A-13E which illustrate exemplary patient behaviors as they relate to normal resting and bed exiting. FIG. 13A schematically illustrates a normal resting position of a patient lying flat on a bed. FIGS. 13B-13E schematically illustrate positions associated with various bed exiting positions, movements or behaviors. FIG. 13B roughly depicts the position of a patient that has engaged in the bed slide method of bed exiting. A notable feature is the distance between the patient's head and the pillow or headboard. FIG. 13C roughly depicts left and right side rail roll methods in which the patient's body moves to the side or left side rail preparatory to bed exiting. FIG. 13D illustrates the torso up and leg swing left method of bed exiting, which is characterized by upward movement of the torso coupled with movement of the left leg toward the edge of the bed. The torso up and right leg swing method is simply the mirror image of that shown in FIG. 13D. FIG. 13E illustrates the torso up and upper body roll left method, which is characterized by the patient's torso moving upward and the patient's body rolling to the left. The torso up and upper body roll right method would be the mirror image of that shown in FIG. 13E.

Each patient profile contains one or more spatial parameters or limits associated with the one or more support exiting behaviors that are known for each patient. The spatial parameters or limits relating to bed exiting may include data points pertaining to one or more of the seven common bed exiting behaviors noted above. Image parameters relating to exiting of other supports can be tailored to behaviors that are typical for patients exiting such supports. Patient profiles may include idiosyncratic information that is specific to a particular individual (e.g., base on patient height, weight, speed of movement, length of limbs, number of operable limbs, and/or personal habits of position and/or movement while support exiting).

By way of example, as illustrated a spatial parameter that corresponds to the bed slide method of bed exiting is the distance from a head feature to the top of the bed (e.g., headboard) (see FIG. 13B). Spatial parameters corresponding to the side rail roll methods (left or right) for bed exiting include: (a) the torso positioned primarily to the right or left of the bed and (b) the hand and/or arm on or over (i.e., covering or blocking the view of) the left or right bed rail for a given period of time (see FIG. 13C). Spatial parameters corresponding to the torso up and leg swing methods (left or right) of bed exiting include: (a) the head elevated from a flat position and (b) right or left legs and/or feet breaking a vertical bed edge plane (see FIG. 13D). Spatial parameters corresponding to the torso up and upper body roll methods (left or right) of bed exiting include: (a) the head elevated from a flat position; (b) torso positioned primarily to the right or left portion of the bed; and one or both of ($c_1$) the left or right hand and/or arm on or over (i.e., covering or blocking the view of) the left or right bed rail for a given period of time and/or ($c_2$) the head breaking a vertical plane of the left or right side rail (see FIG. 13E). In addition to patient body position, time of duration of a limb or body part at a specified location relative to a critical region of the support may also play a roll in determining bed or other support exiting.

Referring back to FIG. 12, a second act or step 1202 of method 1200 involves associating a corresponding patient profile with the particular patient being monitored. The use of RFID, ultrasound, or other patient identification and tracking devices may assist in identifying which patient profile corresponds to the patient being monitored. For example, if a patient moves from room to room over time, different monitoring equipment in the various rooms can all monitor the same patient at different times, while comparing patient position and/or movements with specific profile data for that patient, because the patient is associated with a patient identification and tracking device that emits a uniquely encoded signal. Such association may alternatively be made (e.g., entered manually into a computer) by hospital staff whenever a patient occupies a particular room.

A third act or step 1203 of method 1200 involves continuously monitoring a patient resting on a support by capturing a series of images of the patient and surroundings and sending a data stream (e.g., video feed) to a computer system for analysis. Since both motion video recording devices and still photo devices are capable of taking individual frames, the distinction between the two is simply the speed with which individual frames are taken (i.e., the time interval between frames). Thus, both motion video recording devices and still photo devices can be used to send a continuous data stream to the analyzing computer system.

A fourth act or step 1204 of method 1200 involves analyzing the data stream (e.g., frames of video data) to determine patient position and/or movement and comparing them to patient profile data relating to the support exiting behavior of that patient. As discussed above, such computer-implemented analysis of position and/or movement may be carried out using a grid monitoring system (GMS), which compares the relative position of one or more body parts in relation to stationary background objects, such as critical or predefined support zones. The use of patient specific profiles enables the computer system to more accurately detect and distinguish between behaviors that are indicative or predictive of patient support exiting and those which are not as compared to methods that are not patient specific but utilize the same sets of analytical limits for all patients. In this way, the incidences of false positives and false negatives are significantly reduced or substantially eliminated.

In the event that behavior consistent with predicted support exiting is detected, a fifth act or step 1205 of method 1200 is triggered. Step 1205 includes initiating an appropriate response in an attempt to prevent or mitigate harm to the patient. Exemplary responses include sending an alarm and/or video feed to a nursing station, alerting the patient of potential viewing, establishing one- or two-way communication between the patient, sending a pre-recorded message to the patient, sending notification to a nearby caregiver who can provide direct physical intervention, sounding an alarm, and the like. It may even be appropriate in some cases to activate an automated restraint device that is able to keep the patient from exiting the support until a caregiver is able to arrive and provide assistance.

The method optionally includes an act or step 1206 of refining the patient's profile to adjust one or more alert triggers to reflect monitored bed exiting behavior. In this way, the profile may be progressively refined to reflect a patient's historical support exiting behavior as monitored over time. This would be expected to decrease the overall number of false positives and false negatives, which would tend to increase the accuracy and efficiency of responding to potential support exiting behaviors on the part of the patient.

Figure 14:
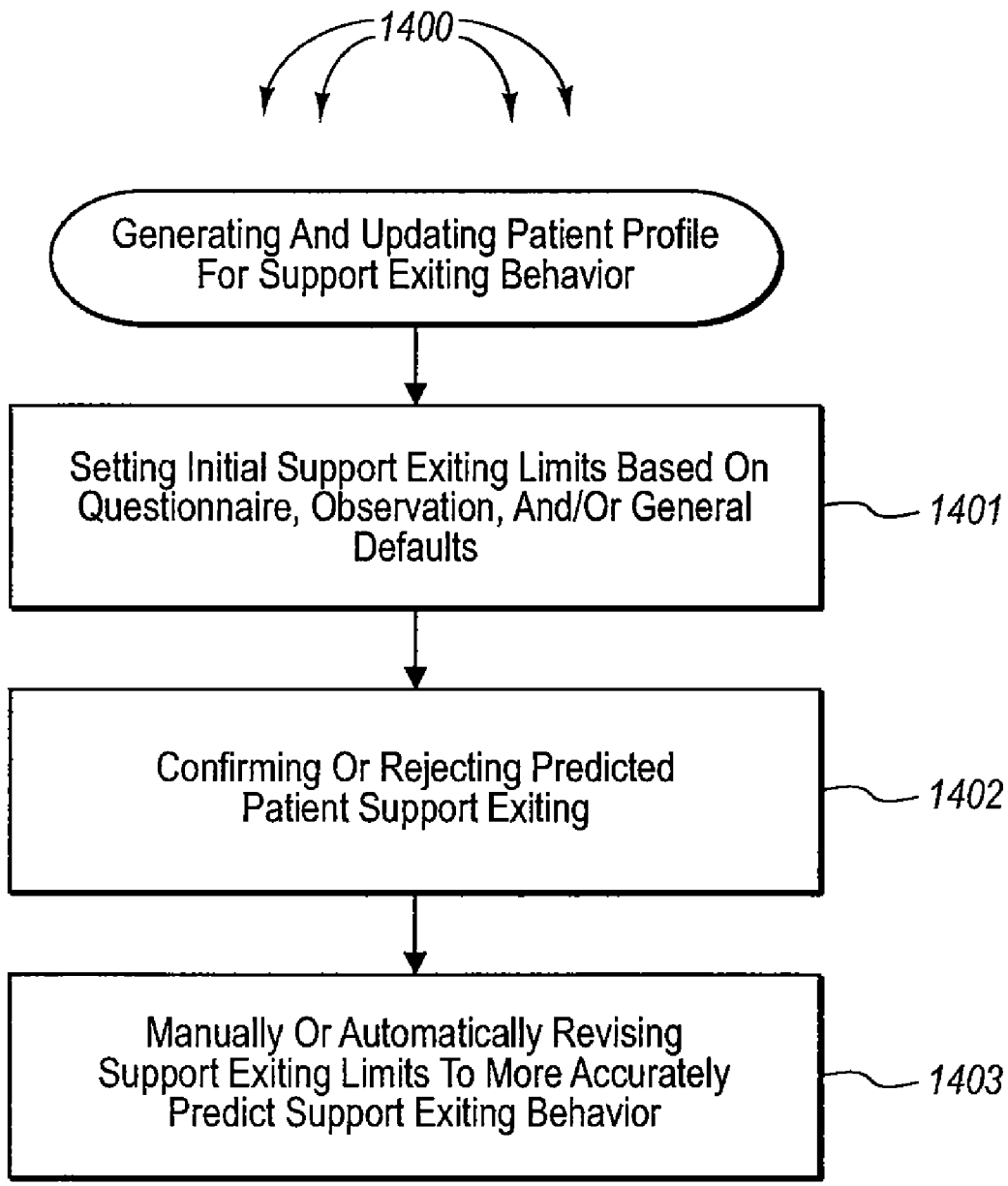
FIG. 14 is a flow chart that illustrates an exemplary method for generating and updating a patient profile that contains data relating to support exiting behavior of that patient.

FIG. 14 is a flow chart that schematically illustrates an exemplary method or sub-routine 1400 of generating and updating a patient profile for support exiting behavior. A first act or step 1401 involves setting initial support exiting limits based on information learned from or about the patient (e.g., as a result of a patient or relative completed questionnaire, observation by a qualified provider, general defaults, and the like). It is understand that the initial limits are advantageously modified as more information is gathered over time regarding a patient's actual support exiting habits while at one or more facilities.

Accordingly, a second act or step 1402 includes actually monitoring a patient while resting on a support as discussed above and then either confirming or rejecting an alert of predicted patient support exiting. From one or more confirmations or rejections of predicted bed exiting, additional information regarding the specific support exiting habits of the patient can be learned. Act or step 1402 may form part of an information feedback loop for recursively refining patient profile data.

A third act or step 1403 includes manually or automatically revising or updating previously set support exiting limits in order to more accurately predict support exiting behavior by patient in question. In some cases, the computer system may appropriately alter patient profile data and limits relating to bed exiting so long as it does not substantially increase the risk of unassisted support exiting. In other cases, patient profile data and limits relating to bed exiting may be altered manually by a qualified individual or committee who analyzes data generated during predicted support exiting events. Limits can be established initially, or pre-existing limits may be tightened or loosened, in response to incidences of false positives and/or false negatives relative to support exiting.

Figure 15:
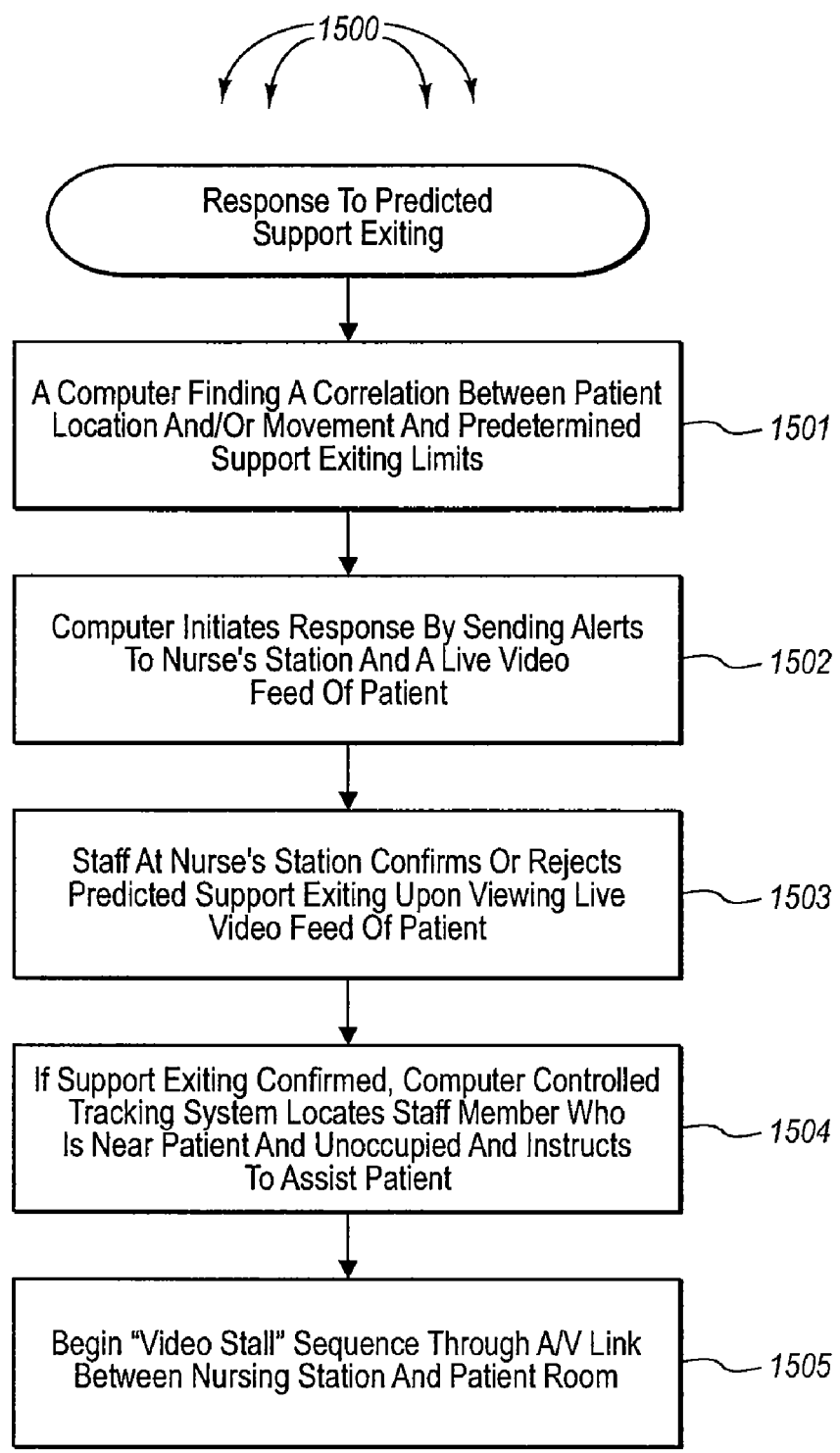
FIG. 15 is a flow chart that illustrates an exemplary method for responding to a computer predicted support exiting event.

FIG. 15 is a flow chart that schematically illustrates an exemplary method or sub-routine 1500 of responding to predicted patient support exiting. In a first act or step 1501, a computer system finds a correlation between a patient's location and/or movements and predetermined limits for that patient contained in or derived from a patient specific profile. A second act or step 1502 involves a computer initiating a response by sending an alert to both the patient's room (to warn of a breech in privacy) and a nursing station along with a live (i.e., real time) video feed of the patient's room to the nursing station. In a third act or step 1503, a staff member at the nursing station confirms or rejects the predicted support exiting upon viewing the live video feed of the patient's room. In a fourth act or step 1504, if support exiting is confirmed, a computer-controlled tracking system locates an unoccupied staff member who is assigned and/or near the patient's room and instructs the staff member to assist the patient.

Figure 16:
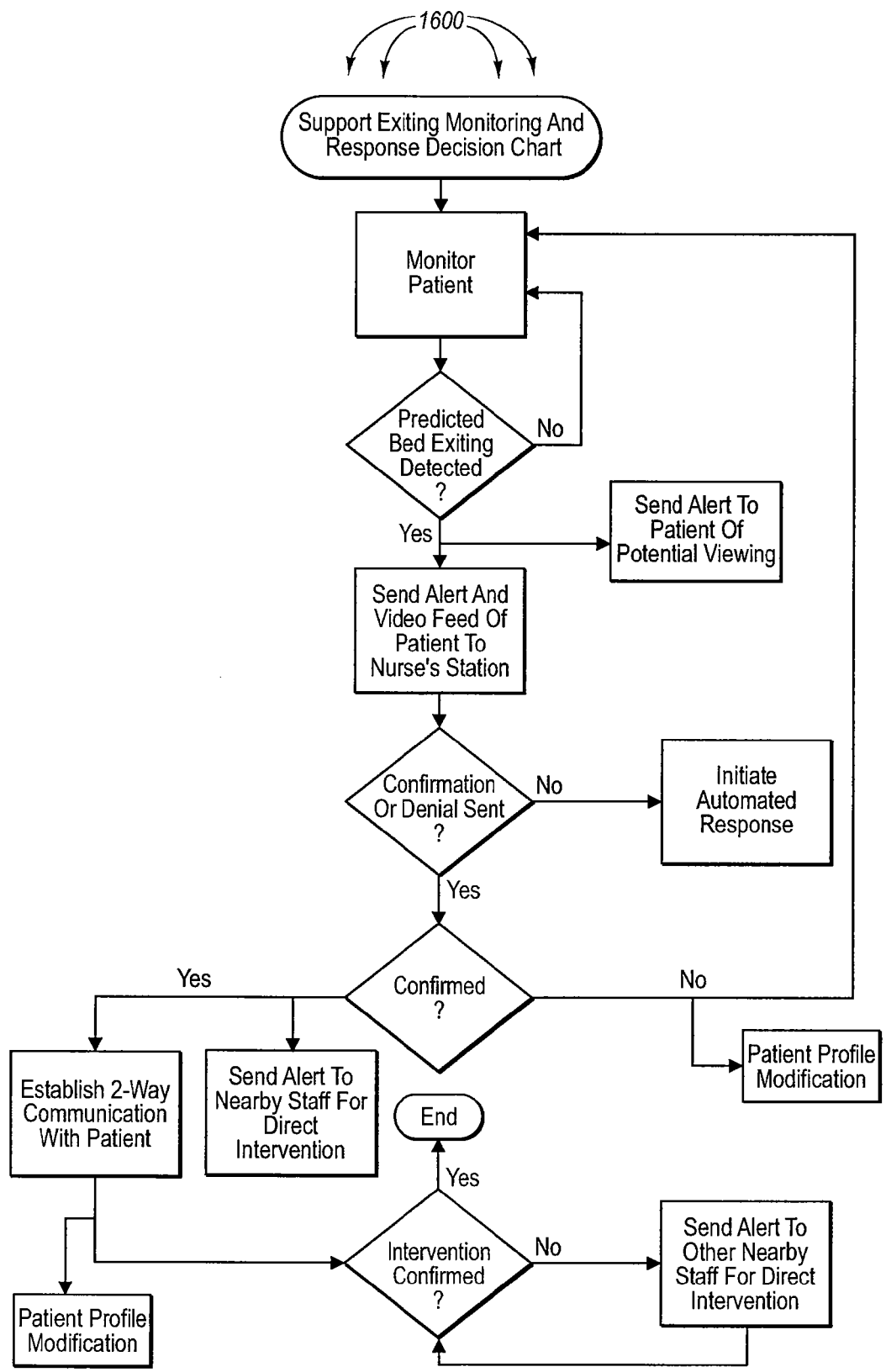
FIG. 16 is a decision chart that illustrates an exemplary decision sequence for responding to an alert of predicted bed exiting.

FIG. 16 is a flow chart that schematically illustrates an exemplary monitoring and response decision chart 1600 relative to bed exiting. The patient is continuously or periodically monitored, and the patient's position and/or movements are analyzed. As long as positions and/or movements predictive of bed exiting are not detected, monitoring continues. Of course, monitoring may also continue even after bed exiting is predicted in order to send a live video feed to a central station and/or determine an escalation of events.

If predicted patient bed existing is detected by the analyzing computer system, an alert is sent to a nursing station as well as a live video feed of the patient for verification of actual bed exiting. Prior to or at the same time, an alert is sent to the patient's room of potential third party viewing of the patient (e.g., to protect patient privacy). If no verification (i.e., confirmation or denial) is sent to the computer system within a predetermined time period, an automated response is initiated. If verification is sent, the computer determines whether bed exiting is confirmed or denied. If bed exiting is denied, the computer system resumes normal patient monitoring. If bed exiting is confirmed, further intervention is initiated.

The escalation of intervention to assist a patient who is in the process of bed exiting may include establishing one- or two-way communication between the confirming staff member and the patient. It may also include sending an alert to a nearby or assigned staff member for direct physical intervention. An RFID, ultrasound, or other tracking device can be used to verify that physical intervention was carried out as prescribed. The assisting caregiver may press a confirm button on a patient care interface device connected to the computer system, or the caregiver may provide oral confirmation to the staff member at the nursing station. The staff member at the nursing station may view the live video feed from the patient's room to confirm successful intervention. If intervention is confirmed, the response is complete. If intervention is not confirmed, the response may include sending one or more additional alerts to other nearby staff members for direct physical intervention.

V. Examples of Other Methods and Systems for Enhancing Quality and Performance at a Facility

A. Providing Patient Assistance

Figure 17:
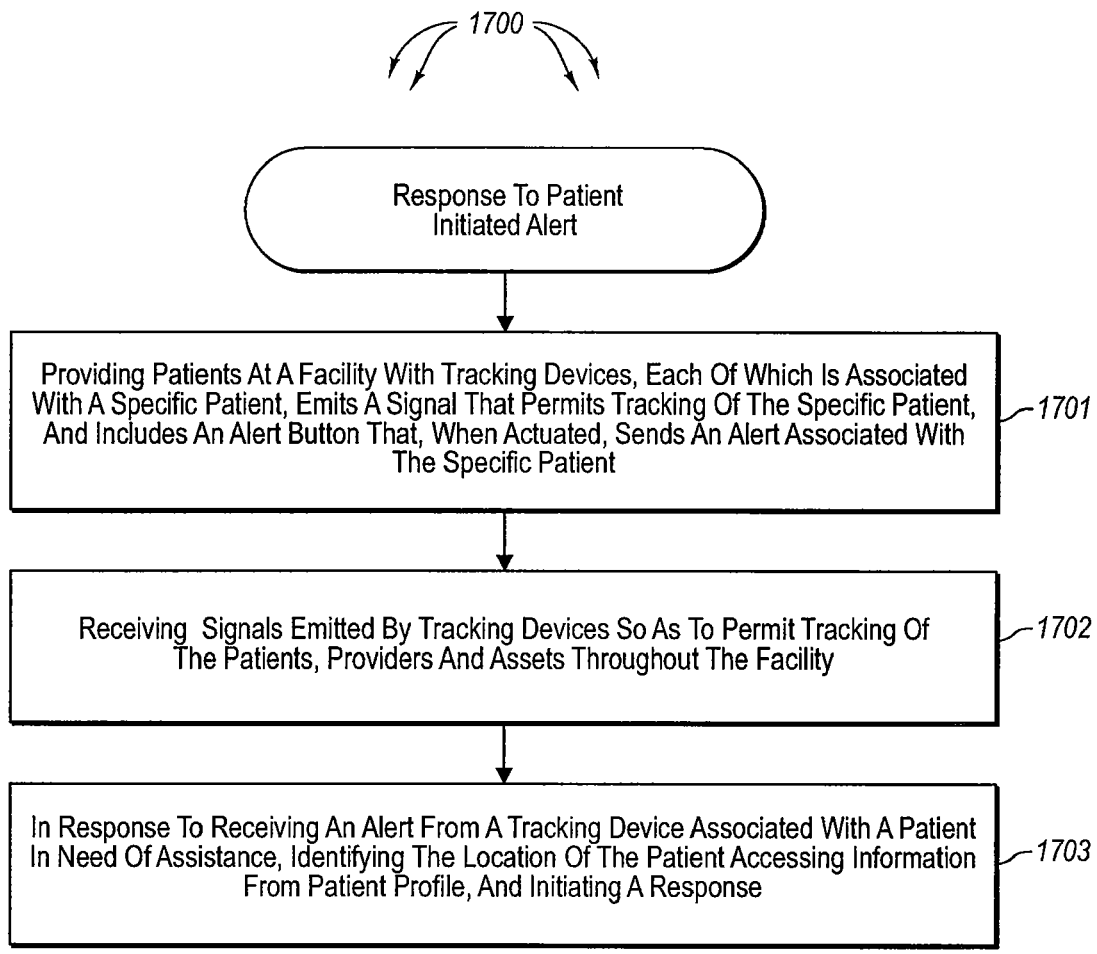
FIG. 17 is a flow chart that illustrates an exemplary method for providing an automated response to a patient initiated alert.

FIG. 17 a flow chart which illustrates an exemplary method 1700 for responding to patient alerts and providing assistance for a patient in need thereof. Method 1700 will be described with respect to the components and data in system architecture 300 (FIG. 3). Method 1700 includes an act 1701 of providing the patients of a facility with tracking devices, each of which is associated with a specific patient, emits a signal that permits tracking of the specific patient, and includes an alert button that, when actuated, sends an alert associated with the specific patient. For example, as previously described, a patient staying in a room at the facility can be provided with a mobile patient location bracelet specifically assigned to the patient. A tracking device can transmit any of a variety of different type signals, such as, for example, RFID signals or ultrasound signals.

Method 1700 includes an act 1702 of receiving one or more signals emitted by one or more tracking devices so as to track the location of patients throughout the facility. For example, sensing devices 312 within the facility can receive an RFID signal, an ultrasound signal, an alarm signal, etc. from each mobile patient location bracelet. Each patient can be tracked and located in patient rooms and also throughout hallways, other common areas, and dangerous or otherwise restricted areas of a healthcare facility. Signals can be detected by RFID sensors and/or ultrasound sensors throughout a facility and relayed to computer systems that process the signals to generate appropriate electronic messages and notifications.

Method 1700 includes an act 1703 that includes, in response to receiving an alert from a tracking device associated with a patient in need of assistance, identifying the location of the patient, accessing relevant information from the patient's profile, and initiating a response (e.g., a patient specific response that can optionally be tailored based on information in the patient's profile, such as the most critical medical conditions of the patient requesting help). For example, in response to receiving an alert from a mobile patient location bracelet, the location of an assigned or nearby caregiver can be identified and appropriate physical intervention can be initiated. The intervention may be different for different patients based on their respective profiles and medical conditions. A computer system that processes the signal (e.g., an in room controller client or facility master) can generate an electronic message or notification that is sent to one or more other electronic devices corresponding to assigned or nearby healthcare providers (e.g., to computer system 301*c*, PDA 309, PDA 309, etc.)

In response to using the alert feature, patient profiles can be updated to count the number of times each patient has initiated an authorized alert (e.g., an actual physical or medical emergency) versus an unauthorized alert (e.g., ordering room service, socializing, horseplay, etc.). In order to provide for the specific needs of a patient, patient profiles data can be accessed and a predetermined or specially tailored response initiated (e.g., in the case of patients with special needs).

B. Selectively Archiving Patient Video Recordings

Figure 18:
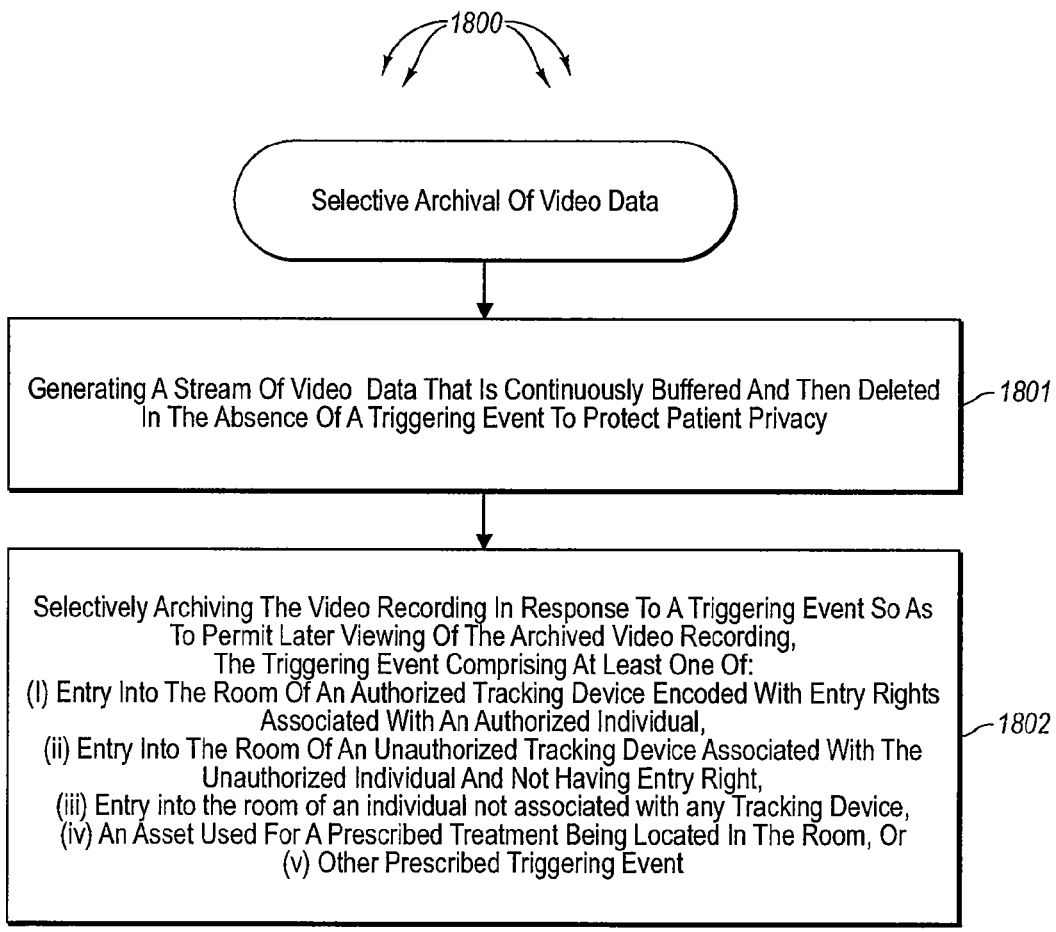
FIG. 18 is a flow chart that illustrates an exemplary method for selective archiving of a video data stream of a patient in response to a triggering event.

FIG. 18 is a flow chart that illustrates an exemplary method 1800 for selectively archiving a video recording of a patient in response to a triggering event. Method 1800 will be described with respect to the components in a typical patient room (e.g., room 1000 of FIGS. 10A and 10B).

Method 1800 includes an act 1801 of generating a video data stream of a patient's room at a healthcare facility, wherein the video data stream is continuously buffered and then deleted in the absence of a triggering event such that the buffered and deleted video recording is normally never viewed by an individual in order to protect patient privacy. For example, a computer system can use a circular buffer of a specified size such that after a prescribed amount of time (e.g., 3 to 5 minutes) older video data is overwritten by new video data within the buffer. By way of example, an in room controller and/or facility master can make a temporary or buffered video recording of received video data from one or more cameras positioned within a patient's room.

Method 1800 includes an act 1802 of selectively archiving the temporarily buffered video data stream in response to a triggering event so as to permit later viewing of the archived video recording. Video archival data can be stored at a healthcare facility or offsite. The archived video recordings are typically merely a back-up that helps verify the occurrence of a prescribed event and do not constitute a "medical record"

within the meaning of HIPAA or other applicable statutes. By way of example and not by limitation, the triggering event may comprise at least one of:
  (i) entry into the room of an authorized tracking device encoded with entry rights associated with an authorized individual;
  (ii) entry into the room of an unauthorized tracking device associated with an unauthorized individual not having entry rights;
  (iii) entry into the room of an individual not associated with any tracking device;
  (iv) an asset used for a prescribed treatment and associated with an tracking device being located in the room; and/or
  (v) any other prescribed triggering event created by a given healthcare facility.

A tracking device can transmit any of a variety of different type signals, such as, for example RFID signals or ultrasound signals

C. Monitoring Patient Bed Rolling

Image analysis used to monitoring patient support exiting can also be used to monitor patient bed rolling behaviors. With bed-bound patients, skin breakdown, pressure sores and ulceration are important clinical concerns. To prevent these conditions from occurring, staff may be scheduled to relieve skin pressure points on the patient's body by manually turning the patient periodically (e.g., every 2, 3 or 4 hours as prescribed). This turning schedule disturbs the patient's natural sleep pattern, increases the risk of injuring the patient during the process, and adds significantly to staff workload.

By utilizing the in-room image analysis system to detect, record, count and report patient roll-overs, it will be possible to alert staff as to which patients require manual rolling over for each time period and which do not. Benefits to the patient include better sleep quality and less opportunity for tissue injury due to manual turning. Benefits to the staff include reduced work load by only turning those patients who actually require it. To visually verify that a patient has self-turned adequately during a time period, the system may allow for accelerated viewing of the buffered or recorded time period with real-speed viewing of detected turning events.

VI. Exemplary System Logic

By way of example only and not by limitation, the inventive systems and methods for patient, staff and visitor monitoring and response may employ the following exemplary logic:

Assigned Limit Variables
  [A]—head distance from headboard; initial value=30"
  [B]—head elevation from flat/down position; initial value=12"
  [C]—space between body and bedrail; initial value=5"—may need Small/Med/Large Values to reflect Patient body size
  [D]—hand on bedrail time; initial value=5 seconds
  [E]—bed bound/requires assist for exit; yes=1, no=0
  [F]—patient room assignment for RFID/ultrasound
  [G]—number of exit attempt for Torso Slide
  [H]—number of exit attempt for Torso Up/Leg Sweep
  [I]—number of exit attempt for Bedrail Roll
  [J]—number of exit attempt for Unknown Method
  [K]—family members video recorded; yes=1, no=0
  [L]—other residents video recorded within room; yes=1, no=0
  [M]—resident currently in facility; yes=1, no=0
  [N]—requires movement assistance; yes=1, no=0
  [O]—requires movement assistance every "X" hrs
  [P]—does the resident require a special diet; yes=1, no=0
  [Q]—does the resident require assistance during eating; yes=1, no=0
  [R]—number of RFID/ultrasound presences in eating area during breakfast, lunch and dinner times per day
  [S]—status of resident social interactions, maximum=10, minimum=0
  [T]—requires device specific therapy every "Y" hrs
  [U]—valid mobile emergency call button usage per month
  [V]—unwarranted mobile emergency call button usage per month
  [W]—is resident limited to movement within the facility; yes=1, no=0
  [X]—is resident limited to movement within their room; yes=1, no=0

Image Analysis Outputs
  (1) top of head to headboard distance (inches)
  (2) head elevation from flat position (inches)
  (3) leg in bed or out of bed (in/out)
  (4) space between body and bedrail (inches)
  (5) hand grasping bedrail duration (seconds)
  (6) no body in bed (absent/present)

Alert Conditions For Bed Exiting
For all [E]=1
Torso Slide=(1)>[A]
Torso Up/Leg Sweep=(2)>[B] and (3)=out
Bedrail Roll=(4)<[C] and (5)>[D]
Bed Exit Has Occurred=(6) is absent and RFID/ultrasound [F] is positive
  Action Taken For Positive Exit Alert
  check RFID/ultrasound for Staff presence at Nursing Station
    if no—then send pre-recorded message, alarm sent to closest shell staff RFID/ultrasound PDA, document, and go to Patient Profile Update
    if yes—then request Alert Verification or Alert Rejection from staff
      if neither Verify or Reject is given within 30 seconds then send pre-recorded message, alarm sent to closest shell staff RFID/ultrasound PDA, document and go to Patient Profile Update
    if yes and Alert Verification is Positive then
      alarm sent to closest shell staff RFID/ultrasound PDA
      Video/Audio link established with Nursing Station
      Patient Profile is Updated
    if yes and Alert Rejection is Positive then
      Possible Patient Profile Update (loosen alert criteria)
  Patient Profile Update For Bed Exiting
    [A]=[A]−[G] until [A]=20" then [A]=[A]
    [B]=[B]−[H] until [B]=6" then [B]=[B]
    [C]=[C]+([I]/3) until [C]=9" then [C]=[C]
    [D]=[D]−([I]/3) until [D]=2 seconds then [D]=[D]
  In-Room Camera Record On/Off Control
Camera Record is OFF until triggered by one of the following Actions:
  1. For [K]=yes and [L]=yes, the detection of an RFID/ultrasound that doesn't match with [F]
  2. For [K]=no and [L]=yes, the detection of an RFID/ultrasound that doesn't match with [F] and is not a Family RFID/ultrasound
  3. For [K]=yes and [L]=no, the detection of an RFID/ultrasound that doesn't match with [F] and is not a Resident RFID/ultrasound
  4. For [K]=no and [L]=no, the detection of an RFID that doesn't match with [F] and is not a Resident RFID/ultrasound or a Family RFID/ultrasound 5. Alternatively for 3. and 4., a numeric coded "CAMERA OFF" control pad could be accessible for each resident in each room then 3. and 4. would be deleted
6. Door motion detector detects motion and no RFID/ultrasound is detected in the zone immediately positioned by the door—Alert Security
7. Resident RFID/ultrasound [F] is detected but wide angle motion detector has not detected movement for over 12 hrs and [M]=1—Alert Nursing Station An actively recording camera is STOPPED from further recording by one of the following Actions:
1. The only detectable RFID/ultrasound signal is [F] and conditions (6) or (7) were not the source triggers
2. No RFID/ultrasound detection and no detected movement in the room for >0.5 hrs
3. Manual over-ride from Nursing Station Bed Bound Movement Therapy
1. For [N]=1, NUM=number of Staff RFID/ultrasound visits to room per 24 hrs
2. For [N]=1, INTV=time period since last exiting of Staff RFID/ultrasound from room
3. If INTV>0.9*[O] then Alert Nursing Station
4. If INTV>1.3*[O] then Alarm Nursing Station and Document Food/Nutrition Tracking
1. If [M]=1, [N]=0 and [R]=0 then Alarm and document
2. If [M]=1, [N]=0 and [R]=1 then Alert and RR=RR+1
3. If [M]=1, [N]=0 and RR>3 then Alarm and document Resident Requires Assistance When Eating
1. If [M]=1 and [Q]=1 then For Count Staff RFID/ultrasound and Food Tray RFID/ultrasound in Patient Room during meal times QQ=QQ+1 per day, reset QQ=0 each night
2. If QQ<3 then Alert
3. If QQ<2 then Alarm and document
(NOTE: if facility moves residents to another area for assistance with eating system will miss event)

Social Interaction Tracking
1. If RFID/ultrasound detected in Occupied Common Areas, then SI=SI+1
2. If Resident RFID/ultrasound detected in Room≠[F], then SI=SI+1
3. If detection of Assigned RFID/ultrasound in [F] and other Resident RFID/ultrasound in [F], then SI=SI+1
4. If detection of Family RFID/ultrasound in [F] while Assigned RFID/ultrasound is in [F], then SI=SI+1
5. At end of day, If SI>4 then [S]=[S]+1
6. At end of day, If SI=4 then [S]=[S]
7. At end of day, If SI=3 then [S]=[S]−1
8. At end of day, If SI=2 then [S]=[S]−2
9. At end of day, If SI=1 then [S]=[S]−3 and Alert Nursing Station
10. At end of day, If SI=0 then [S]=[S]−4 and Alarm Nursing Station and document
11. At end of day, If S<5 then Alert Nursing Station
12. At end of day, If S<1 then Alarm Nursing Station and Document In-Room Therapy Requiring Special Equipment
1. Skip entire subroutine If [M]=0 or [T]=0
2. If Staff RFID/ultrasound and Device RFID/ultrasound are detected in [F], then TD=TD+1
3. If (current military time)>1.2*[T] and TD=0 then Alarm Nursing Station and document
4. If TD=1 then begin TDT=timer
5. If TDT>0.9*[T] then Alert Nursing Station
6. If TDT>1.2*[T] then Alarm Nursing Station and document
7. If TD=2 then TDT=0 and begin timer and TD=0
8. Loop back to 1.

RFID/Ultrasound Mobile Emergency Call Button
1. Unique Emergency RFID/ultrasound is detected
2. Individual Resident is Identified
3. Resident Location is Identified
4. Nursing Station is Alarmed
5. Location is compared to list of "wired" facility locations
6. If location is "wired", video/audio link is established with Nursing Station
7. If RFID/ultrasound of Staff is present at Nursing Station and "wired" link existed, then wait 30 seconds for (VERIFY/REJECT) from Nursing Station before Alarm is transmitted to PDAs. Send Alarm immediately for VERIFY, no Alarm for REJECT.
8. If VERIFY then [U]=[U]+1, reset to [U]=0 at first of month
9. If REJECT then [V]=[V]+1, reset to [V]=0 at first of month
10. If [U]>1, document to staff "high risk resident"
11. If [V]>3, document to staff "resident requires counseling"

Resident Wandering Detection
1. If [W]=1 and solo Resident RFID/ultrasound (no associated Staff or Family RFID/ultrasound) is detected approaching or at exit then
   a. Alert Nursing Station
   b. Wait 30 seconds for VERIFY/REJECT
   c. If VERIFY then Establish Video/audio link if location is "wired"
   d. If VERIFY then Alarm Staff/Security PDAs
   e. Document Event
   f. If 30 seconds elapse with no response from Nursing Station then d. & e.
2. If [X]=1 and solo Resident RFID/ultrasound (no associated Staff or Family RFID/ultrasound) is detected outside room [F] then
   a. Alert Nursing Station
   b. Wait 30 seconds for VERIFY/REJECT
   c. If VERIFY then Establish Video/audio link if location is "wired"
   d. If VERIFY then Alarm Staff PDAs
   e. Document Event
   f. If 30 seconds elapse with no response from Nursing Station then d. & e.
3. If Resident RFID/ultrasound is detected in any Facility Area that is denoted "Restricted" without the presence of Staff RFID/ultrasound then
   a. Alert Nursing Station
   b. Wait 30 seconds for VERIFY/REJECT
   c. If VERIFY then Establish Video/audio link if location is "wired"
   d. If VERIFY then Alarm Staff/Security PDAs
   e. Document Event
   f. If 30 seconds elapse with no response from Nursing Station then d. & e.

"Closest Staff Locator"/Shell Method
For a uniform grid of RFID/ultrasound zones measuring MM by NN and numbered from left to right, starting in the upper left zone
Shell 0=X (the present location of the Resident in need)
Shell 1=X−1, X+1, X+MM, X−MM, X+MM+1, X+MM−1, X−MM+1, X−MM−1
Shell 2=X−2, X+2, X−2+MM, X−2−MM, X−2+2MM, X−2−2MM, X+2+MM, X+2−MM, X+2+2MM, X+2−2MM, X−2MM, X−2MM+1, X−2MM−1, X+2MM, X+2MM+1, X+2MM−1

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. In a computer system that includes a processor, system memory, and stationary storage apparatus, that maintains stored profiles for a plurality of patients at a facility, and that receives data from networked computers or other devices at the facility relating to behavior, activities, care, wellness or other information for each patient, a method for maintaining and refining the stored profiles for patients at the facility comprising:

the computer system storing on the stationary storage apparatus an initial profile for each of a plurality of patients at a facility based on at least one of specific personalized information for each patient or general information common to more than one patient, the profile including at least one of a limit for detecting an event, an alarm level for use in detecting an actionable event, a care regimen for the patient, or a wellness parameter for the patient, wherein the profile includes both static data and dynamic data;

the computer system receiving collected data related to detected events, actionable events, care regimens, and/or wellness parameters for at least some of the patients at the facility, the data being collected at least in part using sensors, cameras and/or computers positioned within the facility that detect and/or analyze data regarding locations and/or movements of at least some of the patients at the facility, locations and/or movements of at least some of the staff members, assets and/or visitors at the facility, physical condition of at least some of the patients, and/or activities performed on and/or by at least some of the patients; and the computer system refining the profiles for at least some of the patients at the facility based on the collected data in order to modify at least one of limits or alarm levels and storing refined profiles for at least some of the patients at the facility on the stationary storage apparatus, wherein refining the profiles includes altering the dynamic data of the refined profiles.

2. A method as defined in claim 1, wherein the profile is refined by the computer system automatically altering the limit level, alarm level, treatment regimen, and/or wellness parameter.

3. A method as defined in claim 1, wherein the profile is refined by a staff member manually altering the limit level, alarm level, treatment regimen, and/or wellness parameter.

4. A method as defined in claim 1, wherein the profile is automatically refined in response to an ultrasound detector detecting an ultrasound signal indicative the occurrence of an event.

5. A method as defined in claim 1, wherein the static data remains unmodified.

6. A method as defined in claim 1, the limit for the patient being refined in order to more accurately determine occurrence of an event.

7. A method as defined in claim 1, the alarm level for the patient being refined in order to more accurately determine occurrence of an actionable event.

8. A method as defined in claim 1, the event being detected in accordance with a recursively refined profile for the patient based at least in part on previously collected data.

9. A method as defined in claim 1, the profile including data relating to movements by the patient that are predictive of bed exiting by that patient.

10. A method as defined in claim 9, the profile including data relating to movements by the patient that are predictive of bed exiting comprises data resulting from ultrasound sensors in an ultrasound detection grid detecting movements of one or more ultrasound transmitters attached to the patient.

11. A method as defined in claim 9, the profile including a plurality of limits that indicate a plurality of corresponding body part positions that, when attained simultaneously or sequentially, are predictive of bed existing.

12. A method as defined in claim 9, the refining act including modifying the limits based on collected data in order to further reduce the risk of unattended bed exiting and/or false positive alerts or alarms.

13. A method as defined in claim 1, wherein the collected data relates to an event, the method further comprising staff verifying whether or not the event is an actionable event, wherein verifying or rejection the event as an actionable event forms part of an information feedback loop that at least partially comprises the refining act.

14. A method as defined in claim 13, wherein the event and/or actionable event relate to at least one of patient wandering into unauthorized zones, patient flight from the facility, patient support exiting, patient initiated alert, failure to complete a prescribed regimen, or patient injury.

15. A method as defined in claim 1, the patient profile being refined based on a measured level of social interaction by the patient.

16. A method as defined in claim 1, the patient profile being refined based on a measured level of total ambulation by the patient over a predetermined period of time.

17. A method as defined in claim 1, the patient profile being refined based on a measured level of total ambulation by the patient over a predetermined period of time in association with a previously defined personal ambulation assistive device.

18. A method as defined in claim 17, the patient profile being refined based on a measured level of total ambulation by the patient over a predetermined period of time in association with a previously defined personal ambulation assistive device comprises refining the patient profile based on detected ultrasound signals from an ultrasound transmitted attached the patient.

19. A method as defined in claim 1, the patient profile being refined based on a measured level of denture use by the patient.

20. A method as defined in claim 1, the patient profile being refined based on a measured level of denture cleaning compared to denture cleaning schedules utilized by staff.

21. A method as defined in claim 1, the patient profile being refined based completion of a prescribed patient treatment.

22. A method as defined in claim 21, wherein the prescribed patient treatment involves an interaction between the patient and at least one of a caregiver or asset.

23. A method as defined in claim 1, the patient profile being refined based on changes in patient gait.

24. A method as defined in claim 1, the patient profile being refined based on patient breathing that is indicative of a medical condition.

25. A method as defined in claim 1, further comprising storing a performance profile for a plurality of caregivers and/or visitors at the facility relating to caregiver and/or visitor performance, collecting data regarding the locations and/or movements by the caregivers and/or visitors, and refining caregiver and/or visitor performance profiles based on the collected data.

26. A computer-program product comprising one or more tangible computer-readable media having stored thereon computer-executable instructions that, when executed by a processor, cause the computer system to implement the method of claim 1.

27. In a computer system that includes a processor, system memory, and stationary storage apparatus, that maintains stored profiles for a plurality of patients at a facility, and that receives data from networked computers or other devices at the facility relating to behavior, activities, care, wellness or other information for each patient, a method for maintaining and refining the stored profiles for patients at the facility comprising:

storing an initial profile on the stationary storage apparatus for each of a plurality of patients at a facility based on at least one of specific personalized information for each patient or general information common to more than one patient, the profile including at least one of a limit for detecting an event, an alarm level for use in detecting an actionable event, a care regimen for a patient, or a wellness parameter for a patient, wherein each patient profile includes both static data and dynamic data;

receiving collected data related to detected events, actionable events, care regimens, and/or wellness parameters for at least some of the patients at the facility, the data being collected at least in part using sensors, cameras and/or computers positioned within the facility that detect and/or analyze data regarding locations and/or movements of at least some of the patients at the facility, locations and/or movements by of at least some of staff members, assets and/or visitors at the facility, physical condition of at least some of the patients, and/or activities performed on and/or by at least some of the patients; and refining the profiles for at least some of the plurality of patients at the facility based on the collected data in order to modify at least one of limits or alarm levels and storing refined profiles for at least some of the patients at the facility on the stationary storage apparatus, at least some of the patient profiles differing as among different patients according to individual attributes and/or needs of the patients, wherein refining the profiles includes altering the dynamic data of the refined profile.

28. In a computer system that includes a processor, system memory, and stationary storage apparatus, that maintains stored profiles for patients, staff and visitors at a facility, and that receives data from networked computers or other devices at the facility relating to patient care and wellness quality and staff and visitor performance at a healthcare facility, a method for maintaining and refining the stored profiles for patients, staff members, and visitors at the facility comprising:

the computer system storing on the stationary storage apparatus initial profiles for the patients, staff members, and visitors at the facility based on at least one of specific personalized information for the patients, staff members or visitors or general information common to more than one patient, staff member or visitor, the profiles for at least some of the patients including at least one of a limit for detecting an event, an alarm level for use in detecting an actionable event, a care regimen for a given patient, or a wellness parameter for the given patient, the profiles for at least some of the staff members including a performance parameter for a given staff member, the profiles for at least some of the visitors including a performance parameter for a given visitor;

the computer system receiving collected data related to detected events, actionable events, care regimens, and/or wellness parameters for at least some of the patients at the facility, performance parameters for at least some of the staff members at the facility, and performance parameters for at least some of the visitors at the facility, the data being collected at least in part using RFID detectors and/or ultrasound detectors positioned at various locations within the facility that detect and/or analyze data regarding locations and/or movements by at least some of the patients at the facility, locations and/or movements by at least some of the staff members, and visitors at the facility, physical condition of at least some of the patients, and activities performed on and/or by at least some of the patients;

the computer system refining the profiles for at least some of the patients, staff members, and visitors based on the collected data in order to modify at least one of limits, alarm levels, care regimens, or wellness parameters for at least some of the patients, the performance parameters for at least some of the staff members, and the performance parameters for at least some of the visitors; and the computer system storing refined profiles for at least some of the patients, staff members, and visitors at the facility on the stationary storage apparatus.

29. The method as recited in claim 1, wherein receiving collected data comprises an act of receiving collected data that was collected using a plurality of ultrasound detectors positioned at various locations within the facility.

30. The method as recited in claim 1, wherein receiving collected data comprises an act of receiving collected data that was collected using a plurality of RFID sensors positioned at various locations within the facility.

31. In a computer system that includes a processor, system memory, and stationary storage apparatus, that maintains stored profiles for patients, staff and visitors at a facility, and that receives data from networked computers or other devices at the facility relating to patient care and wellness quality and staff and of visitor performance at a healthcare facility, a method for maintaining and refining the stored profiles for patients and at least one of staff members or visitors at the facility comprising:

the computer system storing on the stationary storage apparatus an initial profile for each of the patients at the facility based on at least one of specific personalized information for the patients or general information common to more than one patient, the profile for each patient including at least one of a limit for detecting an event, an alarm level for use in detecting an actionable event, a care regimen, or a wellness parameter;

the computer system further storing an initial profile for at least one of a staff member or visitor at the facility based on at least one of specific personalized information for the staff member and/or visitor, or general information common to more than one staff member and/or visitor, the profile for the staff member, if stored by the computer system, including a performance parameter for the staff member and/or the profile for the visitor, if stored by the computer system, including a performance parameter for the visitor;

the computer system receiving collected data related to at least one of (i) a detected event or an actionable event that involves detecting bodily movements of a patient positioned on a bed which are predictive of attempted bed exiting by the patient, (ii) a care regimen for a patient, (iii) a wellness parameter for a patient, a (iv) performance parameter for a staff member, or (v) a performance parameter for a visitor, the data being collected using one or more of a sensor, camera, or computer positioned within the facility that detect and/or analyze data regarding at least one of location and/or movements by the patient, location and/or movements by staff members, assets and/or visitors, physical condition of the patient, or activities performed on and/or by the patient; and the computer system refining the profile for at least one of the patient, staff member or visitor based on the collected data in order to modify at least one of the limit, alarm level, care regimen, or wellness parameter of the patient and/or performance parameter of the staff member and/or visitor; and the computer system storing refined profiles for at least one of the patient, staff member or visitor at the facility on the stationary storage apparatus.

\* \* \* \* \*